US012583929B2

(12) United States Patent
Baz Morelli et al.

(10) Patent No.: US 12,583,929 B2
(45) Date of Patent: Mar. 24, 2026

(54) METHOD OF TREATING ACUTE RESPIRATORY DISTRESS SYNDROME

(71) Applicant: CSL INNOVATION PTY LTD, Melbourne (AU)

(72) Inventors: Adriana Baz Morelli, Melbourne (AU); Ian Keith Campbell, Melbourne (AU); Karolina Krstevski, Melbourne (AU)

(73) Assignee: CSL Innovation Pty Ltd, Melbourne VIC (AU)

( * ) Notice: Subject to any disclaimer, the term of this patent is extended or adjusted under 35 U.S.C. 154(b) by 697 days.

(21) Appl. No.: 18/000,153

(22) PCT Filed: Jun. 7, 2021

(86) PCT No.: PCT/AU2021/050568
§ 371 (c)(1),
(2) Date: Nov. 29, 2022

(87) PCT Pub. No.: WO2021/243424
PCT Pub. Date: Dec. 9, 2021

(65) Prior Publication Data
US 2023/0272087 A1     Aug. 31, 2023

(30) Foreign Application Priority Data
Jun. 4, 2020     (AU) ................................ 2020901843

(51) Int. Cl.
C07K 16/28       (2006.01)
A61K 39/00       (2006.01)
A61P 11/00       (2006.01)

(52) U.S. Cl.
CPC .......... C07K 16/2866 (2013.01); A61P 11/00 (2018.01); *A61K 2039/505* (2013.01); *A61K 2039/54* (2013.01); *A61K 2039/545* (2013.01); *C07K 2317/76* (2013.01)

(58) Field of Classification Search
CPC .. C07K 16/2866; C07K 2317/76; A61P 11/00
See application file for complete search history.

(56) References Cited

U.S. PATENT DOCUMENTS

| | | | |
|---|---|---|---|
| 4,196,265 A | 4/1980 | Koprowski et al. |
| 4,676,980 A | 6/1987 | Segal et al. |
| 4,816,567 A | 3/1989 | Cabilly et al. |
| 5,225,539 A | 7/1993 | Winter |
| 5,270,163 A | 12/1993 | Gold et al. |
| 5,422,248 A | 6/1995 | Smith et al. |
| 5,475,096 A | 12/1995 | Gold et al. |
| 5,530,101 A | 6/1996 | Queen et al. |
| 5,585,089 A | 12/1996 | Queen et al. |
| 5,589,456 A | 12/1996 | Smith et al. |
| 5,731,168 A | 3/1998 | Carter et al. |
| 5,807,715 A | 9/1998 | Morrison et al. |
| 5,885,793 A | 3/1999 | Griffiths et al. |
| 6,248,516 B1 | 6/2001 | Winter et al. |
| 6,300,064 B1 | 10/2001 | Knappik et al. |
| 7,083,784 B2 | 8/2006 | Dall'Acqua et al. |
| 7,108,852 B2 | 9/2006 | Devalaraja et al. |
| 7,250,297 B1 | 7/2007 | Beste et al. |
| 7,871,979 B2 | 1/2011 | Yorke-Smith et al. |
| 9,193,793 B2 | 11/2015 | Nash et al. |
| 9,382,538 B2 | 7/2016 | Collard et al. |
| 9,649,356 B2 | 5/2017 | Seelen |
| 2004/0132028 A1 | 7/2004 | Stumpp et al. |
| 2007/0059280 A1 | 3/2007 | Devalaraja et al. |
| 2007/0135620 A1 | 6/2007 | Chamberlain et al. |
| 2007/0224633 A1 | 9/2007 | Skerra et al. |
| 2008/0139791 A1 | 6/2008 | Lipovsek et al. |
| 2008/0199426 A1 | 8/2008 | Sukhatme et al. |
| 2009/0324591 A1 | 12/2009 | Crump et al. |
| 2010/0004167 A1 | 1/2010 | Yorke-Smith et al. |
| 2011/0110934 A1 | 5/2011 | Wicks et al. |
| 2012/0321630 A1 | 12/2012 | Nash et al. |
| 2013/0259824 A1 | 10/2013 | Wu et al. |
| 2019/0343918 A1 | 11/2019 | Graham et al. |

FOREIGN PATENT DOCUMENTS

| | | |
|---|---|---|
| CN | 107106681 A | 8/2017 |
| CN | 109310884 A | 2/2019 |
| EP | 0 569 141 A2 | 11/1993 |
| EP | 1 167 390 A1 | 1/2002 |
| EP | 1 641 818 B1 | 12/2008 |
| WO | WO 94/04678 | 3/1994 |

(Continued)

OTHER PUBLICATIONS

Klein et al. Epitope interactions of monoclonal antibodies targeting CD20 and their relationship to functional properties. MABS, 5, 22-33,2013. (Year: 2013).*
Lloyd et al. Protein Engineering, Design & Selection 22:159-168, 2009. (Year: 2009).*
Aggarwal et al., "G-CSF and IL-8 but not GM-CSF correlate with severity of pulmonary neutrophilia in acute respiratory distress syndrome," Eur Respir J, 15:895-901 (2000).
International Search Report for PCT/AU2021/050568, dated Sep. 24, 2021, 6 pages.
Liao et al., "Progress on role of cytokine storm in exacerbation of coronavirus disease 2019 (COVID-19): Review," 36(10):941-947, Abstract only (2020).

(Continued)

*Primary Examiner* — Elly-Gerald Stoica
(74) *Attorney, Agent, or Firm* — Finnegan, Henderson, Farabow, Garrett & Dunner, LLP

(57)     ABSTRACT

The present disclosure relates to methods of treating or preventing acute respiratory distress syndrome (ARDS) using compounds that inhibit G-CSF signaling. The present disclosure also relates to compounds for use in the treatment or prevention of ARDS, as well as the use of such compounds in the manufacture of medicaments for the treatment or prevention of ARDS.

17 Claims, 16 Drawing Sheets
Specification includes a Sequence Listing.

(56)                 References Cited

FOREIGN PATENT DOCUMENTS

| WO | WO 94/07921 | | 4/1994 |
|----|----|----|----|
| WO | WO 95/21867 | | 8/1995 |
| WO | WO 97/49805 | | 12/1997 |
| WO | WO 98/44001 | | 10/1998 |
| WO | WO 99/32619 | | 7/1999 |
| WO | WO 99/45110 | | 9/1999 |
| WO | WO 99/49029 | | 9/1999 |
| WO | WO 99/53050 | | 10/1999 |
| WO | WO 99/57134 | | 11/1999 |
| WO | WO 00/34317 | | 6/2000 |
| WO | WO 01/34815 | A1 | 5/2001 |
| WO | WO 02/080967 | A1 | 10/2002 |
| WO | WO 02/088171 | A2 | 11/2002 |
| WO | WO 02/098216 | A1 | 12/2002 |
| WO | WO 2004/064724 | A2 | 8/2004 |
| WO | WO 2004/108158 | A1 | 12/2004 |
| WO | WO 2005/056764 | A2 | 6/2005 |
| WO | WO 2005/118629 | A1 | 12/2005 |
| WO | WO 2006/033386 | A1 | 3/2006 |
| WO | WO 2007/025166 | A2 | 3/2007 |
| WO | WO 2008/003763 | A1 | 1/2008 |
| WO | WO 2008/017126 | A1 | 2/2008 |
| WO | WO 2009/039337 | A2 | 3/2009 |
| WO | WO 2010/080538 | A1 | 7/2010 |
| WO | WO 2010/085682 | A2 | 7/2010 |
| WO | WO 2011/033204 | A1 | 3/2011 |
| WO | WO 2011/051489 | A2 | 5/2011 |
| WO | WO 2011/103076 | A1 | 8/2011 |
| WO | WO 2011/107595 | A1 | 9/2011 |
| WO | WO 2012/112188 | A1 | 8/2012 |
| WO | WO 2012/171057 | A1 | 12/2012 |
| WO | WO 2013/075066 | A2 | 5/2013 |
| WO | WO 2014/072481 | A1 | 5/2014 |
| WO | WO 2014/179657 | A1 | 11/2014 |
| WO | WO 2015/063611 | A2 | 5/2015 |
| WO | WO 2015/127405 | A2 | 8/2015 |
| WO | WO 2019/104385 | A1 | 6/2019 |
| WO | WO 2019/124666 | A2 | 6/2019 |
| WO | WO 2019/178645 | A1 | 9/2019 |
| WO | WO 2020/097139 | A1 | 5/2020 |
| WO | WO 2020/113270 | A1 | 6/2020 |
| WO | WO 2020/248024 | A1 | 12/2020 |

OTHER PUBLICATIONS

Wang et al., "Anti G-CSFR Antibody Treatment Suppresses Neutrophilic and Type-2 Lung Inflammation in an Allergic Asthma Model Worsened by Neonatal Co-Infection," Tsanz Oral Presentations, Respirology, 23(Suppl. 1): 21-103 (2018).
Wang et al., "G-CSFR antagonism reduces neutrophilic inflammation during pneumococcal and influenza respiratory infections without compromising clearance," Scientific Reports, 9:17732 (2019).
Written Opinion of the International Searching Authority for PCT/AU2021/050568, dated Sep. 24, 2021, 10 pages.
Akihama et al., "Bone Marrow-Derived Cells Mobilized by Granulocyte-Colony Stimulating Factor Facilitate Vascular Regeneration in Mouse Kidney after Ischemia/Reperfusion Injury," Tohoku J. Exp. Med., 213:341-349 (2007).
Ashchyan et al., Neutrophilic dermatoses: Pyoderma gangrenosum and other bowel- and arthritis—associated neutrophilic dermatoses, J Am Acad Dermatol (2018).
ANZCTR, "Dose escalation, placebo-controlled phase 1 study to assess the safety and tolerability of CSL324 in healthy adults," (2016).
Banuelos et al., "Granulocyte colony-stimulating factor blockade enables dexamethasone to inhibit lipopolysaccharide-induced murine lung neutrophils," PLOS One, 12(5):e0177884 (2017).
Bendele, "Animal models of rheumatoid arthritis," J Musculoskel Neuron Interact, 1(4):377-385 (2001).
Bidyasar et al., "Sweet Syndrome Associated With Granulocyte Colony-Stimulating Factor," (2008).

Bostanci et al., "The protective effect of G-CSF on experimental ischemia/reperfusion injury in rat ovary," Arch Gynecol Obstet, 293:789-795 (2016).
Bozinovski et al., "Granulocyte/Macrophage-Colony-stimulating factor (GM-CSF) Regulates Lung Innate Immunity to Lipopolysaccharide through Akt/Erk Activation of $NF_kB$ and AP-1 in Vivo," The Journal of Biological Chemistry, 277(45): 42808-42814 (2002).
Butler et al., "What Do Autoinflammatory Syndromes Teach About Common Cutaneous Diseases Such as Pyoderma Gangrenosum? A Commentary," Dermatol Clin, 31:427-435 (2013).
Campbell et al., "Therapeutic Targeting of the G-CSF Receptor Reduces Neutrophil Trafficking and Joint Inflammation in Antibody-Mediated Inflammatory Arthritis," The Journal of Immunology, (2016).
Cugno et al., "Inflammatory Joint Disorders and Neutrophilic Dermatoses: a Comprehensive Review," Clinic Rev Allerg Immunol, 54:269-281 (2018).
De La Lastra et al., "Epitope mapping of 10 monoclonal antibodies against the pig analogue of human membrane cofactor protein (MCP)," Immunology, 96:663-670 (1999).
De Vries et al., "Complement Factor C5a Mediates Renal Ischemia-Reperfusion Injury Independent from Neutrophils," J Immunol, 170:3883-3889 (2003).
Debruin et al., "Most purported antibodies to the human granulocyte colony-stimulating factor receptor are not specific," Experimental Hematology, 38:1022-1035 (2010).
Dondelinger et al., "Understanding the Significance and Implications of Antibody Numbering and Antigen-Binding Surface/Residue Domain," Frontiers in Immunology, 9:1-15 (2018).
Draper et al., "Bullous Sweet's syndrome in congenital neutropenia: Association with pegfilgrastim," J Am Acad Dermatol, 52(5) (2005).
Elsässer et al., "The fusion protein AML1-ETO in acute myeloid leukemia with translocation t(8;21) induces c-jun protein expression via the proximal AP-1 site of the c-jun promoter in an indirect, JNK-dependent matter," Oncogene, 22:5646-5657 (2003).
Fujii et al., "Sweet's Syndrome Successfully Treated with Granulocyte and Monocyte Adsorption Apheresis," Case Rep Dermatol, 9:13-18 (2017).
Fukunaga et al., "Three different mRNAs encoding human granulocyte colony-stimulating factor receptor," Proc. Natl. Acad. Sci. USA, 87:8702-8706 (1990).
Goldberg et al., "G-CSF and Neutrophils Are Nonredundant Mediators of Murine Experimental Autoimmune Uveoretinitis," The American Journal of Pathology, 186(1) (2016).
Guo et al., "The origin, transmission and clinical therapies on coronavirus disease 2019 (COVID-19) outbreak—an update on the status," Military Medical Research, 7:11 (2020).
Higuchi et al., "Granulocyte Colony-Stimulating Factor Prevents Reperfusion Injury After Heart Preservation," Ann Thorac Surg, 85:1367-1373 (2008).
Huang et al., "Clinical features of patients infected with 2019 novel coronavirus in Wuhan, China," Lancet, 395:497-506 (2020).
Jiang et al., "Role for Granulocyte Colony Stimulating Factor in Angiotensin II-Induced Neutrophil Recruitment and Cardiac Fibrosis in Mice," American Journal of Hypertension, 26(10) (2013).
Kawakami et al., "Elevated Serum Granulocyte Colony-Stimulating Factor Levels in Patients with Active Phase of Sweet Syndrome and Patients With Active Behcet Disease," Arch Dermatol, 140:570-574 (2004).
Ko et al., "Affinity Maturation of Monoclonal Antibody 1E11 by Targeted Randomization in CDR3 Regions Optimizes Therapeutic Antibody Targeting of HER2-Positive Gastric Cancer," PLOS One, 10(7):e0134600 (2015).
Layton et al., "Identification of a Ligand-binding Site on the Granulocyte Colony-stimulating Factor Receptor by Molecular Modeling and Mutagenesis," The Journal of Biological Chemistry, 272(47):29735-29741 (1997).
Layton et al., "Neutralising Antibodies to the Granulocyte Colony-stimulating Factor Receptor Recognize both the Immunoglobulin-like Domain and the Cytokine Receptor Homologous Domain," Growth Factors, 14:117-130 (1997).
Layton et al., "Interaction of Granulocyte Colony-stimulating Factor (G-CSF) with Its Receptor," 274(25):17445-17451 (1999).

(56)     References Cited

OTHER PUBLICATIONS

Layton et al., "Identification of Ligand-binding Site III on the Immunoglobulin-like Domain of the Granulocyte Colony-stimulating Factor Receptor," 276(39):36779-36787 (2001).

Layton et al., "The interaction of G-CSF with its receptor," Frontiers in Bioscience, 11:3181-3189 (2006).

Lescure et al., "Clinical and virological data of the first cases of COVID-19 in Europe: a case series," Lancet Infect Dis (2020).

Li et al., "X-ray snapshots of the maturation of an antibody response to a protein antigen," Nature Structural Biology, 10(6) (2003).

Li et al., "Pretreatment with granulocyte colony-stimulating factor attenuated renal ischaemia and reperfusion injury via activation of PI3/Akt signal pathway," Nephrology, 13:508-516 (2008).

Lloyd et al., "Modelling the human immune response: performance of a $10^{11}$ human antibody repertoire against a broad panel of therapeutically relevant antigens," Protein Engineering, Design & Selection, 22(3):159-168 (2009).

Lu et al., "Neuroprotection of G-CSF in cerebral ischemia," Frontiers in Bioscience, 12:2869-2875 (2007).

Navarini et al., "Neutrophilic dermatoses and autoinflammatory diseases with skin involvement—*innate immune disorders*," Semin Immunopathol, 38:45-56 (2016).

Nelson et al., "Neutrophilic dermatoses: Pathogenesis, Sweet syndrome, neutrophilic eccrine hidradenitis, and Behçet disease," J Am Acad Dermatol (2018).

Nishida et al., "How Does G-CSF Act on the Kidney during Acute Tubular Injury?" Nephron Exp Nephrol, 104:e123-128 (2006).

Nogueira et al., "Granulocyte Colony Stimulating Factor Prevents Kidney Infarction and Attenuates Renovascular Hypertension," Cell Physiol Biochem, 29:143-152 (2012).

Prendiville et al., "Neutrophilic Dermatoses in Two Children with Idiopathic Neutropenia: Association with Granulocyte Colony-Stimulating Factor (G-CSF) Therapy," Pediatric Dermatology, 18(5):417-421 (2001).

Rajpal et al., "A general method for greatly improving the affinity of antibodies by using combinatorial libraries," PNAS, 102(24):8466-8471 (2005).

Qin et al., "Dysregulation of immune response in patients with COVID-19 in Wuhan, China," (2020).

Queto et al., "G-CSF suppresses allergic pulmonary inflammation, downmodulating cytokine, chemokine and eosinophil production," Life Sciences, 88:830-838 (2011).

Salvadori et al., "Update on ischemia-reperfusion injury in kidney transplantation: Pathogenesis and treatment," World J Transplant, 5(2):52-67 (2015).

Scalzo-Inguanti et al., "A neutralizing anti-G-CSFR antibody blocks G-CSF-induced neutrophilia without inducing neutropenia in non-human primates," Journal of Leukocyte Biology, 102:537-549 (2017).

Shima et al., "Neuroprotective Effects of Granulocyte Colony-Stimulating Factor on Ischemia-Reperfusion Injury of the Retina," Ophthalmic Res, 48:199-207 (2012).

Steinberg et al., "Evolution of Bronchoalveolar Cell Populations in the Adult Respiratory Distress Syndrome," American Journal of Respiratory and Critical Care Medicine, 150 (1994).

Tian et al., "Pulmonary Pathology of Early-Phase 2019 Novel Coronavirus (COVID-19) Pneumonia in Two Patients With Lung Cancer," Journal of Thoracic Oncology (2020).

Toussaint et al., "Host DNA released by NETosis promotes rhinovirus-induced type-2 allergic asthma exacerbation," Nature Medicine, 23(6) (2017).

Ueda et al., "Granulocyte Colony Stimulating Factor Directly Inhibits Myocardial Ischemia-Reperfusion Injury Through Akt-Endothelial NO Synthase Pathway," Arterioscler Throm Vasc Biol. (2006).

Uhara et al., "Neutrophilic dermatoses with acute myeloid leukemia associated with an increase of serum colony-stimulating factor," J Am Acad Dermatol, 59(2) (2008).

Yan et al., "Granulocyte Colony-Stimulating Factor Attenuates Renal Ischemia-Reperfusion Injury by Inducing Myeloid-Derived Suppressor Cells," JASN, 31:731-746 (2020).

Yao et al., "The A's Have It: Developing Apolipoprotein A-I Mimetic Peptides Into a Novel Treatment for Asthma," Chest, 150(2):283-288 (2016).

Zhang et al., "Ischemia-reperfusion induces G-CSF gene expression by renal medullary thick ascending limb cells in vivo and in vitro," Am J Physiol Renal Physiol, 286:F1193-F1201 (2004).

\* cited by examiner

| Dose Group Subject number | Pre-infusion Day 1 | Day 2 | Day 3 | Day 4 | Day 5 | Day 8 | Day 11 | Day 15 | Day 23 | Day 29 | Day 41 | Day 51 | Day 85 SFU |
|---|---|---|---|---|---|---|---|---|---|---|---|---|---|
| 0.1 mg/kg CSL 324 (Cohort A1) | | | | | | | | | | | | | |
| 0360045-007 | | | | | | | | | | | | | |
| 0360045-0012 | | | | | | | | | | | | | |
| 0360045-0017 | | 2 | 2 | 1 | | 1 | | | | 1 | | 1 | |
| 0360045-0020 | | 2 | 2 | 2 | 2 | | | | | | | | |
| 0.3 mg/kg CSL 324 (Cohort A2) | | | | | | | | | | | | | |
| 0360045-0028 | | 1 | | | | | | | | | | | |
| 0360045-0032 | | 1 | 2 | | | 1 | | | | | | | |
| 0360045-0036 | | | | | | | | | | | | | |
| 0360045-0044 | | 1 | | | | | | | | | | | |
| 1.0 mg/kg CSL 324 (Cohort A3) | | | | | | | | | | | | | |
| 0360045-0058 | | 2 | 2 | 3 | 2 | | | | | | 2 | | |
| 0360045-0064 | | | | | | | | | | 1 | | | |
| 0360045-0069 | | | 2 | 2 | 1 | | | 1 | 1 | 2 | 1 | | |
| 0360045-0070 | | 1 | | 1 | 1 | 1 | | | 1 | 1 | | | |
| 0.6 mg/kg CSL 324 (Cohort A4) | | | | | | | | | | | | | |
| 0360045-0127 | | | | | | | | | | | | | |
| 0360045-0132 | | | | | | 1 | | | | | | | |
| 0360045-0133 | | | 1 | 1 | | 1 | 2 | 1 | 1 | | | | |
| 0360045-0140 | | | | 1 | | | | | | | | | |
| 0.8 mg/kg CSL 324 (Cohort A5) | | | | | | | | | | | | | |
| 0360045-0146 | | 1 | | | 1 | 1 | | 1 | 1 | 1 | | | |
| 0360045-0150 | | | 1 | | | 1 | | | | 1 | 1 | | |
| 0360045-0167 | | | | | | | | | | 1 | | | |
| 0360045-0170 | | | | | | | | | | | | | |

FIGURE 3

| Dose Group Subject number | Pre-infusion Day 1 | Day 2 | Day 3 | Day 4 | Day 5 | Day 8 | Day 21 | Pre-infusion Day 22 | Day 23 | Day 24 | Day 29 | Day 42 | Pre-infusion Day 43 | Day 44 | Day 45 | Day 49 | Day 56 | Day 63 | Day 70 | Day 129 SFU/ET |
|---|---|---|---|---|---|---|---|---|---|---|---|---|---|---|---|---|---|---|---|---|
| 0.6 mg/kg CSL 324 (Part C) | | | | | | | | | | | | | | | | | | | | |
| 0360045-0203 | | | | | | | | | 1 | 1 | 2 | | 2 | 2 | 1 | 2 | 1 | | 2 | |
| 0360045-0207 | | | | | | | | | | | | | 1 | 2 | 1 | 1 | | | 1 | |
| 0360045-0222 | | 1 | 1 | | | | | | | 1 | 1 | | | 2 | 1 | 3 | 1 | 1 | 2 | |
| 0360045-0224[a] | | 2 | 2 | 1 | 1 | 1 | | | 2 | 2 | 3 | 2 | 2 | 2 | 3 | 1 | 1 | 1 | | |
| 0360045-0228 | | | | | | | 2 | 1 | 2 | 2 | | 1 | | 1 | 2 | 3 | 2 | 2 | 2 | 2 |
| 0360045-0235[a,b] | | 2 | 2 | 3 | 1 | 1 | 2 | 2 | 1 | | 1 | | 2 | 2 | | 3 | 2 | 2 | | |

FIGURE 4

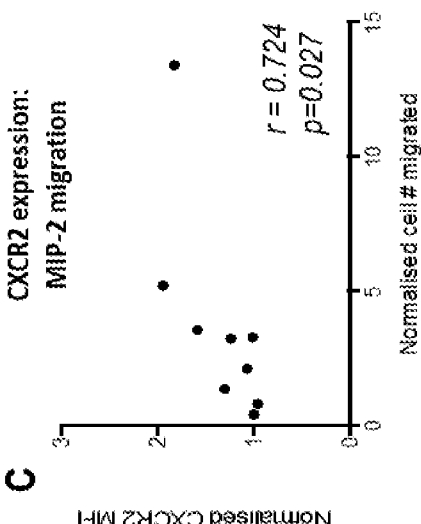
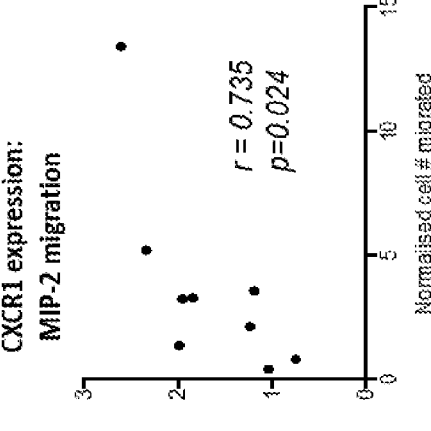
FIGURE 6
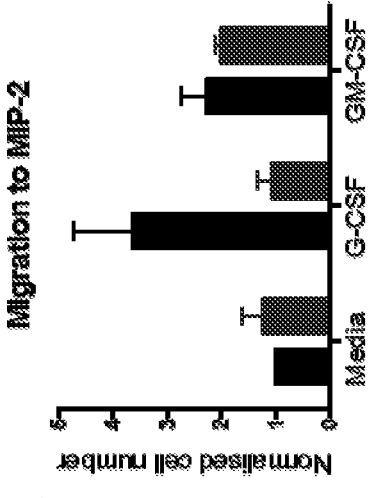

A

B

A

B

A

B

A

B

SEQUENCE LISTING

```
<160> NUMBER OF SEQ ID NOS: 18

<210> SEQ ID NO 1
<211> LENGTH: 319
<212> TYPE: PRT
<213> ORGANISM: artificial
<220> FEATURE:
<223> OTHER INFORMATION: amino acids 25-335 of Homo sapiens G-CSFR
      (hG-CSFR) with a C-terminal polyhistidine tag

<400> SEQUENCE: 1

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly
        35                  40                  45

Gly Arg Gln Gln Arg Leu Ser Asp Gly Thr Gln Glu Ser Ile Ile Thr
    50                  55                  60

Leu Pro His Leu Asn His Thr Gln Ala Phe Leu Ser Cys Ala Leu Asn
65                  70                  75                  80

Trp Gly Asn Ser Leu Gln Ile Leu Asp Gln Val Glu Leu Arg Ala Gly
                85                  90                  95

Tyr Pro Pro Ala Ile Pro His Asn Leu Ser Cys Leu Met Asn Leu Thr
            100                 105                 110

Thr Ser Ser Leu Ile Cys Gln Trp Glu Pro Gly Pro Glu Thr His Leu
            115                 120                 125

Pro Thr Ser Phe Thr Leu Lys Ser Phe Lys Ser Arg Gly Asn Cys Gln
        130                 135                 140

Thr Gln Gly Asp Ser Ile Leu Asp Cys Val Pro Lys Asp Gly Gln Ser
145                 150                 155                 160

His Cys Ser Ile Pro Arg Lys His Leu Leu Leu Tyr Gln Asn Met Gly
                165                 170                 175

Ile Trp Val Gln Ala Glu Asn Ala Leu Gly Thr Ser Met Ser Pro Gln
            180                 185                 190

Leu Cys Leu Asp Pro Met Asp Val Val Lys Leu Glu Pro Pro Met Leu
        195                 200                 205

Arg Thr Met Asp Pro Ser Pro Glu Ala Ala Pro Pro Gln Ala Gly Cys
    210                 215                 220

Leu Gln Leu Ser Trp Glu Pro Trp Gln Pro Gly Leu His Ile Asn Gln
225                 230                 235                 240
```

```
Lys Cys Glu Leu Arg His Lys Pro Gln Arg Gly Glu Ala Ser Trp Ala
                245                 250                 255

Leu Val Gly Pro Leu Pro Leu Glu Ala Leu Gln Tyr Glu Leu Cys Gly
            260                 265                 270

Leu Leu Pro Ala Thr Ala Tyr Thr Leu Gln Ile Arg Cys Ile Arg Trp
            275                 280                 285

Pro Leu Pro Gly His Trp Ser Asp Trp Ser Pro Ser Leu Glu Leu Arg
        290                 295                 300

Thr Thr Glu Arg Ala Pro Thr His His His His His His His His
305                 310                 315
```

<210> SEQ ID NO 2
<211> LENGTH: 118
<212> TYPE: PRT
<213> ORGANISM: artificial
<220> FEATURE:
<223> OTHER INFORMATION: VH of C1.2

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
            35                  40                  45

Ser Ser Ile Ser Ser Ser Gly Gly Val Thr Pro Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Met Leu Gly Glu Leu Gly Trp Phe Asp Pro Trp Gly Gln Gly Thr
            100                 105                 110

Leu Val Thr Val Ser Ser
        115
```

<210> SEQ ID NO 3
<211> LENGTH: 107
<212> TYPE: PRT
<213> ORGANISM: artificial
<220> FEATURE:
<223> OTHER INFORMATION: VL of C1.2

<400> SEQUENCE: 3

```
Asp Ile Gln Met Thr Gln Ser Pro Ser Ala Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
            35                  40                  45

Tyr Tyr Ala Ser Asn Leu Gln Asn Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Ser Tyr Ser Thr Pro Leu
                85                  90                  95

Thr Phe Gly Gly Gly Thr Asn Val Glu Ile Arg
            100                 105
```

-continued

```
<210> SEQ ID NO 4
<211> LENGTH: 118
<212> TYPE: PRT
<213> ORGANISM: artificial
<220> FEATURE:
<223> OTHER INFORMATION: VH of C1.2G

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser
        115

<210> SEQ ID NO 5
<211> LENGTH: 107
<212> TYPE: PRT
<213> ORGANISM: artificial
<220> FEATURE:
<223> OTHER INFORMATION: VL  of C1.2G

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 6
<211> LENGTH: 5
<212> TYPE: PRT
<213> ORGANISM: artificial
<220> FEATURE:
<223> OTHER INFORMATION: HCDR1 of C1.2

<400> SEQUENCE: 6

Leu Tyr Trp Met Gly
1               5
```

```
<210> SEQ ID NO 7
<211> LENGTH: 17
<212> TYPE: PRT
<213> ORGANISM: artificial
<220> FEATURE:
<223> OTHER INFORMATION: C1.2 HCDR2

<400> SEQUENCE: 7

Ser Ile Ser Ser Ser Gly Gly Val Thr Pro Tyr Ala Asp Ser Val Lys
1               5                   10                  15

Gly

<210> SEQ ID NO 8
<211> LENGTH: 9
<212> TYPE: PRT
<213> ORGANISM: artificial
<220> FEATURE:
<223> OTHER INFORMATION: C1.2 HCDR3

<400> SEQUENCE: 8

Leu Gly Glu Leu Gly Trp Phe Asp Pro
1               5

<210> SEQ ID NO 9
<211> LENGTH: 11
<212> TYPE: PRT
<213> ORGANISM: artificial
<220> FEATURE:
<223> OTHER INFORMATION: C1.2 LCDR1

<400> SEQUENCE: 9

Arg Ala Ser Gln Gly Ile Ser Ser Tyr Leu Asn
1               5                   10

<210> SEQ ID NO 10
<211> LENGTH: 6
<212> TYPE: PRT
<213> ORGANISM: artificial
<220> FEATURE:
<223> OTHER INFORMATION: C1.2 LCDR2

<400> SEQUENCE: 10

Ala Ser Asn Leu Gln Asn
1               5

<210> SEQ ID NO 11
<211> LENGTH: 9
<212> TYPE: PRT
<213> ORGANISM: artificial
<220> FEATURE:
<223> OTHER INFORMATION: C1.2 LCDR3

<400> SEQUENCE: 11

Gln Gln Ser Tyr Ser Thr Pro Leu Thr
1               5

<210> SEQ ID NO 12
<211> LENGTH: 8
<212> TYPE: PRT
<213> ORGANISM: artificial
<220> FEATURE:
<223> OTHER INFORMATION: consensus sequence of HCDR3 of C1.2
<220> FEATURE:
<221> NAME/KEY: VARIANT
<222> LOCATION: (5)..(5)
<223> OTHER INFORMATION: X is an amino acid selected from the group
      consisting of tryptophan, glutamine, methionine, serine,
```

```
         phenylalanine, glutamic acid and histidine
<220> FEATURE:
<221> NAME/KEY: VARIANT
<222> LOCATION: (6)..(6)
<223> OTHER INFORMATION: X iis an amino acid selected from the group
         consisting of phenylalanine, tyrosine, methionine, serine, glycine
         and isoleucine
<220> FEATURE:
<221> NAME/KEY: VARIANT
<222> LOCATION: (7)..(7)
<223> OTHER INFORMATION: X is an amino acid selected from the group
         consisting of aspartic acid, methionine, glutamine, serine,
         leucine, valine, arginine and histidine
<220> FEATURE:
<221> NAME/KEY: VARIANT
<222> LOCATION: (8)..(8)
<223> OTHER INFORMATION: X is an amino acid selected from the group
         consisting of proline gltuamic acid, alanine, leucine,
         phenylalanine, tyronis, threonine, asparagine, aspartic acid,
         serine , glycine, arginine, lysine

<400> SEQUENCE: 12

Leu Gly Glu Leu Xaa Xaa Xaa Xaa
1               5

<210> SEQ ID NO 13
<211> LENGTH: 9
<212> TYPE: PRT
<213> ORGANISM: artificial
<220> FEATURE:
<223> OTHER INFORMATION: consensus sequence of LCDR3 of C1.2
<220> FEATURE:
<221> NAME/KEY: VARIANT
<222> LOCATION: (1)..(1)
<223> OTHER INFORMATION: X is an amino acid selected from the group
         consisting of glutamine, glutamic acid, histidine, alanine or
         serine
<220> FEATURE:
<221> NAME/KEY: VARIANT
<222> LOCATION: (2)..(2)
<223> OTHER INFORMATION: X is an amino acid selected from the group
         consisting of glutamine, valine, phenylalanine, asparagine and
         glutamic acid
<220> FEATURE:
<221> NAME/KEY: VARIANT
<222> LOCATION: (3)..(3)
<223> OTHER INFORMATION: X ian amino acid selected from the group
         consisting of serine or glycine
<220> FEATURE:
<221> NAME/KEY: VARIANT
<222> LOCATION: (4)..(4)
<223> OTHER INFORMATION: X is an amino acid selected from the group
         consisting of tryptophan, methionine, phenylalanine, tyrosine,
         isoleucine and leucine
<220> FEATURE:
<221> NAME/KEY: VARIANT
<222> LOCATION: (5)..(5)
<223> OTHER INFORMATION: X is an amino acid selected from the group
         consisting of glutamic acid, methionine, glutamine, tryptophan,
         serine, valine, asparagine, glycine, alanine, arganine, histidine,
         tyrosine, lysine or threonine
<220> FEATURE:
<221> NAME/KEY: VARIANT
<222> LOCATION: (6)..(6)
<223> OTHER INFORMATION: X is an amino acid selected from the group
         consisting of tyrosine, methionine, isoleucine or threonine
<220> FEATURE:
<221> NAME/KEY: VARIANT
<222> LOCATION: (7)..(7)
<223> OTHER INFORMATION: X is an amino acid selected from the group
         consisting of proline, alanine, histidine, glycine and lysine
<220> FEATURE:
<221> NAME/KEY: VARIANT
<222> LOCATION: (8)..(8)
<223> OTHER INFORMATION: X is an amino acid selected from the group
         consisting of leucine, glutamine, methionine, alanine,
         phenylalanine, isoleucine, lysine, histidine and glycine
```

-continued

```
<220> FEATURE:
<221> NAME/KEY: VARIANT
<222> LOCATION: (9)..(9)
<223> OTHER INFORMATION: X is an amino acid selected from the group
      consisting of threonine, phenylalanine, tyrosine, methionine,
      lysine, serine, histidine, proline, tryptophan, isoleucine,
      glutamine, glycine and valine

<400> SEQUENCE: 13

Xaa Xaa Xaa Xaa Xaa Xaa Xaa Xaa Xaa
1               5

<210> SEQ ID NO 14
<211> LENGTH: 445
<212> TYPE: PRT
<213> ORGANISM: artificial
<220> FEATURE:
<223> OTHER INFORMATION: C1.2G heavy chain IgG4 with S241P mutation

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300
```

-continued

```
Thr Val Leu His Gln Asp Trp Leu Asn Gly Lys Glu Tyr Lys Cys Lys
305             310             315             320

Val Ser Asn Lys Gly Leu Pro Ser Ser Ile Glu Lys Thr Ile Ser Lys
                325             330             335

Ala Lys Gly Gln Pro Arg Glu Pro Gln Val Tyr Thr Leu Pro Pro Ser
            340             345             350

Gln Glu Glu Met Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
            405             410             415

Glu Gly Asn Val Phe Ser Cys Ser Val Met His Glu Ala Leu His Asn
            420             425             430

His Tyr Thr Gln Lys Ser Leu Ser Leu Ser Leu Gly Lys
        435             440             445
```

<210> SEQ ID NO 15
<211> LENGTH: 214
<212> TYPE: PRT
<213> ORGANISM: artificial
<220> FEATURE:
<223> OTHER INFORMATION: C1.2G with kappa light chain

<400> SEQUENCE: 15

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Ser Tyr
            20              25              30

Leu Asn Trp Tyr Gln Gln Lys Pro Gly Lys Ala Pro Lys Leu Leu Ile
        35              40              45

Tyr Tyr Ala Ser Asn Leu Gln Asn Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Leu
            85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```

-continued

```
<210> SEQ ID NO 16
<211> LENGTH: 836
<212> TYPE: PRT
<213> ORGANISM: Homo sapiens

<400> SEQUENCE: 16

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
                20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
        50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
        130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
            165                 170                 175

Cys Val Pro Lys Asp Gly Gln Ser His Cys Cys Ile Pro Arg Lys His
        180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
        210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
            245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
        290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
            325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
```

-continued

```
              370              375              380

Leu Pro Leu Cys Asn Thr Thr Glu Leu Ser Cys Thr Phe His Leu Pro
385              390              395              400

Ser Glu Ala Gln Glu Val Ala Leu Val Ala Tyr Asn Ser Ala Gly Thr
                 405              410              415

Ser Arg Pro Thr Pro Val Val Phe Ser Glu Ser Arg Gly Pro Ala Leu
                 420              425              430

Thr Arg Leu His Ala Met Ala Arg Asp Pro His Ser Leu Trp Val Gly
                 435              440              445

Trp Glu Pro Pro Asn Pro Trp Pro Gln Gly Tyr Val Ile Glu Trp Gly
         450              455              460

Leu Gly Pro Pro Ser Ala Ser Asn Ser Asn Lys Thr Trp Arg Met Glu
465              470              475              480

Gln Asn Gly Arg Ala Thr Gly Phe Leu Leu Lys Glu Asn Ile Arg Pro
                 485              490              495

Phe Gln Leu Tyr Glu Ile Ile Val Thr Pro Leu Tyr Gln Asp Thr Met
                 500              505              510

Gly Pro Ser Gln His Val Tyr Ala Tyr Ser Gln Glu Met Ala Pro Ser
                 515              520              525

His Ala Pro Glu Leu His Leu Lys His Ile Gly Lys Thr Trp Ala Gln
         530              535              540

Leu Glu Trp Val Pro Glu Pro Pro Glu Leu Gly Lys Ser Pro Leu Thr
545              550              555              560

His Tyr Thr Ile Phe Trp Thr Asn Ala Gln Asn Gln Ser Phe Ser Ala
                 565              570              575

Ile Leu Asn Ala Ser Ser Arg Gly Phe Val Leu His Gly Leu Glu Pro
                 580              585              590

Ala Ser Leu Tyr His Ile His Leu Met Ala Ala Ser Gln Ala Gly Ala
                 595              600              605

Thr Asn Ser Thr Val Leu Thr Leu Met Thr Leu Thr Pro Glu Gly Ser
         610              615              620

Glu Leu His Ile Ile Leu Gly Leu Phe Gly Leu Leu Leu Leu Leu Thr
625              630              635              640

Cys Leu Cys Gly Thr Ala Trp Leu Cys Cys Ser Pro Asn Arg Lys Asn
                 645              650              655

Pro Leu Trp Pro Ser Val Pro Asp Pro Ala His Ser Ser Leu Gly Ser
                 660              665              670

Trp Val Pro Thr Ile Met Glu Glu Asp Ala Phe Gln Leu Pro Gly Leu
                 675              680              685

Gly Thr Pro Pro Ile Thr Lys Leu Thr Val Leu Glu Glu Asp Glu Lys
         690              695              700

Lys Pro Val Pro Trp Glu Ser His Asn Ser Ser Glu Thr Cys Gly Leu
705              710              715              720

Pro Thr Leu Val Gln Thr Tyr Val Leu Gln Gly Asp Pro Arg Ala Val
                 725              730              735

Ser Thr Gln Pro Gln Ser Gln Ser Gly Thr Ser Asp Gln Val Leu Tyr
                 740              745              750

Gly Gln Leu Leu Gly Ser Pro Thr Ser Pro Gly Pro Gly His Tyr Leu
                 755              760              765

Arg Cys Asp Ser Thr Gln Pro Leu Leu Ala Gly Leu Thr Pro Ser Pro
         770              775              780

Lys Ser Tyr Glu Asn Leu Trp Phe Gln Ala Ser Pro Leu Gly Thr Leu
785              790              795              800
```

```
Val Thr Pro Ala Pro Ser Gln Glu Asp Asp Cys Val Phe Gly Pro Leu
            805                 810                 815

Leu Asn Phe Pro Leu Leu Gln Gly Ile Arg Val His Gly Met Glu Ala
            820                 825                 830

Leu Gly Ser Phe
        835

<210> SEQ ID NO 17
<211> LENGTH: 319
<212> TYPE: PRT
<213> ORGANISM: artificial
<220> FEATURE:
<223> OTHER INFORMATION: Ig and CRH domains of Macaca fascicularis
      G-CSFR (cynoG-CSFR) with a C-terminal polyhistidine tag

<400> SEQUENCE: 17

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Leu Glu Pro Gln Ile Leu Trp Arg Leu Gly Ala Glu Leu Gln Pro Gly
        35                  40                  45

Gly Arg Gln Gln Arg Leu Ser Asp Gly Ser Gln Gln Ser Thr Ile Thr
    50                  55                  60

Leu Pro His Leu Asn His Thr Arg Ala Phe Leu Ser Cys Ala Leu Asn
65                  70                  75                  80

Trp Gly Asn Ser Leu Gln Ile Leu Asp Gln Val Glu Leu Arg Ala Gly
            85                  90                  95

Tyr Pro Pro Ala Val Pro Arg Asn Leu Ser Cys Leu Met Asn Leu Thr
            100                 105                 110

Thr Ser Ser Leu Ile Cys Gln Trp Glu Pro Gly Pro Glu Thr His Leu
        115                 120                 125

Pro Thr Ser Phe Thr Leu Lys Ser Phe Lys Ser Arg Gly Asn Cys Gln
        130                 135                 140

Thr Gln Gly Asp Ser Ile Met Asp Cys Val Pro Glu Asp Gly Gln Ser
145                 150                 155                 160

His Cys Ser Ile Pro Arg Arg His Leu Leu Leu Tyr Gln Asn Met Gly
            165                 170                 175

Ile Trp Val Gln Ala Glu Asn Ala Leu Gly Thr Ser Met Ser Pro Gln
            180                 185                 190

Leu Cys Leu Glu Pro Met Asp Val Val Lys Leu Glu Pro Pro Met Leu
        195                 200                 205

Arg Thr Met Asp Pro Ser Pro Glu Ala Ala Pro Pro Gln Ala Gly Cys
    210                 215                 220

Leu Gln Leu Ser Trp Glu Pro Trp Gln Pro Ala Leu His Ile Asn Gln
225                 230                 235                 240

Lys Cys Glu Leu Arg His Lys Pro Gln Ser Gly Glu Ala Ser Trp Ala
            245                 250                 255

Leu Val Gly Pro Leu Pro Leu Glu Ala Leu Arg Tyr Glu Leu Cys Gly
            260                 265                 270

Leu Leu Pro Ala Thr Ala Tyr Thr Leu Gln Ile Arg Cys Ile Arg Trp
        275                 280                 285

Pro Leu Pro Gly His Trp Ser Asn Trp Ser Pro Ser Leu Glu Leu Arg
    290                 295                 300

Thr Thr Glu Arg Ala Pro Thr His His His His His His His His
```

```
305              310              315

<210> SEQ ID NO 18
<211> LENGTH: 444
<212> TYPE: PRT
<213> ORGANISM: artificial
<220> FEATURE:
<223> OTHER INFORMATION: C1.2G heavy chain IgG4 with S241P mutation and
      lacking C-terminal lysine residue

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

-continued

```
Gln Glu Glu Met Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
            405             410             415

Glu Gly Asn Val Phe Ser Cys Ser Val Met His Glu Ala Leu His Asn
            420             425             430

His Tyr Thr Gln Lys Ser Leu Ser Leu Ser Leu Gly
        435             440
```

1

METHOD OF TREATING ACUTE RESPIRATORY DISTRESS SYNDROME

RELATED APPLICATION DATA

This application is a national stage filing under 35 U.S.C. § 371 of International Application No. PCT/AU2021/050568, filed on Jun. 7, 2021, which claims the benefit of the filing date of Australian Patent Application No. 2020901843, filed on Jun. 4, 2020, each of which is incorporated herein by reference in its entirety.

SEQUENCE LISTING

The present application is filed together with a Sequence Listing in electronic form. The entire contents of the Sequence Listing are hereby incorporated by reference.

FIELD

The present disclosure relates to methods of treating or preventing acute respiratory distress syndrome (ARDS) in a subject.

BACKGROUND

Acute respiratory distress syndrome (ARDS) is a severe, and often life-threatening complication of several systemic disorders and direct injury to the lungs. It is associated with a high mortality rate, primarily as a consequence of multiple organ failure. ARDS occurs when fluid builds up in the alveoli of the lungs, resulting in less oxygen reaching the bloodstream, which deprives organs of the oxygen they need to function. Symptoms of ARDS include severe shortness of breath, labored and unusually rapid breathing, low blood pressure, and confusion and extreme tiredness, which usually develop within a few hours to a few days after an original disease or trauma.

Despite decades of research and advances in medical technology, ARDS-associated mortality remains high, and no pharmacological therapies effectively improve its clinical course. For example, drug candidates that have failed in large trials include, at least, glucocorticoids, alprostadil, surfactant, ketoconazole, N-acetyleysteine, procysteine, lisofylline, and site-inactivated recombinant factor VIIa. The current standard of care is limited to supportive therapies, for example oxygenation, mechanical ventilation, fluid management, and prone positioning.

Therefore, there remains a need for new interventions for treating and preventing ARDS.

SUMMARY

In producing the present invention, the inventors identified granulocyte colony stimulating factor (G-CSF) signaling as a potential pathway for pharmacological intervention in ARDS. The inventors found that an antibody which binds to G-CSF receptor (G-CSFR) and inhibits G-CSF signaling, successfully reduced several measures of lung inflammation in an animal model of ARDS. These findings provide the basis for methods of treating or preventing ARDS in a subject by administering compounds that inhibit G-CSF signaling.

Accordingly, in an example, the present disclosure provides a method for treating or preventing ARDS in a subject, the method comprising administering a compound that inhibits G-CSF signaling to the subject.

The present disclosure also provides a compound that inhibits G-CSF signaling for use in the treatment or prevention of ARDS in a subject.

The present disclosure also provides use of a compound that inhibits G-CSF signaling in the manufacture of a medicament for the treatment or prevention of ARDS in a subject.

Advantageously, due to their mechanism of action, G-CSF signaling inhibitors can be used in accordance with the methods of the present disclosure to treat or prevent ARDS which is associated with any underlying condition. In some examples, the ARDS is associated with one or more of the following:

a) an infection;

b) inhalation or aspiration of a foreign substance;

c) a physical trauma; and d) an inflammatory disease.

In one example, the ARDS is associated with a viral infection. In one example, the ARDS is associated with a bacterial infection. In one example, the ARDS is associated with a fungal infection. In one example, the ARDS is associated with sepsis.

In one example, the ARDS is associated with a coronavirus infection.

In one example, the ARDS is associated with a severe acute respiratory syndrome coronavirus (SARS-COV) infection. In one example, the ARDS is associated with a SARS-CoV-2 infection. Thus, in some examples, the subject has coronavirus disease 2019 (COVID-19). In particular, severe COVID-19 often results in ARDS. The methods of the present disclosure can be used to treat or prevent ARDS in severe COVID-19 subjects. Accordingly, in some examples, the subject has severe COVID-19.

In some examples, the ARDS is associated with inhalation or aspiration of a foreign substance. For instance, breathing high concentrations of smoke or chemical fumes can result in ARDS, as can aspirating vomit or near-drowning episodes.

In some examples, the ARDS is associated with severe pneumonia. Severe cases of pneumonia usually affect all five lobes of the lungs and can result in ARDS. Thus, in some examples, the subject has interstitial pneumonia.

In some examples, the ARDS is associated with a physical trauma. For example, head, chest and other major injuries can lead to ARDS. Accidents, such as falls or car crashes, can directly damage the lungs or the portion of the brain that controls breathing, thereby leading to ARDS. In some examples, the ARDS is associated with a lung injury. In some examples, the ARDS is associated with a brain injury. In some examples, the ARDS is associated with a burn injury.

In some examples, the ARDS is associated with an inflammatory disease. For instance, pancreatitis can lead to ARDS as can other severe inflammatory diseases. In some examples, the ARDS is associated with a blood transfusion.

In some examples, the subject has ARDS.

In some examples, the subject satisfies the Berlin definition of ARDS. Thus, in some examples, the subject has:

a) an onset of ARDS within 1 week or less of clinical insult or initial respiratory symptoms;

b) an acute hypoxemic respiratory failure, as determined by a ratio of arterial partial pressure of oxygen to fraction of inspired oxygen ($PaO_2/FiO_2$ ratio) of 300 mmHg or less on at least 5 cm of continuous positive airway pressure (CPAP) or positive end expiratory pressure (PEEP), c) bilateral opacities on chest radiographs not fully explained by effusions, consolidation, or atelectasis; and d) respiratory failure not fully explained by cardiac failure or fluid overload.

In some examples of the methods of the disclosure, the ARDS is mild ARDS. In some examples, the ARDS is moderate ARDS. In some examples, the ARDS is severe ARDS. The severity of ARDS can be categorized according to the Berlin definition as follows:

(i) Mild ARDS: $PaO_2/FiO_2$ of 200-300 mmHg on at least 5 cm CPAP or PEEP;

(ii) Moderate ARDS: $PaO_2/FiO_2$ of 100-200 mmHg on at least 5 cm PEEP, and (iii) Severe ARDS: $PaO_2/FiO_2$ of less than or equal to 100 mmHg on at least 5 cm PEEP.

Advantageously the methods of the present disclosure can, in addition to treatment of existing ARDS, be used to prevent the onset of ARDS. Thus, in some examples, the subject does not have ARDS.

In some examples, the subject is at risk of developing ARDS. Methods of identifying subjects at risk of developing ARDS will be known by those skilled in the art and include those described herein.

In some examples, the subject has one or more or all of the following a) a respiratory frequency of greater than 30 breaths per minute;

b) an oxygen saturation ($SpO_2$) of 93% or less on room air;

c) a ratio of arterial partial pressure of oxygen to fraction of inspired oxygen ($PaO_2/TiO_2$) of less than 300 mmHg;

d) a $SpO_2/FiO_2$ ratio of less than 218; and e) radiographic lung infiltrates in an amount of greater than 50%.

The above criteria can, in some examples, be used to assess if a subject is at risk of developing ARDS.

In some examples, the subject is not receiving high flow oxygen therapy (HFOT) or non-invasive ventilation (NIV) at the time of administering the compound that inhibits G-CSF signaling.

In some examples, the compound that inhibits G-CSF signaling is administered in an amount sufficient to reduce the severity of or prevent onset of one or more symptoms of ARDS.

In one example, the compound that inhibits G-CSF signaling is administered in an amount sufficient to prevent endotracheal intubation or death prior to endotracheal intubation. Endotracheal intubation is a process of inserting a tube, i.e., an endotracheal tube, through the mouth of the subject and into the airways so that the subject can be placed on a mechanical ventilator. Thus, the methods of the present disclosure additionally provide a method of preventing or reducing mechanical ventilation of a subject with ARDS, the method comprising administering a compound that inhibits G-CSF signaling to the subject.

In some examples, the compound that inhibits G-CSF signaling is administered in an amount sufficient to achieve one or more or all of the following:

a) increase the subject's days alive and ventilator free;

b) decrease the subject's hospital length of stay (LOS);

c) improve the subject's clinical status as assessed on an 8-point National Institute of Allergy and Infectious Disease (NIAID) ordinal scale;

d) reduce or prevent use of continuous positive airway pressure (CPAP) or bilevel positive airway pressure (BiPAP);

e) reduce or prevent use of high-flow nasal cannula (HFNC);

f) reduce or prevent use of extracorporeal membrane oxygenation (ECMO); and g) reduce or prevent an increase in the subject's Sequential Organ Failure Assessment (SOFA) Score.

In some examples, the compound that inhibits G-CSF signaling is administered in an amount sufficient to reduce, or prevent an increase in, inflammation in the subject's lungs. In one example, the compound that inhibits G-CSF signaling is administered in an amount sufficient to enhance lung function.

In some examples the compound that inhibits G-CSF signaling is administered in an amount sufficient to reduce, or prevent an increase in, total cell counts and/or total protein in bronchoalveolar lavage fluid (BALF) of the subject. In some examples, the compound that inhibits G-CSF signaling is administered in an amount sufficient to reduce, or prevent an increase in, the level of neutrophils present in BALF of the subject.

In some examples, the compound that inhibits G-CSF signaling is administered in an amount sufficient to reduce, or prevent an increase in, the level of neutrophil elastase and/or myeloperoxidase activity in BALF of the subject.

In some examples, the compound that inhibits G-CSF signaling is administered in an amount sufficient to reduce, or prevent an increase in, the levels of any one or more or all of the following: G-CSF, plasminogen activator inhibitor-1 (PAI-1), D-dimer, neutrophil elastase, soluble receptor for AGE (sRAGE), interferon gamma (IFN-$\gamma$), interleukin 1$\beta$ (IL-1$\beta$), IL-2, IL-4, IL-6, IL-8, IL-10, IL-12p70, IL-13, and tumor necrosis factor alpha (TNF-$\alpha$). These biomarkers can be used to assess the efficacy of treatment or to assist in identifying a subject at risk of developing ARDS.

In some examples, the levels of the above proteins are reduced, or prevented from increasing, in the subject's lungs. In some examples, the levels of the above proteins are reduced, or prevented from increasing, in the subject's blood.

Methods for assessing each of the foregoing are known in the art and/or are described herein. Furthermore, a person skilled in the art will appreciate that the terms "reduce" and "prevent an increase in" are used herein to refer to a lower amount of any of the items listed above, relative to either the amount in the subject prior to administration of the compound that inhibits G-CSF signaling, or relative to the amount in a corresponding control subject. For instance, the control subject may be a subject who receives a placebo and/or a standard of care therapy, rather than the compound that inhibits G-CSF signaling.

In some examples, the reduction in the amount of the item listed above, or prevention of an increase thereof, is assessed within 30 days of first administration of the compound that inhibits G-CSF signaling. In some examples, the reduction in the amount of the item listed above, or prevention of an increase thereof, is assessed 1, 2, 3, 4, 5, 6, 7, 8, 9, 10, 14, 17, 21, 24 or 28 days after first administration of the compound that inhibits G-CSF signaling.

Suitably, inhibition of G-CSF signaling can be achieved by blocking G-CSF (e.g., using a compound that binds to G-CSF) or by blocking G-CSFR (e.g., using a compound that binds to G-CSFR). In this regard, it has been shown that antibodies binding to G-CSF and antibodies binding to G-CSFR are both effective in inhibiting G-CSF signaling and reducing disease severity in a mouse model of arthritis (Campbell et al., 2016 *J Immunol* 197: 4392-4402) Thus, in some examples, the compound that inhibits G-CSF signaling binds to G-CSF or to G-CSF receptor (G-CSFR). In one example, the compound that inhibits G-CSF signaling binds to G-CSF. In one example, the compound that inhibits G-CSF signaling binds to G-CSF receptor (G-CSFR).

In one example, the compound that inhibits G-CSF signaling is a protein.

In one example, the compound that inhibits G-CSF signaling is a protein comprising an antigen binding site that binds to or specifically binds to G-CSFR and neutralizes G-CSF signaling. Reference herein to a protein or antibody that "binds to" G-CSFR provides literal support for a protein or antibody that "binds specifically to" G-CSFR.

In one example, the compound that inhibits G-CSF signaling is a protein comprising an antibody variable region that binds to or specifically binds to G-CSF and neutralizes G-CSF signaling.

In some examples, the compound that inhibits G-CSF signaling is a protein comprising a Fv. In some examples, the protein comprises;
(i) a single chain Fv fragment (scFv);
(ii) a dimeric scFv (di-scFv); or
(iii) a diabody;
(iv) a triabody;
(v) a tetrabody;
(vi) a Fab;
(vii) a F(ab')$_2$;
(viii) a Fv;
(ix) one of (i) to (viii) linked to a constant region of an antibody. Fc or a heavy chain constant domain (C$_H$) 2 and/or C$_H$3;
(x) one of (i) to (viii) linked to albumin or a functional fragment or variants thereof or a protein that binds to albumin; or
(xi) an antibody.

In some examples, the protein is selected from the group consisting of:
(i) a single chain Fv fragment (scFv);
(ii) a dimeric scFv (di-scFv); or
(iii) a diabody;
(iv) a triabody;
(v) a tetrabody;
(vi) a Fab;
(vii) a F(ab')$_2$;
(viii) a Fv;
(ix) one of (i) to (viii) linked to a constant region of an antibody, Fc or a heavy chain constant domain (C$_H$) 2 and/or C$_H$$^3$;
(x) one of (i) to (viii) linked to albumin, functional fragments or variants thereof or a protein (e.g., antibody or antigen binding fragment thereof) that binds to albumin; or
(xi) an antibody.

In one example, the protein comprises an Fc region.

In one example, the protein comprises one or more amino acid substitutions that increase the half-life of the protein. In one example, the antibody comprises a Fc region comprising one or more amino acid substitutions that increase the affinity of the Fc region for the neonatal Fc receptor (FcRn).

In one example, the protein is an antibody. Exemplary antibodies are described in WO2012/171057.

In one example, the protein binds to hG-CSFR expressed on the surface of a cell at an affinity of at least about 5 nM. In one example, the protein binds to hG-CSFR expressed on the surface of a cell at an affinity of at least about 4 nM. In one example, the protein binds to hG-CSFR expressed on the surface of a cell at an affinity of at least about 3 nM. In one example, the protein binds to hG-CSFR expressed on the surface of a cell at an affinity of at least about 2 nM. In one example, the protein binds to hG-CSFR expressed on the surface of a cell at an affinity of at least about 1 nM.

In one example, the protein inhibits G-CSF-induced proliferation of a BaF3 cell expressing hG-CSFR with an IC50 of at least about 5 nM. In one example, the protein inhibits G-CSF-induced proliferation of a BaF3 cell expressing hG-CSFR with an IC50 of at least about 4 nM. In one example, the protein inhibits G-CSF-induced proliferation of a BaF3 cell expressing hG-CSFR with an IC50 of at least about 3 nM.

In one example, the protein inhibits G-CSF-induced proliferation of a BaF3 cell expressing hG-CSFR with an IC50 of at least about 2 nM. In one example, the protein inhibits G-CSF-induced proliferation of a BaF3 cell expressing hG-CSFR with an IC50 of at least about 1 nM. In one example, the protein inhibits G-CSF-induced proliferation of a BaF3 cell expressing hG-CSFR with an IC50 of at least about 0.5 nM.

In one example, the protein or antibody is chimeric, de-immunized, humanized, human or primatized. In one example, the protein or antibody is human.

In one example, the protein comprises an antibody variable region that competitively inhibits the binding of antibody C1.2G comprising a heavy chain variable region (V$_H$) comprising a sequence set forth in SEQ ID NO: 4 and a light chain variable region (V$_L$) comprising a sequence set forth in SEQ ID NO: 5 to G-CSFR.

In one example, the protein binds to an epitope comprising residues within one or two or three or four regions selected from 111-115, 170-176, 218-234 and/or 286-300 of SEQ ID NO: 1.

In one example, the protein comprises an antibody variable region comprising a heavy chain variable region (V$_H$) comprising an amino acid sequence set forth in SEQ ID NO: 4 and a light chain variable region (V$_L$) comprising an amino acid sequence set forth in SEQ ID NO: 5.

In one example, the protein comprises an antibody variable region comprising a VH comprising an amino acid sequence set forth in SEQ ID NO: 2 and a VL comprising an amino acid sequence set forth in SEQ ID NO: 3.

In one example, the protein comprises an antibody variable region comprising a VH comprising three CDRs of a VH comprising an amino acid sequence set forth in SEQ ID NO: 4 and a VL comprising three CDRs of a VL comprising an amino acid sequence set forth in SEQ ID NO: 5.

In one example, the protein comprises an antibody variable region comprising a VH comprising three CDRs of a VH comprising an amino acid sequence set forth in SEQ ID NO: 2 and a VL comprising three CDRs of a VL comprising an amino acid sequence set forth in SEQ ID NO: 3.

In one example, the protein comprises:
(i) a heavy chain comprising an amino acid sequence set forth in SEQ ID NO: 14 and a light chain comprising a sequence set forth in SEQ ID NO: 15; or
(ii) a heavy chain comprising an amino acid sequence set forth in SEQ ID NO: 16 and a light chain comprising a sequence set forth in SEQ ID NO: 15.

In one example, the protein comprises:
(i) a heavy chain comprising a sequence set forth in SEQ ID NO: 14 or 18 and a light chain comprising an amino acid sequence set forth in SEQ ID NO: 15; or

(ii) one heavy chain comprising an amino acid sequence set forth in SEQ ID NO: 14 and one heavy chain comprising an amino acid sequence set forth in SEQ ID NO: 18 and two light chains comprising an amino acid sequence set forth in SEQ ID NO: 15.

In some examples, the protein is a fusion protein. Thus, in some examples, the protein comprises an antigen binding site which binds to G-CSF or G-CSFR and comprises another amino acid sequence.

In some examples, the fusion protein comprises
a) serum albumin or a variant thereof; or
b) a soluble complement receptor or a variant thereof.

Exemplary amino acid sequences for serum albumin and variants thereof are provided in WO2019/075519. Exemplary amino acid sequences for soluble complement receptors and variants thereof are provided in WO2019/075519 and WO2019/218009.

In some examples, the soluble complement receptor is a soluble complement receptor type 1 (sCR1).

In some examples, the fusion protein comprises a complement inhibitor. In some examples, the complement inhibitor is a complement component 1 (C1) inhibitor. In one example, the C1 inhibitor is C1-INH (also known as "C1 esterase inhibitor") or a functional variant or fragment thereof.

In some examples, the protein comprises an antigen binding site that binds to G-CSF or G-CSFR and another antigen binding site that binds to a different antigen. Thus, in some examples, the protein is a multispecific protein (e.g., a multispecific antibody). In some examples, the protein is a bispecific protein.

In some examples, the other antigen binding site binds to an interleukin or a receptor thereof. In some examples, the other antigen binding site binds to a complement protein.

In some examples, the other antigen binding site binds to interleukin 6 (IL-6) or IL-6 receptor (IL-6R). In some examples, the other antigen binding site binds to interleukin 3 (IL-3) or IL-3 receptor (IL-3R). In some examples, the other antigen binding site binds to interleukin 5 (IL-5) or IL-5 receptor (IL-5R). In some examples, the other antigen binding site binds to interleukin 4 (IL-4) or IL-4 receptor (IL-4R). In some examples, the other antigen binding site binds to interleukin 13 (IL-13) or IL-13 receptor (IL-13R). In some examples, the other antigen binding site binds to granulocyte-macrophage colony-stimulating factor (GM-CSF) or GM-CSF receptor (GM-CSFR). In some examples, the other antigen binding site binds to cytokine receptor common subunit beta (CSF2RB). In some examples, the other antigen binding site binds to C1. In some examples, the other antigen binding site binds to complement component 2 (C2). In some examples, the other antigen binding site binds to a blood coagulation factor. In some examples, the other antigen binding site binds to coagulation factor XII (FXII).

In work leading up to the present disclosure, the inventors sought to identify dosages of G-CSF signaling inhibitors that were able to reduce the number of circulating neutrophils in a subject without inducing severe neutropenia or without inducing severe neutropenia for an extended period. By reducing the number of circulating neutrophils, the inventors are able to reduce lung inflammation in order treat or prevent ARDS. Thus, in some examples, the compound that inhibits G-CSF signaling is administered in an amount sufficient to reduce circulating neutrophils in the subject without causing sustained grade 3 or grade 4 neutropenia for greater than seven consecutive days.

In one example, administration of the compound does not cause grade 3 neutropenia or grade 4 neutropenia (or severe neutropenia) in the subject for greater than three consecutive days.

In one example, administration of the compound does not cause grade 3 neutropenia or grade 4 neutropenia (or severe neutropenia) in the subject for greater than four or five or six consecutive days.

In one example, administration of the compound does not cause grade 3 neutropenia or grade 4 neutropenia (or severe neutropenia) in the subject for greater than seven consecutive days.

In some examples, the compound that inhibits G-CSF signaling is administered in an amount sufficient to reduce circulating neutrophils in the subject without causing sustained grade 2 or grade 3 or grade 4 neutropenia for greater than two consecutive days.

In some examples, the compound that inhibits G-CSF signaling is administered in an amount sufficient to reduce circulating neutrophils in the subject without causing grade 4 neutropenia for greater than 12 hours. In some examples, the compound that inhibits G-CSF signaling is administered in an amount sufficient to reduce circulating neutrophils in the subject without causing grade 3 neutropenia for greater than 12 hours. In some examples, the compound that inhibits G-CSF signaling is administered in an amount sufficient to reduce circulating neutrophils in the subject without causing grade 2 neutropenia for greater than 12 hours.

In some examples, the compound that inhibits G-CSF signaling is administered in an amount sufficient to reduce circulating neutrophils in the subject without causing grade 4 neutropenia. In some examples, the compound that inhibits G-CSF signaling is administered in an amount sufficient to reduce circulating neutrophils in the subject without causing grade 3 neutropenia. In some examples, the compound that inhibits G-CSF signaling is administered in an amount sufficient to reduce circulating neutrophils in the subject without causing grade 2 neutropenia.

The present inventors have identified specific dosages of proteins comprising antigen binding sites that bind to G-CSF or G-CSFR which are safe and effective at reducing circulating neutrophils in a subject.

In one example, the protein is administered at a dose of between 0.1 mg/kg and 1 mg/kg. In an example, the protein is administered at a dose of between 0.1 mg/kg and 0.9 mg/kg, for example, between 0.1 mg/kg and 0.8 mg/kg, for example between 0.1 mg/kg and 0.6 mg/kg.

As used herein, the term "between" includes the values recited at each end of the range specified.

In one example, the protein is administered at a dose of between 0.1 mg/kg and 0.8 mg/kg.

In one example, the protein is administered at a dose of between 0.3 mg/kg and 0.6 mg/kg.

In one example, the protein is administered at a dose of between of 0.1 mg/kg to 0.6 mg/kg.

In one example, the protein is administered at a dose of 0.1 mg/kg or 0.3 mg/kg or 0.6 mg/kg.

In one example, the protein is administered at a dose of about 0.1 mg/kg.

In one example, the protein is administered at a dose of about 0.2 mg/kg.

In one example, the protein is administered at a dose of about 0.3 mg/kg.

In one example, the protein is administered at a dose of about 0.4 mg/kg.

In one example, the protein is administered at a dose of about 0.5 mg/kg.

In one example, the protein is administered at a dose of about 0.6 mg/kg.

In one example, the protein is administered at a dose of about 0.7 mg/kg.

In one example, the protein is administered at a dose of about 0.8 mg/kg.

In some examples, the protein is administered multiple times. Where multiple doses are administered, any of the above (and other) doses can be combined.

In some examples, the protein is administered multiple times to the subject, wherein the protein is administered once every 2 to 5 days. In some examples, subsequent doses are separated by 2 to 5 days. The period of time separating each subsequent dose can be the same or different.

In some examples, the first dose of the protein is higher than subsequent doses. In one example, one or more loading doses of the compound is administered followed by one or more maintenance doses. Generally, the loading doses will be higher or administered with a shorter time period between them than the maintenance doses.

In some examples, at least two doses of the protein are administered to the subject.

In some examples, the methods described herein comprise administering the protein to the subject in a first dose of 0.8 mg/kg.

In some examples, the methods described herein comprise administering the protein to the subject in a first dose of 0.7 mg/kg.

In some examples, the methods described herein comprise administering the protein to the subject in a first dose of 0.6 mg/kg.

In some examples, the methods described herein comprise administering the protein to the subject in a first dose of 0.5 mg/kg.

In some examples, the methods described herein comprise administering the protein to the subject in a first dose of 0.4 mg/kg.

In some examples, the methods described herein comprise administering the protein to the subject in a first dose of 0.3 mg/kg.

In some examples, the methods described herein comprise administering the protein to the subject in a first dose of 0.2 mg/kg.

In some examples, the methods described herein comprise administering the protein to the subject in a first dose of 0.1 mg/kg.

In some examples, the methods described herein comprise administering the protein to the subject in a first dose of 0.05 mg/kg.

In some examples, the methods described herein comprise administering a further one or more doses subsequent to the first dose.

In some examples, the methods described herein comprise administering a further one or more doses of 0.2 mg/kg to the subject.

In some examples, the methods described herein comprise administering a further one or more doses of 0.1 mg/kg to the subject.

In some examples, the methods described herein comprise administering a further one or more doses of 0.05 mg/kg to the subject.

In some examples, the methods described herein comprise administering the protein to the subject in a first dose of 0.8 mg/kg, and a further one or more doses of 0.2 mg/kg.

In some examples, the methods described herein comprise administering the protein to the subject in a first dose of 0.7 mg/kg, and a further one or more doses of 0.2 mg/kg.

In some examples, the methods described herein comprise administering the protein to the subject in a first dose of 0.6 mg/kg, and a further one or more doses of 0.2 mg/kg.

In some examples, the methods described herein comprise administering the protein to the subject in a first dose of 0.5 mg/kg, and a further one or more doses of 0.2 mg/kg.

In some examples, the methods described herein comprise administering the protein to the subject in a first dose of 0.4 mg/kg, and a further one or more doses of 0.2 mg/kg.

In some examples, the methods described herein comprise administering the protein to the subject in a first dose of 0.3 mg/kg, and a further one or more doses of 0.2 mg/kg.

In some examples, the methods described herein comprise administering the protein to the subject in a first dose of 0.2 mg/kg, and a further one or more doses of 0.2 mg/kg.

In some examples, the methods described herein comprise administering the protein to the subject in a first dose of 0.1 mg/kg, and a further one or more doses of 0.2 mg/kg.

In some examples, the methods described herein comprise administering the protein to the subject in a first dose of 0.8 mg/kg, and a further one or more doses of 0.1 mg/kg.

In some examples, the methods described herein comprise administering the protein to the subject in a first dose of 0.7 mg/kg, and a further one or more doses of 0.1 mg/kg.

In some examples, the methods described herein comprise administering the protein to the subject in a first dose of 0.6 mg/kg, and a further one or more doses of 0.1 mg/kg.

In some examples, the methods described herein comprise administering the protein to the subject in a first dose of 0.5 mg/kg, and a further one or more doses of 0.1 mg/kg.

In some examples, the methods described herein comprise administering the protein to the subject in a first dose of 0.4 mg/kg, and a further one or more doses of 0.1 mg/kg.

In some examples, the methods described herein comprise administering the protein to the subject in a first dose of 0.3 mg/kg, and a further one or more doses of 0.1 mg/kg.

In some examples, the methods described herein comprise administering the protein to the subject in a first dose of 0.2 mg/kg, and a further one or more doses of 0.1 mg/kg.

In some examples, the methods described herein comprise administering the protein to the subject in a first dose of 0.1 mg/kg, and a further one or more doses of 0.1 mg/kg.

In some examples, the methods described herein comprise administering the protein to the subject in a first dose of 0.8 mg/kg, and a further one or more doses of 0.05 mg/kg.

In some examples, the methods described herein comprise administering the protein to the subject in a first dose of 0.7 mg/kg, and a further one or more doses of 0.05 mg/kg.

In some examples, the methods described herein comprise administering the protein to the subject in a first dose of 0.6 mg/kg, and a further one or more doses of 0.05 mg/kg.

In some examples, the methods described herein comprise administering the protein to the subject in a first dose of 0.5 mg/kg, and a further one or more doses of 0.05 mg/kg.

In some examples, the methods described herein comprise administering the protein to the subject in a first dose of 0.4 mg/kg, and a further one or more doses of 0.05 mg/kg.

In some examples, the methods described herein comprise administering the protein to the subject in a first dose of 0.3 mg/kg, and a further one or more doses of 0.05 mg/kg.

In some examples, the methods described herein comprise administering the protein to the subject in a first dose of 0.2 mg/kg, and a further one or more doses of 0.05 mg/kg.

In some examples, the methods described herein comprise administering the protein to the subject in a first dose of 0.1 mg/kg, and a further one or more doses of 0.05 mg/kg.

In some examples, the methods described herein comprise administering the protein to the subject in a first dose of between 0.1 mg/kg and 0.4 mg/kg, and a further one or more doses of between 0.05 mg/kg and 0.2 mg/kg.

In some examples, the methods described herein comprise administering the protein to the subject in a first dose of between 0.2 mg/kg and 0.4 mg/kg, and a further one or more doses of between 0.05 mg/kg and 0.2 mg/kg.

In some examples, the methods described herein comprise administering the protein to the subject in a first dose of between 0.1 mg/kg and 0.3 mg/kg, and a further one or more doses of between 0.05 mg/kg and 0.2 mg/kg.

In some examples, the methods described herein comprise administering the protein to the subject in a first dose of 0.3 mg/kg, and a further one or more doses of 0.1 mg/kg.

In some examples, the second dose is two to four days after the first dose. In some examples, the second dose is three days after the first dose.

In some examples, at least three doses of the protein are administered to the subject.

In some examples, the methods described herein comprise administering the protein to the subject in a first dose of between 0.1 mg/kg and 0.4 mg/kg, a second dose of between 0.05 mg/kg and 0.2 mg/kg, and a third dose of between 0.05 mg/kg and 0.2 mg/kg.

In some examples, the methods described herein comprise administering the protein to the subject in a first dose of between 0.2 mg/kg and 0.4 mg/kg, a second dose of between 0.05 mg/kg and 0.2 mg/kg, and a third dose of between 0.05 mg/kg and 0.2 mg/kg.

In some examples, the methods described herein comprise administering the protein to the subject in a first dose of between 0.1 mg/kg and 0.3 mg/kg, a second dose of between 0.05 mg/kg and 0.2 mg/kg, and a third dose of between 0.05 mg/kg and 0.2 mg/kg.

In some examples, the methods described herein comprise administering the protein to the subject in a first dose of 0.3 mg/kg, a second dose of 0.1 mg/kg, and a third dose of 0.1 mg/kg.

In some examples, the second dose is two to four days after the first dose and the third dose is three to five days after the second dose.

In some examples, the second dose is three days after the first dose and the third dose is four days after the second dose.

In an example, a first dose of 0.3 mg/kg is administered on day 1, a second dose of 0.1 mg/kg is administered on day 4, and a third dose of 0.1 mg/kg is administered on day 8.

In some examples, the compound that inhibits G-CSF signaling is administered systemically. In some examples, the compound that inhibits G-CSF signaling is administered locally.

In some examples, the compound that inhibits G-CSF signaling is administered intravenously.

In some examples, the compound that inhibits G-CSF signaling is administered subcutaneously.

In one example, the compound that inhibits G-CSF signaling is administered in combination with another therapy.

In one example, the other therapy comprises administration of an anti-inflammatory compound. In one example, the other therapy comprises administration of an immunomodulator or an immunosuppressant.

In some examples, the other therapy comprises administration of a protein comprising an antigen binding site. In some examples, the protein comprising an antigen binding site is an antibody.

In some examples, the other therapy comprises administration of a compound that inhibits interleukin signaling.

In some examples, the other therapy comprises administration of a compound that inhibits IL-3, IL-5, and/or GM-CSF signaling.

In one example, the compound that inhibits IL-3, IL-5, and/or GM-CSF signaling binds to IL-3R, IL-5R, and/or GM-CSFR. In one example, the compound that inhibits IL-3, IL-5, and/or GM-CSF signaling binds to CSF2RB. In one example, the compound that inhibits IL-3, IL-5, and/or GM-CSF signaling is an antibody. In one example, the compound that inhibits IL-3, IL-5, and/or GM-CSF signaling is an antibody described in WO 2017/088028. In one example, the compound that inhibits IL-3, IL-5, and/or GM-CSF signaling is CSL311. In some examples, the compound that inhibits IL-3, IL-5, and/or GM-CSF signaling is an antibody comprising the CDRs of CSL311. In some examples, the compound that inhibits IL-3. IL-5, and/or GM-CSF signaling is an antibody comprising the $V_H$ and $V_L$ of CSL311.

In some examples, the other therapy comprises administration of a compound that inhibits IL-4 and/or IL-13 signaling. In some examples, the other therapy comprises administration of a compound that binds to IL-13R. In some examples, the compound that binds to IL-13R is an antibody. In some examples, the compound that binds to IL-13R is CSL334 (also known as ASLAN004). In some examples, the compound that binds to IL-13R is an antibody comprising the CDRs of CSL334. In some examples, the compound that binds to IL-13R is an antibody comprising the $V_H$ and $V_L$ of CSL334.

In some examples, the other therapy comprises administration of a compound that binds to IL-3R. In some examples, the compound that binds to IL-3R is an antibody. In some examples, the compound that binds to IL-3R is an antibody described in WO 2014/438819. In some examples, the compound that binds to IL-3R is CSL362. In some examples, the compound that binds to IL-3R is an antibody comprising the CDRs of CSL362. In some examples, the compound that binds to IL-3R is an antibody comprising the $V_H$ and $V_L$ of CSL362.

In some examples, the other therapy comprises administration of a complement inhibitor.

In some examples, the complement inhibitor is a C1 inhibitor. In some examples, the complement inhibitor binds to C1. In one example, the C1 inhibitor is C1-INH or a functional variant or fragment thereof. For example, C1-INH may be plasma-derived or recombinantly produced.

In some examples, the complement inhibitor is a C2 inhibitor. In some examples, the complement inhibitor binds to C2. In some examples, the complement inhibitor that binds to C2 is an antibody.

In one example, the complement inhibitor binds to complement component C4b and/or complement component C3b. In one example the complement inhibitor comprises an extracellular domain of complement receptor type 1 (CR1). In one example, the C1 inhibitor is soluble complement receptor type 1 (sCR1) or a functional fragment or variant thereof.

In some examples, the other therapy comprises administering a blood coagulation factor inhibitor. In some examples, the blood coagulation factor inhibitor is a FXII inhibitor. In some examples, the blood coagulation factor inhibitor binds to FXII. In some examples, the blood coagulation factor inhibitor is CSL312 (garadacimab). In some examples, the blood coagulation factor inhibitor is an antibody comprising the CDRs of CSL312. In some examples, the blood coagulation factor inhibitor is an antibody comprising the $V_H$ and $V_L$ of CSL312.

In some examples, the compound that inhibits G-CSF signaling is administered in combination with a cell. In some examples, the cell is a stem cell, such as a mesenchymal stem cell.

In some examples, the compound that inhibits G-CSF signaling is administered in combination with a gene therapy.

In one example, the compound that inhibits G-CSF signaling is administered simultaneously with the other therapy. In one example, the compound that inhibits G-CSF signaling is administered before the other therapy. In one example, the compound that inhibits G-CSF signaling is administered after the other therapy.

In some examples, the compound that inhibits G-CSF signaling is administered in combination with a standard of care therapy. The standard of care therapy may be a standard of care therapy for the underlying cause of ARDS, or it may be a standard of care therapy for ARDS itself.

In some examples, the standard of care therapy comprises one or more or all of the following:

a) prone positioning;
b) fluid management;
c) administration of nitric oxide;
d) administration of a neuromuscular blocking agent;
e) artificial ventilation;
f) extracorporeal membrane oxygenation; and
g) administration of an antiviral agent or antibiotic.

In one example, the standard of care therapy comprises administration of an anti-viral. In one example, the standard of care therapy comprises administration of remdesivir. In one example, the standard of care therapy comprises administration of one or more of the following:

a) hydroxychloroquine;
b) chloroquine;
c) lopinavir;
d) ritonavir;
e) azithromycin;
f) interferon beta;
S) anakinra;
h) tocilizumab;
i) sarilumab;
j) dexamethasone;
k) aspirin;
l) losartan;
m) simvastatin; and
n) baricitinib.

In one example, the subject is a human. In one example, the subject is an adult, for example over 18 years of age. In one example, the subject is a child, for example less than 18 years of age. In one example, the subject is between 18 and 90 years of age. In one example, the subject is between 50 and 80 years of age.

In one example, the subject does not have chronic obstructive pulmonary disease (COPD). In one example, the subject does not have asthma.

In one example, the methods described herein further comprise identifying the subject as being responsive to treatment with a compound that inhibits G-CSF signaling. In one example, identifying the subject as being responsive to treatment with a compound that inhibits G-CSF signaling comprises determining that the subject has increased levels of neutrophils in their lungs (e.g., in sputum). In one example, identifying the subject as being responsive to treatment with a compound that inhibits G-CSF signaling comprises determining that the subject has increased expression of G-CSF and/or G-CSFR (e.g., in blood or bronchial biopsy tissue).

Key to Sequence Listing

SEQ ID NO: 1—amino acids 25-335 of *Homo sapiens* G-CSFR (hG-CSFR) with a C-terminal polyhistidine tag SEQ ID NO: 2—$V_H$ of C1.2

SEQ ID NO: 3—$V_L$ of C1.2

SEQ ID NO: 4—$V_H$ of C1.2G

SEQ ID NO: 5—$V_L$ of C12G

SEQ ID NO: 6—HCDR1 of C1.2

SEQ ID NO: 7—HCDR2 of C1.2

SEQ ID NO: 8—HCDR3 of C1.2

SEQ ID NO: 9—LCDR1 of C1.2

SEQ ID NO: 10—LCDR2 of C1.2

SEQ ID NO: 11—LCDR3 of C1.2

SEQ ID NO: 12—consensus sequence of HCDR3 of C1.2

SEQ ID NO: 13—consensus sequence of LCDR3 of C1.2

SEQ ID NO: 14—Heavy chain of C1.2G with stabilized IgG4 constant region

SEQ ID NO: 15—Light chain of C1.2G with kappa constant region

SEQ ID NO: 16—sequence of exemplary h-G-CSFR

SEQ ID NO: 17—polypeptide comprising Ig and CRH domains of *Macaca fascicularis* G-CSFR (cynoG-CSFR) with a C-terminal polyhistidine tag SEQ ID NO: 18—Heavy chain of C1.2G with stabilized IgG4 constant region and lacking C-terminal lysine.

BRIEF DESCRIPTION OF THE DRAWINGS

FIG. 3 is a heatmap indicating absolute neutrophil count (ANC) according to neutropenia toxicity grade (i.e., Grades 1, 2, 3, and 4) in healthy subjects administered a single dose of 0.1, 0.3, 0.6, 0.8, and 1.0 mg/kg CSL324, as described in Example 1.

FIG. 4 is a heatmap indicating absolute neutrophil count (ANC) according to neutropenia toxicity grade (i.e., Grades 1, 2, 3, and 4) in healthy subjects administered three doses of 0.6 mg/kg CSL324, as described in Example 1.

FIG. 6 shows graphs illustrating the effect of CSL324 on G-CSF-induced neutrophil migration. Pre-incubation in the presence of G-CSF alone induced migration of neutrophils to MIP-2 (FIG. 6A; black bars), which was reduced to the same levels as the media alone control by CSL324 (FIG. 6A; grey bars). Pre-incubation with G-CSF resulted in up-regulation of CXCR1 and CXCR2 that correlated with increased migration of neutrophils to MIP-2 (FIGS. 6B and 6C).

15

16

Figure 7:
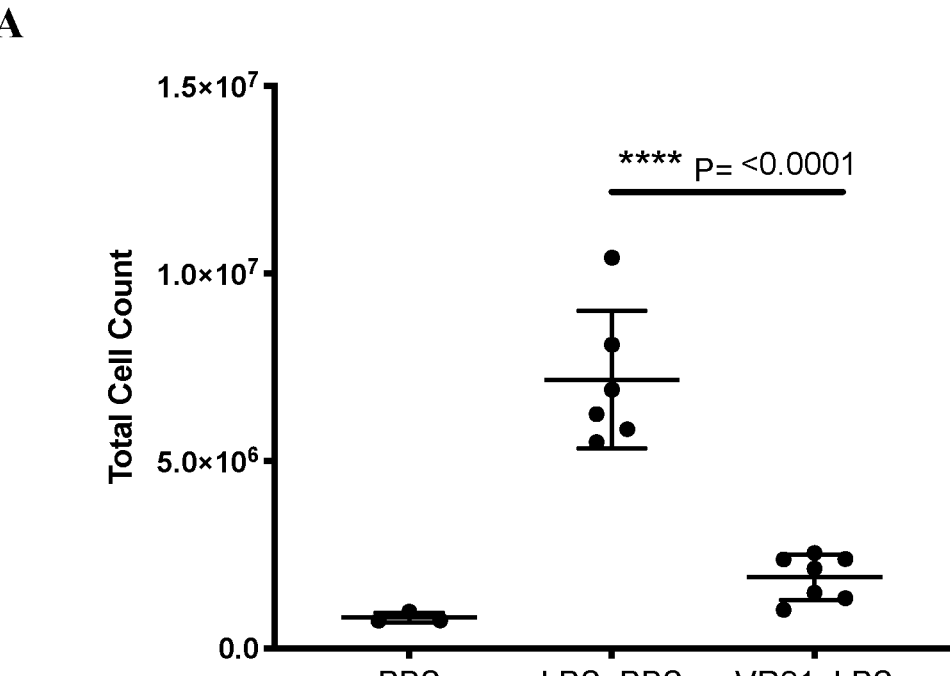
Figure 7:
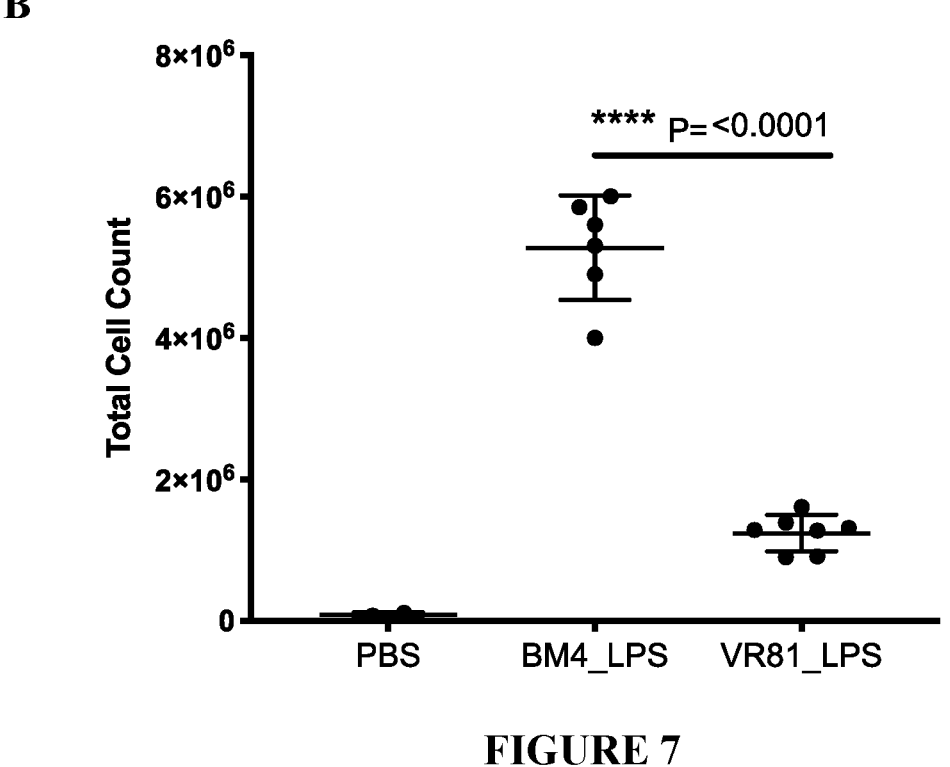

FIG. 7 shows graphs illustrating the effect of VR81 (a mouse surrogate antibody for CSL324) on cell counts in bronchoalveolar lavage (BAL) in a mouse model of ARDS relative to PBS (FIG. 7A) and isotype antibody (FIG. 7B) controls.

Figure 8:
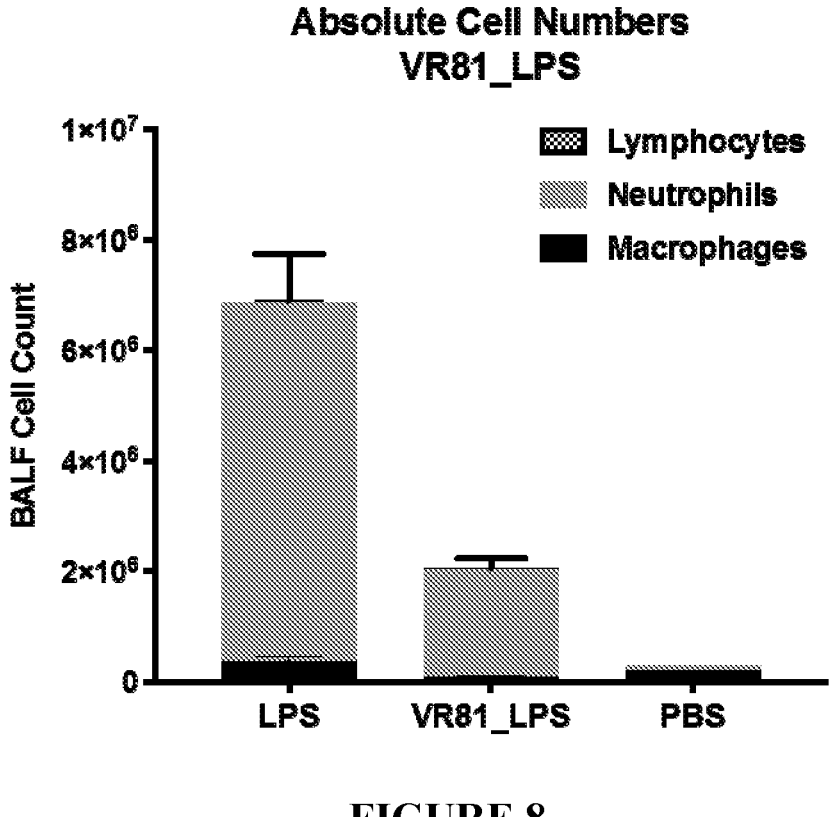

FIG. 8 is a graph illustrating the effect of VR81 (a mouse surrogate antibody for CSL324) on absolute immune cell counts in bronchoalveolar lavage (BAL) in a mouse model of ARDS.

Figure 9:
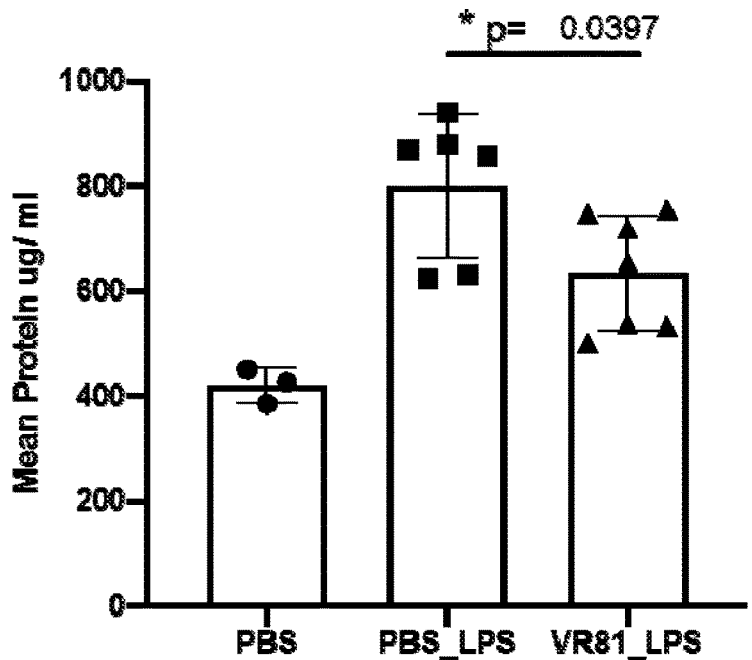
Figure 9:
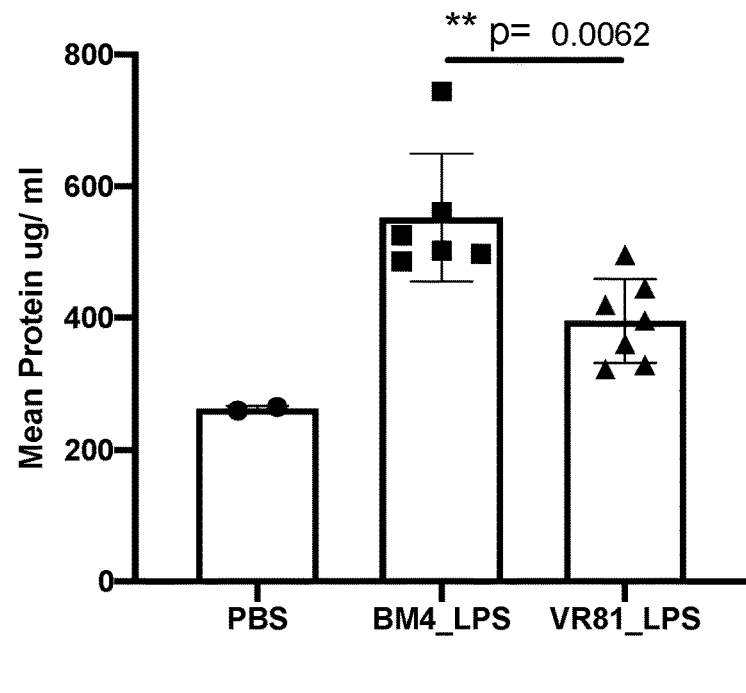

FIG. 9 shows graphs illustrating the effect of VR81 (a mouse surrogate antibody for CSL324) on the level of total protein in bronchoalveolar lavage (BAL) in a mouse model of ARDS relative to PBS (FIG. 9A) and isotype antibody (FIG. 9B) controls.

Figure 10:
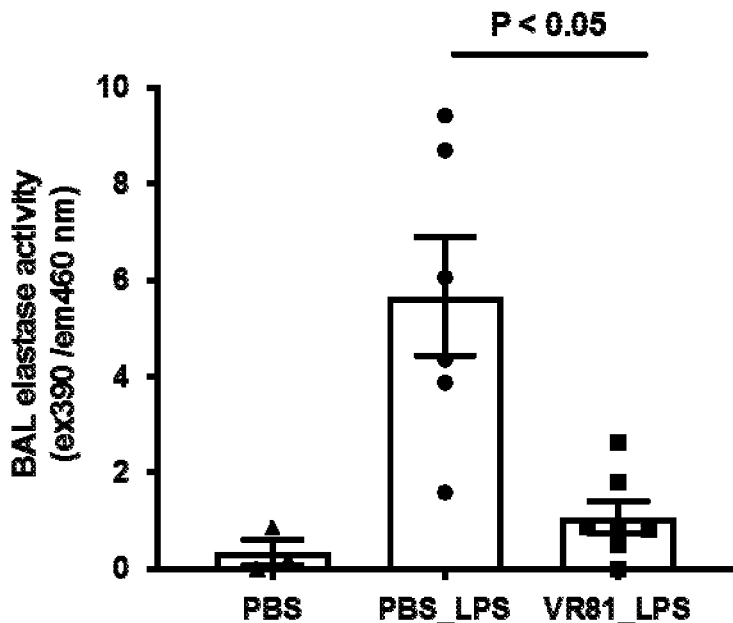
Figure 10:
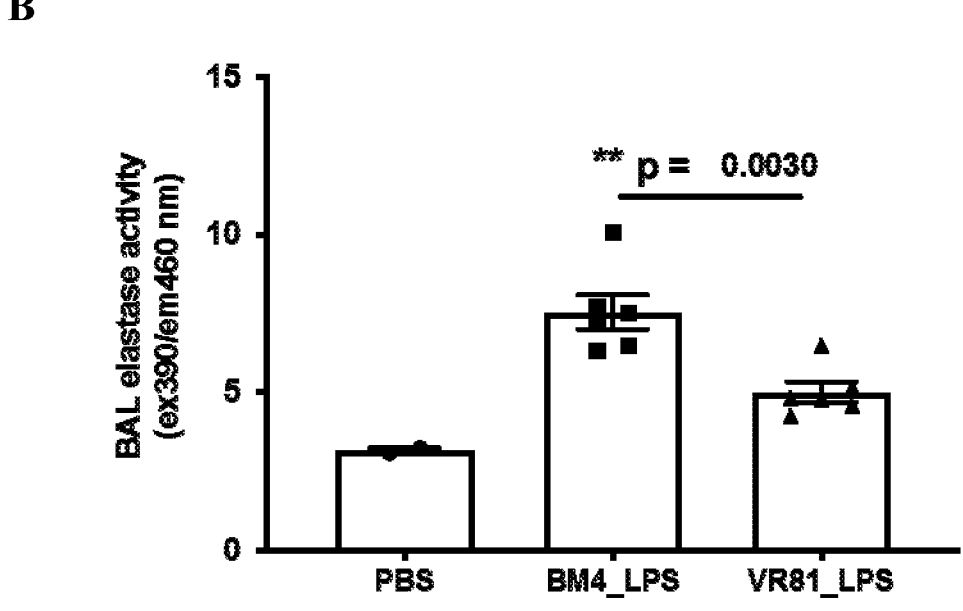

FIG. 10 shows graphs illustrating the effect of VR81 (a mouse surrogate antibody for CSL324) on the level neutrophil elastase activity in bronchoalveolar lavage (BAL) in a mouse model of ARDS relative to PBS (FIG. 10A) and isotype antibody (FIG. 10B) controls.

Figure 11:
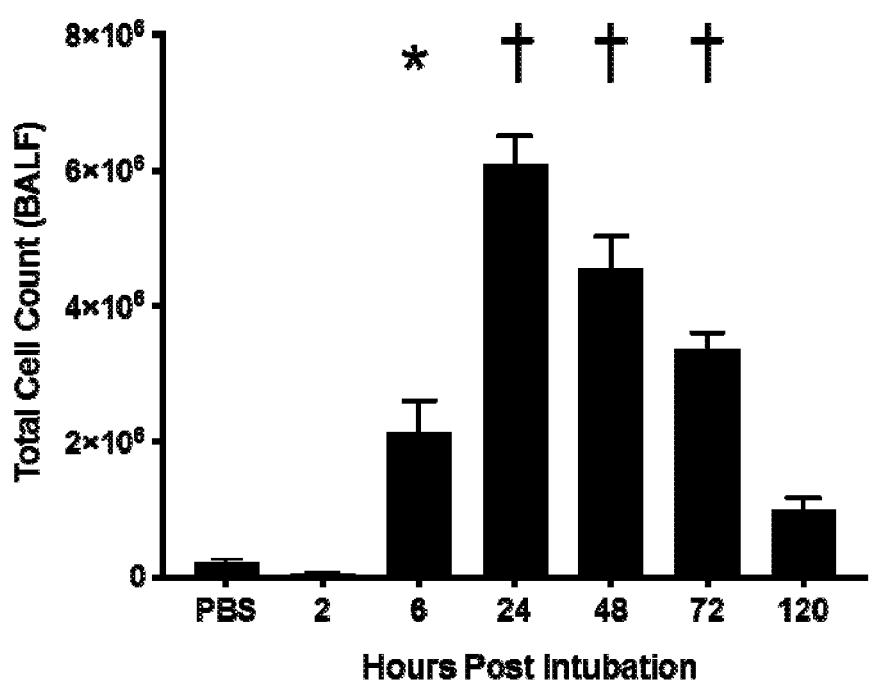
Figure 11:
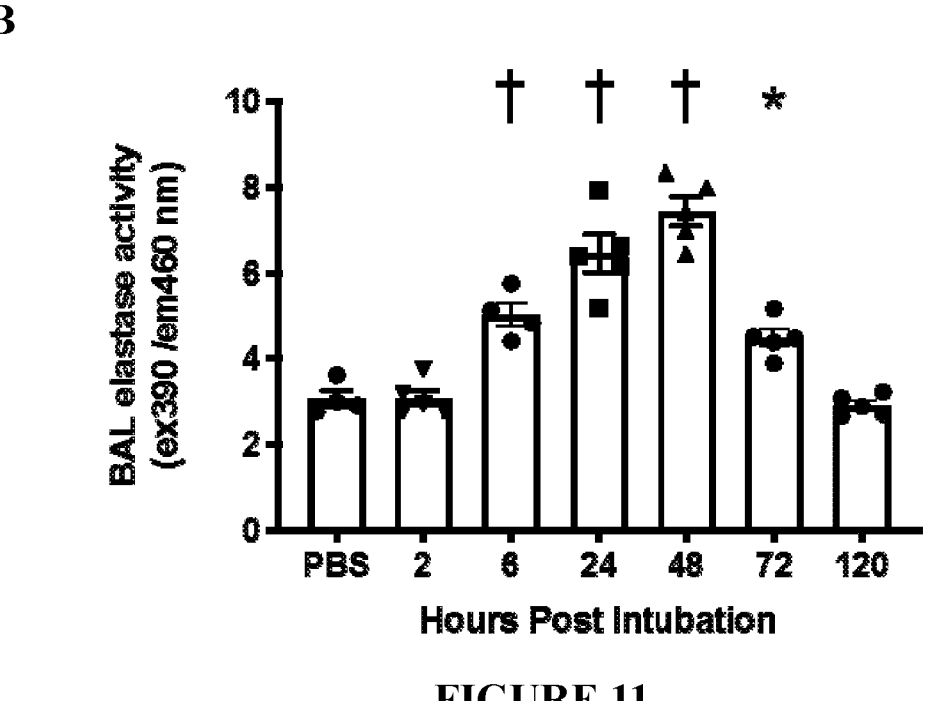

FIG. 11 shows progression of lung inflammation in the animal model of ARDS used in Example 3. FIG. 11A shows total cell counts from broncho-alveolar lavage fluid (BALF) obtained from mice at different times after administration with 3 μg LPS. Columns show means±SEM (n=5 mice per group). *P<0.01, †P<0.0001, compared to PBS control; one-way ANOVA with Dunnett's test. FIG. 11B shows neutrophil elastase activity (60 min assay) in broncho-alveolar lavage fluid (BALF) obtained from mice at different times after administration with 3 μg LPS. Columns show means J SEM (n=5 mice per group); points represent individual mice. *P<0.01, †P<0.0001, compared to PBS control; one-way ANOVA with Dunnett's test.

Figure 12:
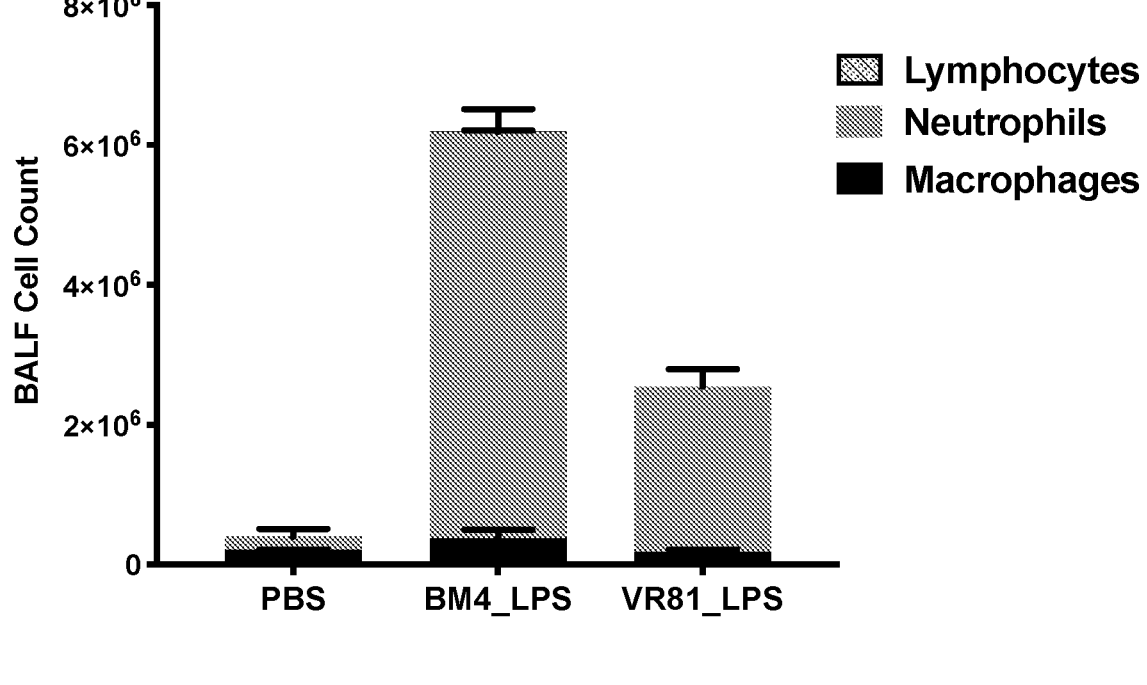

FIG. 12 shows a graph illustrating therapeutic efficacy of VR81 when administered 6 hours after disease onset. Total cell counts are shown (means±SEM) in stacked columns for lymphocytes, neutrophils and macrophages from broncho-alveolar lavage fluid (BALF) obtained from mice 24 h after intubation with 3 μg LPS (2 right columns) or PBS (left column). Mice were treated 6 h after intubation by i.v. injection of 500 μg VR81 or isotype control BM4. There was a significant difference (P<0.0001) in neutrophil numbers between the VR81 and BM4 groups (Student's t-test); n=2 (PBS), 6 (BM4_LPS) and 7 (VR81_LPS).

Figure 13:
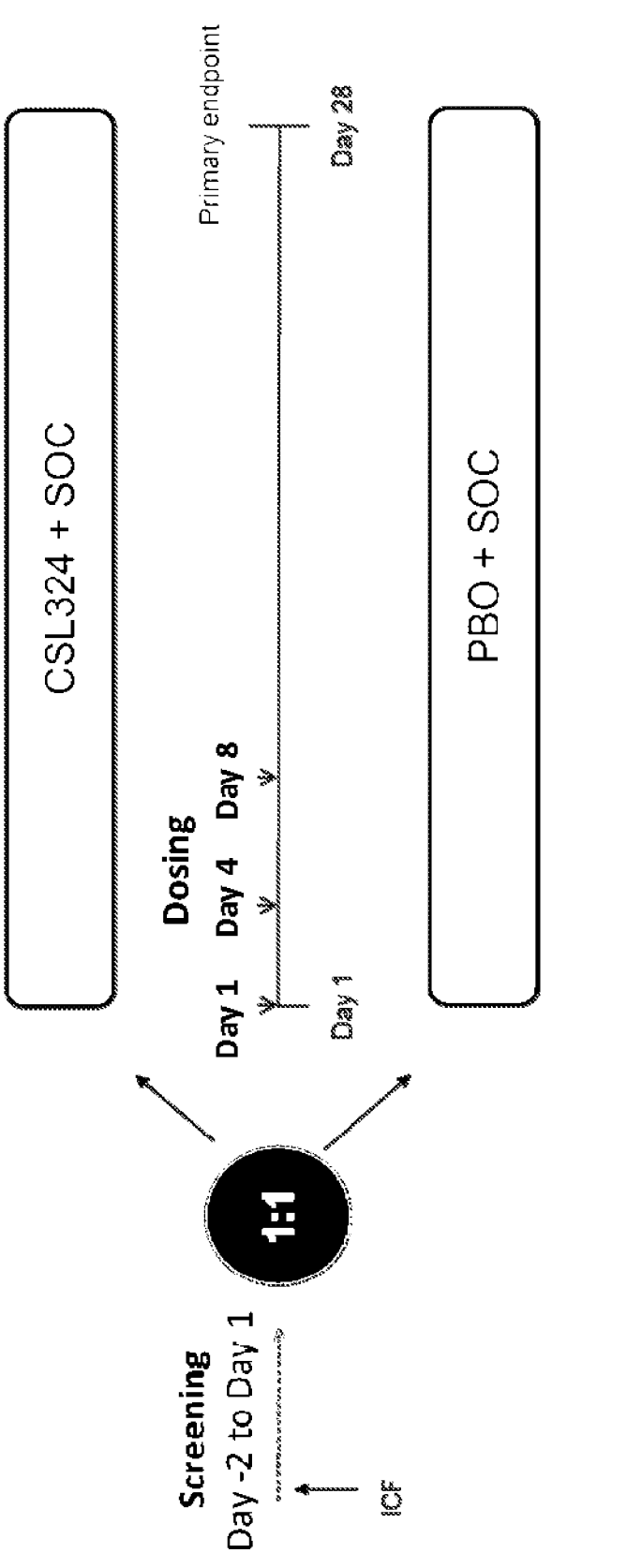

FIG. 13 is a schematic of the study protocol described in Example 4.

Figure 14:
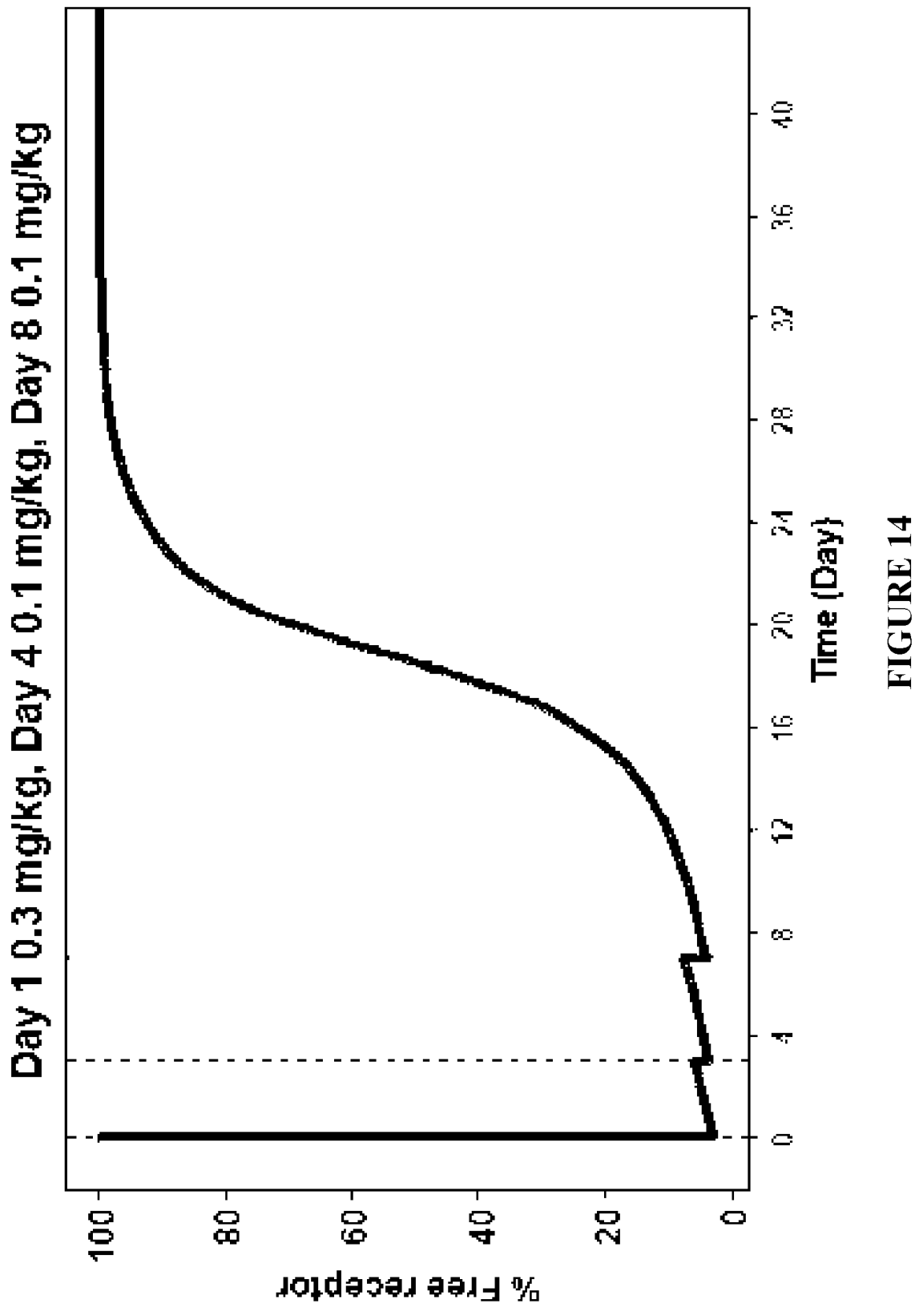
Figure 14:
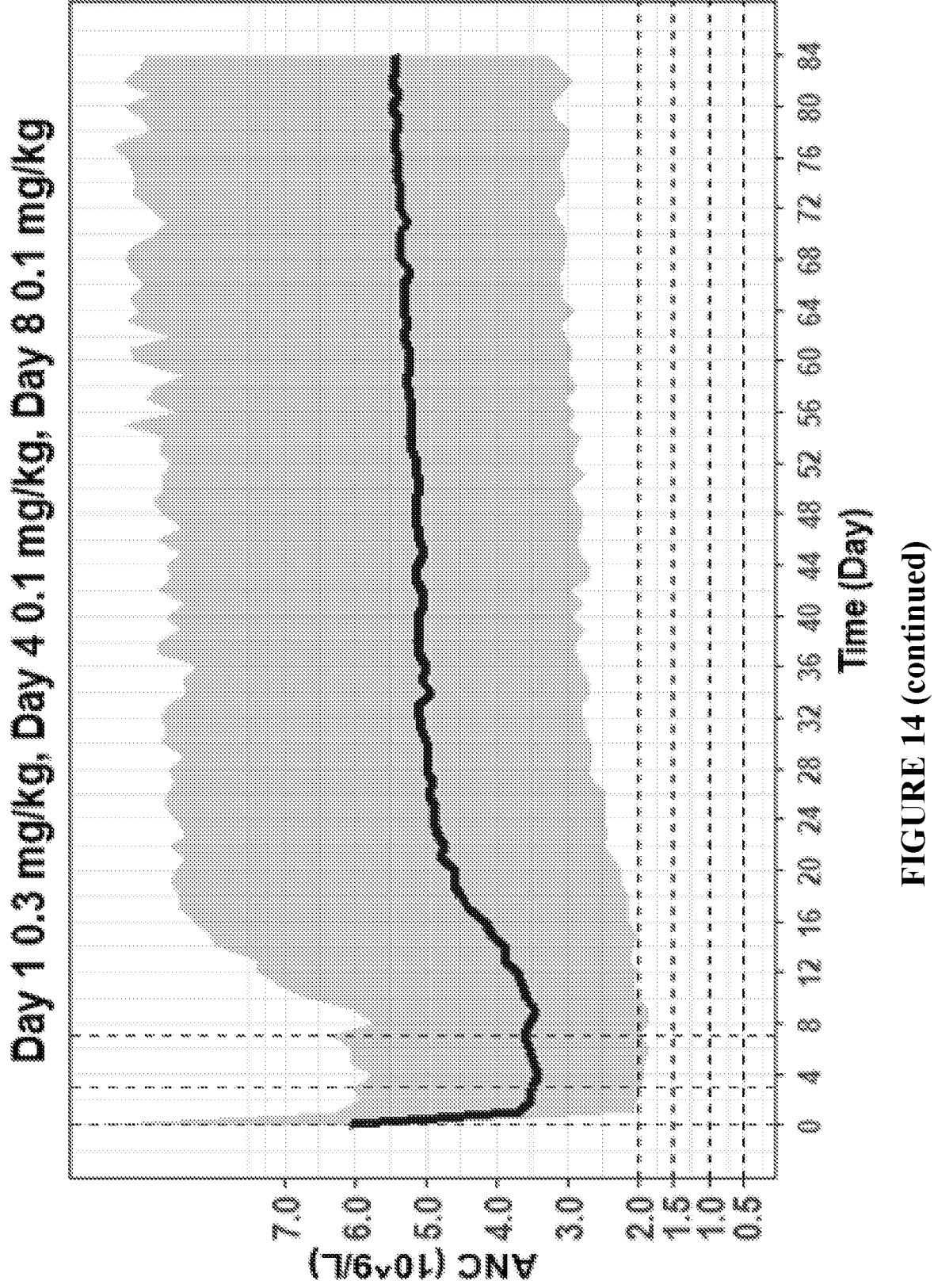

FIG. 14 shows predictions for receptor occupancy and ANC counts over time for the dosage regimens described in Example 4.

Figure 15:
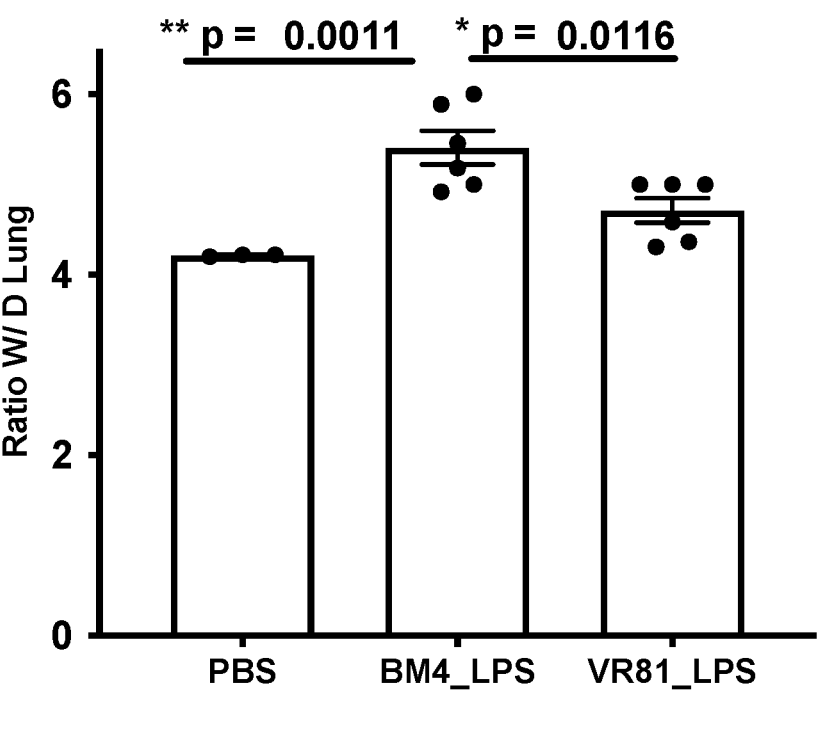

FIG. 15 is a graph illustrating the effect of VR81 (a mouse surrogate antibody for CSL324) on lung edema, as measured by wet-to-dry (W/D) lung weight ratio, in a mouse model of ARDS. Administration of 500 μg/mouse of VR81 one day prior to LPS significantly reduced the W/D ratio relative to mice administered the isotype control antibody, BM4.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply *Mutatis mutandis* to any other example of the disclosure unless specifically stated otherwise.

Unless specifically defined otherwise, all technical and scientific terms used herein shall be taken to have the same meaning as commonly understood by one of ordinary skill in the art (for example, in immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present). Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

A "compound", as contemplated by the present disclosure, can take any of a variety of forms including natural compounds, chemical small molecule compounds or biological compounds or macromolecules. Exemplary compounds include an antibody or a protein comprising an antigen binding fragment of an antibody, a nucleic acid, a polypeptide, a peptide, and a small molecule.

Reference herein to "granulocyte colony-stimulating factor" (G-CSF) includes native forms of G-CSF, mutant forms thereof, e.g., filgrastim and pegylated forms of G-CSF or filgrastim. This term also encompasses mutant forms of G-CSF retaining activity to bind to G-CSFR (e.g., human G-CSFR) and induce signaling.

G-CSF is a major regulator of granulocyte production. G-CSF is produced by bone marrow stromal cells, endothelial cells, macrophages, and fibroblasts, and production is induced by inflammatory stimuli. G-CSF acts through the G-CSF receptor (G-CSFR), which is expressed on early myeloid progenitors, mature neutrophils, monocytes/macrophages, T and B lymphocytes and endothelial cells.

For the purposes of nomenclature only and not limitation, an exemplary sequence of a human G-CSFR is set out in NCBI Reference Sequence: NP_000751.1 (and set out in SEQ TD NO: 16). The sequence of G-CSFR from other species can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human G-CSFR may be abbreviated to hG-CSFR and reference to cynomolgus monkey G-CSFR may be abbreviated to cynoG-CSFR. Reference to soluble G-CSFR refers to polypeptides comprising the ligand binding region of G-CSFR. The Ig and CRH domains of the G-CSFR are involved in ligand binding and receptor dimerization (Layton et al., *J. Biol Chem.*, 272: 29735-29741, 1997 and Fukunaga et al, *EMBO J.* 10: 2855-2865, 1991). Soluble forms of G-CSFR comprising these portions of the receptor have been used in various studies of the receptor and mutation of the free cysteines at positions 78, 163, and 228 of the receptor assists in expression and isolation of the soluble receptor polypeptide (Mine et al., *Biochem.*, 43: 2458-2464 2004) without affecting ligand binding.

As used herein, the term "disease" or "condition" refers to a disruption of or interference with normal function, and is not to be limited to any specific condition, disease or disorder.

As used herein, the terms "treating", "treat" or "treatment" include administering a compound described herein to reduce, prevent, or eliminate at least one symptom of a specified disease or condition.

As used herein, the terms "preventing", "prevent" or "prevention" include administering a compound described herein to thereby stop or hinder the development of at least one symptom of a condition, e.g., before that symptom is fully developed in the subject. For example, in accordance with the methods of the present disclosure a compound can be administered to a subject to prevent a subject's $PaO_2$/$FiO_2$ ratio from falling below 300 mmHg.

As used herein, the term "subject" shall be taken to mean any animal including humans, for example a mammal. Exemplary subjects include but are not limited to humans and non-human primates. In one example, the subject is a human.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions. In some examples, the protein is a fusion protein. As used herein, a "fusion protein" is a protein comprising at least two domains that have been joined so that they are translated as a single unit, producing a single protein.

The term "polypeptide" or "polypeptide chain" will be understood from the foregoing paragraph to mean a series of contiguous amino acids linked by peptide bonds.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

As used herein, the term "antigen binding site" shall be taken to mean a structure formed by a protein that is capable of binding or specifically binding to an antigen. The antigen binding site need not be a series of contiguous amino acids, or even amino acids in a single polypeptide chain. For example, in a Fv produced from two different polypeptide chains the antigen binding site is made up of a series of amino acids of a $V_L$ and a $V_H$ that interact with the antigen and that are generally, however not always in the one or more of the CDRs in each variable region. In some examples, an antigen binding site is a $V_H$ or a $V_L$ or a Fv. In some examples, the antigen binding site comprises one or more CDRs of an antibody.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are necessary for antigen binding. Each variable region typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997, the IMGT numbering system of Lefranc et al., *Devel. And Comnar. Immunol.,* 27: 55-77, 2003; or the AHO numbering system of Honnegher and Plükthun *J. Mol. Biol.,* 309: 657-670, 2001. For example, according to the numbering system of Kabat, $V_H$ framework regions (FRs) and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including those discussed above. In one example, reference herein to a CDR (or a FR) is in respect of those regions according to the Kabat numbering system.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain (CL). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H^2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a compound or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a compound of the disclosure reacts or associates more frequently, more rapidly, with greater duration and/or with greater affinity with a particular antigen or cell expressing same than it does with alternative antigens or cells. For example, a compound binds to G-CSFR (e.g., hG-CSFR) with materially greater affinity (e.g., 20 fold or 40 fold or 60 fold or 80 fold to 100 fold or 150 fold or 200 fold) than it does to other cytokine receptor or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

A protein or antibody may be considered to "preferentially bind" to a polypeptide if it binds that polypeptide with a dissociation constant ($K_D$) that is less than the protein's or antibody's $K_D$ for another polypeptide. In one example, a protein or antibody is considered to preferentially bind to a polypeptide if it binds the polypeptide with an affinity (i.e., $K_D$) that is at least about 20 fold or 40 fold or 60 fold or 80 fold or 100 fold or 120 fold or 140 fold or 160 fold more than the protein's or antibody's $K_D$ for another polypeptide.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "$IC_{50}$ of at least about" will be understood to mean that the $IC_{50}$ is equal to the recited value or greater (i.e., the value recited as the $IC_{50}$ is lower), i.e., an $IC_{50}$ of 2 nM is greater than an $IC_{50}$ of 3 nM. Stated another way, this term could be "an $IC_{50}$ of X or less", wherein X is a value recited herein.

As used herein, the term "epitope" (syn. "antigenic determinant") shall be understood to mean a region of G-CSF or hG-CSFR to which a protein comprising an antigen binding site of an antibody binds. This term is not necessarily limited to the specific residues or structure to which the protein makes contact. For example, this term includes the region spanning amino acids contacted by the protein and/or 5-10 or 2-5 or 1-3 amino acids outside of this region. In some examples, the epitope comprises a series of discontinuous amino acids that are positioned close to one another when G-CSF or hG-CSFR is folded, i.e., a "conformational epitope". For example, a conformational epitope in hG-CSFR comprises amino acids in one or more or two or more or all of the regions corresponding to 111-115, 170-176, 218-234 and/or 286-300 of SEQ ID NO: 1. The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that a protein of the disclosure (or an antigen binding site thereof) reduces or prevents binding of a recited antibody or protein to G-CSF or G-CSFR, e.g., to hG-CSFR. This may be due to the protein (or antigen binding site) and antibody binding to the same or an overlapping epitope. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to G-CSF or G-CSFR either in the presence or absence of the protein. If less antibody binds in the presence of the protein than in the absence of the protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a protein (or antigen binding site thereof) that binds to one epitope to competitively inhibit the binding of a protein (or antigen binding site) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a compound is capable of blocking, reducing or preventing G-CSF-mediated signaling in a cell through the G-CSFR. Methods for determining neutralization are known in the art and/or described herein.

As used herein, the term "neutropenia" is used to refer to an absolute neutrophil count (ANC) below the lower limit of normal range, for example an ANC of less than 2000 cells/μL blood, or less than 1500 cells/μL blood, or less than 1000 cells/μL blood, for example less than 500 cells/μL blood (see Sibille et al. 2010 *Br J Clin Pharmacol* 70(5): 736-748). In some examples, the antibody that inhibits G-CSF signaling is administered in an amount that does not cause severe neutropenia. As used herein, the term "severe neutropenia" is used to refer to an absolute neutrophil count (ANC) of less than 1000 cells/μL blood. For the purposes of the present disclosure, the following ANCs will be used to define the grades of neutropenia Grade 1: $<2.0 \times 10^9$/L ($<2000$/mm³) and $>1.5 \times 10^9$/L ($>1500$/mm³)

Grade 2: $<1.5 \times 10^9$/L ($<1500$/mm³) and $>1.0 \times 10^9$/L ($>1000$/mm³)

Grade 3: $<1.0 \times 10^9$/L ($<1000$/mm³) and $>0.5 \times 10^9$/L ($>500$/mm³)

Grade 4: $<0.5 \times 10^9$/L ($<500$/mm³).

Treatment and Prevention of Acute Respiratory Distress Syndrome

The present disclosure provides, for example, a method for treating or preventing acute respiratory distress syndrome (ARDS) in a subject.

ARDS is a life-threatening condition characterized by bilateral pulmonary infiltrates, severe hypoxemia, and non-cardiogenic pulmonary edema. ARDS results in severe lung damage and an attributable mortality rate of 30-50%. As yet, there is no effective pharmacological therapy. Infectious etiologies, such as sepsis and pneumonia (including influenza and coronavirus infection), are leading causes of ARDS. Therefore, the treatment of these underlying diseases or disorders (e.g., the infection) is also contemplated in combination with the methods of the disclosure.

Histologically, ARDS in humans is characterized by a severe acute inflammatory response in the lungs and neutrophilic alveolitis. Inflammatory stimuli from microbial pathogens, such as endotoxin (lipopolysaccharide, LPS), are well recognized for their ability to induce pulmonary inflammation, and experimental administration of LPS, both systemically and intratracheally, has been used to induce pulmonary inflammation in animal models of ARDS, as described herein. LPS acts via Toll-like receptor 4 (TLR4), to increase the expression of inflammatory cytokines and chemokines, and upregulate leukocyte adhesion molecules, resulting in endothelial cell activation.

The physiological hallmark of ARDS is disruption of the alveolar-capillary membrane barrier (i.e., pulmonary vascular leak), leading to development of non-cardiogenic pulmonary edema in which a proteinaceous exudate floods the alveolar spaces, impairs gas exchange, and precipitates respiratory failure. Both alveolar epithelial and endothelial cell injury and/or death have been implicated in the pathogenesis of ARDS. ARDS continues to be a significant contributor to prolonged mechanical ventilation in the intensive care unit (ICU), and ARDS-associated mortality remains high at 30-50% despite optimal ICU supportive care.

ARDS was defined by a panel of experts in 2012 (an initiative of the European Society of Intensive Care Medicine endorsed by the American Thoracic Society and the Society of Critical Care Medicine) as the Berlin Definition. Presently there are three stages mild, moderate, and severe with an associated increased mortality (27%; 95% CI, 24%-30%; 32%; 95% CI, 29%-34%; and 45%; 95% CI, 42%-48%, respectively; P<0.001) and increased median duration of mechanical ventilation in survivors (5 days; interquartile [IQR], 2-11; 7 days; IQR, 4-14; and 9 days, IQR, 5-17, respectively, P<0.001). The definition was empirically evaluated using patient-level meta-analysis of 4188 patients with ARDS from 4 multicenter clinical data sets and 269 patients with ARDS from 3 single-center data sets containing physiologic information.

According to the Berlin definition, ARDS is defined by
(1) presentation within 1 week of clinical insult or onset of respiratory symptoms;
(2) acute hypoxemic respiratory failure, as determined by a PaO$_2$/FiO$_2$ ratio of 300 mmHg or less on at least 5 cm of continuous positive airway pressure (CPAP) or positive end expiratory pressure (PEEP), where PaO$_2$ is the partial pressure of oxygen in arterial blood and the FiO$_2$ is the fraction of inspired oxygen;
(3) bilateral opacities on lung radiographs not fully explained by effusions, consolidation, or atelectasis; and
(4) edema/respiratory failure not fully explained by cardiac failure or fluid overload.

In an example of the methods of the present disclosure, the subject satisfies the above Berlin criteria for ARDS. In other examples, the subject may not yet satisfy the Berlin criteria for ARDS but is identified as at risk of developing ARDS. Such subjects can be administered the compound that inhibits G-CSF signaling to prevent onset of ARDS.

As used herein, the term "at risk" means that the subject has an increased chance of developing ARDS compared to a normal individual. Subjects can be identified as at risk of developing ARDS using any method known in the art. For example, the subject may be identified at risk of developing ARDS if that subject has a common underlying cause of ARDS (e.g., sepsis, pneumonia, trauma etc.) and has respiratory symptoms, for example, fast breathing and/or shortness of breath. Other methods suitable for identifying subjects at risk of developing ARDS include, for example, the methods described in WO2018/204509; Luo et al., 2017, J Thorac Dis 9, 3979-3995; de Haro et al., 2013, *Annals of Intensive Care* 3, 11; Triyama et al, 2020, *Journal of Intensive Care* 8, 7; Gajic et al., 2011, *Am J Respir Crit Care Med* 183, 462-470; and Yadav et al., 2017, *Am J Respir Crit Care Med* 195, 725-736.

The severity of ARDS can be categorised as follows:
(1) Mild ARDS: PaO$_2$/FiO$_2$ of 200-300 mmHg;
(2) Moderate ARDS: PaO$_2$/FiO$_2$ of 100-200 mmHg; and
(3) Severe ARDS: PaO$_2$/FiO$_2$ of less than or equal to 100 mmHg.

In some examples of the methods of the disclosure, the ARDS is mild ARDS. In some examples, the ARDS is moderate ARDS. In some examples, the ARDS is severe ARDS.

Due to the mechanism of action of G-CSF inhibitors, the methods of the present disclosure are suited to all causes of ARDS. The most common causes of ARDS are sepsis, aspiration of harmful substances, pneumonia, severe trauma (bilateral lung contusion, fat embolism after long bone fracture, sepsis that develops several days after severe trauma or burns, and massive traumatic tissue injury), massive transfusion, transfusion related acute lung injury, lung and hematopoietic stem cell transplantation, other acute inflammatory diseases, drugs and alcohol, and genetic determinants such as mutations in the surfactant protein B (SP-B) gene.

More recently, ARDS has been shown to result from severe coronavirus disease 2019 (COVID-19), i.e., viral pneumonia from SARS-CoV-2 (severe acute respiratory syndrome coronavirus 2) infection. Other coronavirus infections in the past have caused SARS and MERS, which also can result in ARDS. SARS-CoV-2 infection can be confirmed by positive detection of viral RNA in nasopharyngeal secretions using a specific PCR test. COVID-19 illness can be confirmed by a consistent clinical history, epidemiological contact, and a positive SARS-CoV-2 test. ARDS associated with COVID-19 can be diagnosed when a subject with confirmed COVID-19 infection meets the Berlin ARDS diagnostic criteria described above.

Antibodies

In one example, a compound as described herein according to any example is a protein comprising an antigen binding site of an antibody. In some examples, the compound that inhibits G-CSF signaling is an antibody. In some examples, the antibody binds to G-CSFR. In some examples, the antibody binds to G-CSF.

Methods for generating antibodies are known in the art and/or described in Harlow and Lane (editors) Antibodies: A Laboratory Manual, Cold Spring Harbor Laboratory, (1988). Generally, in such methods G-CSFR or G-CSF (e.g., hG-CSFR or hG-CSF) or a region thereof (e.g., an extracellular domain) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

Monoclonal antibodies are one exemplary form of an antibody contemplated by the present disclosure. The term "monoclonal antibody" or "mAb" refers to a homogeneous antibody population capable of binding to the same antigen(s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

Alternatively, ABL-MYC technology (NeoClone, Madison WI 53713, USA) is used to produce cell lines secreting MAbs (e.g., as described in Largaespada et al, J. *Immunol Methods.* 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

An antibody of the present disclosure may be a synthetic antibody. For example, the antibody is a chimeric antibody, a humanized antibody, a human antibody or a de-immunized antibody.

In one example, an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Methods for producing chimeric antibodies are described in, e.g., U.S. Pat. No. 4,816,567; and 5,807,715.

The antibodies of the present disclosure may be humanized or human.

The term "humanized antibody" shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from the non-human antibody grafted onto appropriate FRs in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues.

Methods for humanizing non-human antibodies or parts thereof (e.g., variable regions) are known in the art. Humanization can be performed following the method of U.S. Pat. No. 5,225,539, or U.S. Pat. No. 5,585,089. Other methods for humanizing an antibody are not excluded.

The term "human antibody" as used herein refers to antibodies having variable regions (e.g. $V_H$, $V_L$) and, optionally constant regions derived from or corresponding to sequences found in humans, e.g. in the human germline or somatic cells.

Exemplary human antibodies are described herein and include C1.2 and C1.2G and/or variable regions thereof. These human antibodies provide an advantage of reduced immunogenicity in a human compared to non-human antibodies. Exemplary antibodies are described in WO2012/171057. Other antibodies suitable for use in accordance with the methods of the disclosure include those described in WO2018/145206.

In one example, the antibody is a multispecific antibody. For instance, the compound that inhibits G-CSF signaling may be a protein comprising an antigen binding site that binds to G-CSF or G-CSFR and a further antigen binding site that binds to a different antigen. Thus, in some examples, the antibody is a bispecific antibody.

Antibody Binding Domain Containing Proteins
Single-Domain Antibodies

In some examples, a compound of the disclosure is a protein that is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e g, U.S. Pat. No. 6,248,516).

Diabodies, Triabodies, Tetrabodies

In some examples, a protein of the disclosure is or comprises a diabody, triabody, tetrabody or higher order protein complex such as those described in WO98/044001 and/or WO94/007921.

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Antibody Fragments

The present disclosure also contemplates other antibodies and antibody fragments, such as:

(i) "key and hole" bispecific proteins as described in U.S. Pat. No. 5,731,168;

(ii) heteroconjugate proteins, e.g., as described in U.S. Pat. No. 4,676,980, (iii) heteroconjugate proteins produced using a chemical cross-linker, e.g., as described in U.S. Pat. No. 4,676,980; and (iv) $Fab_3$ (e.g., as described in EP19930302894).

V-Like Proteins

An example of a compound of the disclosure is a T-cell receptor. T cell receptors have two V-domains that combine into a structure similar to the Fv module of an antibody. Novotny et al., Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid O-sheet secondary structure with a plurality of loops at the open end of the conical structure which can be engineered to bind to an antigen. Such engineered lipocalins are known as anticalins. For further description of anticalins see U.S. Pat. No. 7,250, 297B1 or US20070224633.

Affibodies

In a further example, a compound of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulfide bonded structure Diversity is generated by shuffling of the natural variation exhibited by the family of A-domains. For further details see WO2002/088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Soluble G-CSFR

The present disclosure also contemplates a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al. *Acta Crystallograph Sect F Struct Biol Cryst Commun.* 61(Pt 8):788-790, 2005.

De-Immunized Proteins

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO2000/34317, WO2004/108158 and WO2004/064724.

Methods for introducing suitable mutations and expressing and assaying the resulting protein will be apparent to the skilled artisan based on the description herein.

Mutations to Proteins

The present disclosure also contemplates mutant forms of a protein of the disclosure. For example, such a mutant protein comprises one or more conservative amino acid substitutions compared to a sequence set forth herein. In some examples, the protein comprises 30 or fewer or 20 or fewer or 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In one example, a mutant protein has only, or not more than, one or two or three or four or five or six conservative amino acid changes when compared to a naturally occurring protein. Details of conservative amino acid changes are provided below. As the skilled person would be aware, e.g., from the disclosure herein, such minor changes can reasonably be predicted not to alter the activity of the protein.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

The present disclosure also contemplates non-conservative amino acid changes (e.g., substitutions) in a protein of the present disclosure, e.g., in a CDR, such as CDR3. For example, the present inventors have identified several non-conservative amino acid substitutions that can be made while retaining an activity of a protein of the disclosure. In one example, the protein comprises fewer than 6 or 5 or 4 or 3 or 2 or 1 non-conservative amino acid substitutions, e.g., in a CDR3, such as in a CDR3.

The present disclosure also contemplates one or more insertions or deletions compared to a sequence set forth herein. In some examples, the protein comprises 10 or fewer, e.g., 9 or 8 or 7 or 6 or 5 or 4 or 3 or 2 insertions and/or deletions.

Constant Regions

The present disclosure encompasses proteins and/or antibodies described herein comprising a constant region of an antibody. This includes antigen binding fragments of an antibody fused to a Fc Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of; alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; *Shields et al., J Biol Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present disclosure also contemplates additional modifications to an antibody or protein of the disclosure.

For example, the antibody comprises one or more amino acid substitutions that increase the half-life of the protein. For example, the antibody comprises a Fc region comprising one or more amino acid substitutions that increase the affinity of the Fc region for the neonatal Fc receptor (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half-life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

The protein may be fusion protein. Thus, in one example, the protein additionally comprises albumin, a functional fragment or variant thereof. In one example, the albumin, functional fragment or variant thereof is serum albumin, such as human serum albumin. In one example, the albumin, functional fragment or variant thereof, comprises one or more amino acid substitutions, deletions or insertions, e.g., no more than 5 or 4 or 3 or 2 or 1 substitutions. Amino acid substitutions suitable for use in the present disclosure will be apparent to the skilled person and include naturally-occurring substitutions and engineered substitutions such as those described, for example, in WO2011/051489, WO2014/072481, WO2011/103076, WO2012/112188, WO2013/075066, WO2015/063611 and WO2014/179657.

In one example, the protein of the disclosure additionally comprises a soluble complement receptor or functional fragment or variant thereof. In one example, the protein additionally comprises a complement inhibitor.

Protein Production

In one example, a protein described herein according to any example is produced by culturing a hybridoma under conditions sufficient to produce the protein, e g, as described herein and/or as is known in the art.

Recombinant Expression

In another example, a protein described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising Pichia pastoris, Saccharonyces cerevisiae and S. pombe, include, but are not limited to, the ADH1 promoter, the GAL1 promoter, the GAL4 promoter, the CUP1 promoter, the PHO5 promoter, the nit promoter, the RPR1 promoter, or the TEF1 promoter.

Means for introducing the isolated nucleic acid or expression construct comprising same into a cell for expression are known to those skilled in the art. The technique used for a given cell depends on the known successful techniques.

Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMFM), Sigma) are suitable for culturing mammalian cells. Media for culturing other cell types discussed herein are known in the art.

Isolation of Proteins

Methods for isolating a protein are known in the art and/or described herein.

Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO1999/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Nucleic Acid-Based G-CSF Signaling Inhibitors

In one example of the disclosure, therapeutic and/or prophylactic methods as described herein according to any example of the disclosure involve reducing expression of G-CSF and/or G-CSFR. For example, such a method involves administering a compound that reduces transcription and/or translation of a nucleic acid encoding G-CSF or G-CSFR. In one example, the compound that inhibits G-CSF signaling is a nucleic acid, e.g., an antisense polynucleotide, a ribozyme, a PNA, an interfering RNA, a siRNA, a microRNA.

In another example, the compound that inhibits G-CSF signaling is a nucleic acid encoding a protein compound that inhibits G-CSF signaling (e.g., an antibody or antigen binding fragment thereof).

Antisense Nucleic Acids

The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding G-CSF or G-CSFR, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding G-CSF or G-CSFR. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against G-CSF or G-CSFR are described, for example, in WO2011/032204.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding G-CSF or G-CSFR. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815. Such dsRNA molecules for RNAi include, but are not limited to short hairpin RNA (shRNA) and bi-functional shRNA.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search.

Aptamers

In another example, a compound is a nucleic acid aptamer (adaptable oligomer). Aptamers are single stranded oligonucleotides or oligonucleotide analogs that are capable of forming a secondary and/or tertiary structure that provides the ability to bind to a particular target molecule, such as a protein or a small molecule, e.g., G-CSF or G-CSFR. Thus, aptamers are the oligonucleotide analogy to antibodies. In general, aptamers comprise about 15 to about 100 nucleotides, such as about 15 to about 40 nucleotides, for example about 20 to about 40 nucleotides, since oligonucleotides of a length that falls within these ranges can be prepared by conventional techniques.

An aptamer can be isolated from or identified from a library of aptamers. An aptamer library is produced, for example, by cloning random oligonucleotides into a vector (or an expression vector in the case of an RNA aptamer), wherein the random sequence is flanked by known sequences that provide the site of binding for PCR primers. An aptamer that provides the desired biological activity (e.g., binds specifically to G-CSF or G-CSFR) is selected. An aptamer with increased activity is selected, for example, using SELEX (Sytematic Evolution of Ligands by EXponential enrichment). Suitable methods for producing and/or screening an aptamer library are described, for example, in Elloington and Szostak, *Nature* 346:818-22, 1990; U.S. Pat. No. 5,270,163; and/or U.S. Pat. No. 5,475,096.

Assaying Activity of a Compound

Binding to G-CSFR and Mutants Thereof

It will be apparent to the skilled artisan from the disclosure herein that some compounds of the present disclosure bind to the ligand binding domain of hG-CSFR and to specific mutant forms of the ligand binding domain of hG-CSFR (e.g., SEQ ID NO: 1 without or with certain point mutations) and/or bind to both human and cynomolgus monkey G-CSFR. Methods for assessing binding to a protein are known in the art, e.g., as described in Scopes (In: Protein purification: principles and practice, Third Edition, Springer Verlag, 1994). Such a method generally involves labeling the protein and contacting it with immobilized compound. Following washing to remove non-specific bound protein, the amount of label and, as a consequence, bound protein is detected. Of course, the protein can be immobilized and the compound that inhibits G-CSF signaling labeled. Panning-type assays can also be used. Alternatively, or additionally, surface plasmon resonance assays can be used.

The assays described above can also be used to detect the level of binding of a compound to hG-CSFR or a ligand binding domain thereof (e.g., SEQ ID NO: 1) or mutant form thereof.

In one example, a protein of the present disclosure binds to a polypeptide of SEQ ID NO: 1 in which an alanine is substituted for the lysine at position 167 of SEQ ID NO: 1 and/or in which an alanine is substituted for the histidine at position 168 of SEQ ID NO. 1 at substantially the same level (e.g., within 10% or 5% or 1%) as it binds to SEQ ID NO: 1.

In one example, a protein of the present disclosure binds to a polypeptide of SEQ ID NO: 1 in which an alanine is substituted for the arginine at position 287 of SEQ ID NO: 1 at a level at least about 100 fold or 150 fold or 160 fold or 200 fold lower than it binds to a polypeptide of SEQ ID NO: 1 In one example, a protein of the present disclosure binds to a polypeptide of SEQ ID NO: 1 in which an alanine is substituted for the arginine at position 287 of SEQ ID NO: 1 at a level at least about 160 fold lower than it binds to a polypeptide of SEQ ID NO: 1.

In one example, a protein of the present disclosure binds to a polypeptide of SEQ ID NO: 1 in which an alanine is substituted for the histidine at position 237 of SEQ ID NO: 1 at a level at least about 20 fold or 40 fold or 50 fold or 60 fold lower than it binds to a polypeptide of SEQ ID NO: 1. In one example, a protein of the present disclosure binds to a polypeptide of SEQ ID NO: 1 in which an alanine is substituted for the histidine at position 237 of SEQ ID NO: 1 at a level at least about 50 fold lower than it binds to a polypeptide of SEQ ID NO: 1.

In one example, a protein of the present disclosure binds to a polypeptide of SEQ ID NO: 1 in which an alanine is substituted for the methionine at position 198 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the methionine at position 198 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the tyrosine at position 172 of SEQ ID NO: 1 at a level at least about 20 fold or 30 fold or 40 fold lower than it binds to a polypeptide of SEQ ID NO: 1. In one example, a protein of the present disclosure binds to a polypeptide of SEQ ID NO: 1 in which an alanine is substituted for the tyrosine at position 172 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the leucine at position 171 of SEQ ID NO: 1 at a level at least about 100 fold or 120 fold or 130 fold or 140 fold lower than it binds to a polypeptide of SEQ ID NO: 1. In one example, a protein of the present disclosure binds to a polypeptide of SEQ ID NO: 1 in which an alanine is substituted for the leucine at position 171 of SEQ ID NO: 1 at a level at least about 140 fold lower than it binds to a polypeptide of SEQ ID NO: 1.

In one example, a protein of the present disclosure binds to a polypeptide of SEQ ID NO: 1 in which an alanine is substituted for the leucine at a position 111 of SEQ ID NO:

1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the leucine at a position 111 of SEQ ID NO: 1 at a level at least about 60 fold lower than it binds to a polypeptide of SEQ ID NO. 1.

In one example, a protein of the present disclosure binds to a polypeptide of SEQ ID NO: 1 in which an alanine is substituted for the histidine at position 168 of SEQ ID NO: 1 at a level no more than 5 fold or 4 fold or 3 fold or 2 fold or 1 fold lower than it binds to a polypeptide of SEQ ID NO: 1.

In one example, a protein of the present disclosure binds to a polypeptide of SEQ ID NO: 1 in which an alanine is substituted for the lysine at position 167 of SEQ ID NO: 1 at a level no more than 5 fold or 4 fold or 3 fold or 2 fold or 1 fold lower than it binds to a polypeptide of SEQ ID NO: 1.

The level of binding is conveniently determined using a biosensor.

The present disclosure contemplates any combination of the foregoing characteristics. In one example, a protein described herein has all of the binding characteristics set forth in the preceding seven paragraphs.

Epitope Mapping

In another example, the epitope bound by a protein described herein is mapped. Epitope mapping methods will be apparent to the skilled artisan. For example, a series of overlapping peptides spanning the hG-CSFR sequence or a region thereof comprising an epitope of interest, e.g., peptides comprising 10-15 amino acids are produced. The protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within hG-CSFR are mutated, e.g., by alanine scanning mutagenesis, and mutations that reduce or prevent protein binding are determined. Any mutation that reduces or prevents binding of the protein is likely to be within the epitope bound by the protein.

A further method is exemplified herein, and involves binding hG-CSFR or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in hG-CSFR or a region thereof to deutrons and binding the resulting protein to an immobilized protein of the present disclosure. The deutrons are then converted back to hydrogen, the hG-CSFR or region thereof isolated, digested with enzymes and analyzed, e.g., using mass spectrometry to identify those regions comprising deutrons, which would have been protected from conversion to hydrogen by the binding of a protein described herein.

Optionally, the dissociation constant (Kd) of a protein for hG-CSFR or an epitope thereof is determined. The "Kd" or "Kd value" for a hG-CSFR binding protein is in one example measured by a radiolabeled or fluorescently-labeled hG-CSFR binding assay. This assay equilibrates the protein with a minimal concentration of labeled G-CSFR in the presence of a titration series of unlabeled hG-CSFR.

Following washing to remove unbound hG-CSFR, the amount of label is determined, which is indicative of the Kd of the protein.

According to another example the Kd or Kd value is measured by using surface plasmon resonance assays, e.g., using BIAcore surface plasmon resonance (BIAcore, Inc., Piscataway, NJ) with immobilized hG-CSFR or a region thereof.

In some examples, proteins having a similar Kd or a higher Kd than C1.2 or C1.2G are selected, because they are likely to compete for binding to hG-CSFR.

Determining Competitive Binding

Assays for determining a protein that competitively inhibits binding of monoclonal antibody C1.2 or C1.2G will be apparent to the skilled artisan. For example, C1.2 or C1.2G is conjugated to a detectable label, e.g., a fluorescent label or a radioactive label. The labeled antibody and the test protein are then mixed and contacted with hG-CSFR or a region thereof (e.g., a polypeptide comprising SEQ ID NO: 1) or a cell expressing same. The level of labeled C1.2 or C1.2G is then determined and compared to the level determined when the labeled antibody is contacted with the hG-CSFR, region or cells in the absence of the protein. If the level of labeled C1.2 or C1.2G is reduced in the presence of the test protein compared to the absence of the protein, the protein is considered to competitively inhibit binding of C1.2 or C1.2G to hG-CSFR.

Optionally, the test protein is conjugated to different label to C1.2 or C1.2G. This alternate labeling permits detection of the level of binding of the test protein to hG-CSFR or the region thereof or the cell.

In another example, the protein is permitted to bind to hG-CSFR or a region thereof (e.g., a polypeptide comprising SEQ ID NO: 1) or a cell expressing same prior to contacting the hG-CSFR, region or cell with C1.2 or C1.2G. A reduction in the amount of bound C1.2 or C1.2G in the presence of the protein compared to in the absence of the protein indicates that the protein competitively inhibits C1.2 or C1.2G binding to hG-CSFR. A reciprocal assay can also be performed using labeled protein and first allowing C1.2 or C1.2G to bind to G-CSFR. In this case, a reduced amount of labeled protein bound to hG-CSFR in the presence of C1.2 or C1.2G compared to in the absence of C1.2 or C1.2G indicates that the protein competitively inhibits binding of C1.2 or C1.2G to hG-CSFR.

Any of the foregoing assays can be performed with a mutant form of hG-CSFR and/or SEQ ID NO: 1 and/or a ligand binding region of hG-CSFR to which C1.2 or C1.2G binds, e.g., as described herein.

Determining Inhibition of G-CSF Signaling

In some examples of the present disclosure, a compound is capable of neutralizing hG-CSFR signaling.

Various assays are known in the art for assessing the ability of a compound to neutralize signaling of a ligand through a receptor.

In one example, the compound that inhibits G-CSF signaling reduces or prevents G-CSF binding to the hG-CSFR. These assays can be performed as a competitive binding assay as described herein using labeled G-CSF and/or labeled protein.

In another example, the compound that inhibits G-CSF signaling reduces formation of CFU-G when CD34$^+$ bone marrow cells are cultured in the presence of G-CSF. In such assays, CD34$^+$ bone marrow cells are cultured in a semi-solid cell culture medium in the presence of G-CSF (e.g., about 10 ng/ml cell culture medium) and, optionally stem cell factor (e.g., about 10 ng/ml cell culture medium) in the presence or absence of a test compound. After a sufficient time for granulocyte clones (CFU-G) to form, the number of clones or colonies is determined. A reduction in the number of colonies in the presence of the compound that inhibits G-CSF signaling compared to in the absence of the compound that inhibits G-CSF signaling indicates that the compound that inhibits G-CSF signaling neutralizes G-CSF signaling. By testing multiple concentrations of the compound that inhibits G-CSF signaling an $IC_{50}$ is determined, i.e., a concentration at which 50% of the maximum inhibition of CFU-G formation occurs. In one example, the $IC_{50}$ is 0.2 nM or less, such as 0.1 nM or less, for example, 0.09 nM or less, or 0.08 nM or less, or 0.07 nM or less, or 0.06 nM or less or 0.05 nM or less. In one example, the $IC_{50}$ is 0.04 nM or less. In another example, the $IC_{50}$ is 0.02 nM or less. The foregoing $IC_{50}$s relate to any CFU-G assay described herein.

In a further example, the compound that inhibits G-CSF signaling reduces proliferation of cells (e.g., BaF3 cells) expressing hG-CSFR which are cultured in the presence of G-CSF. Cells are cultured in the presence of G-CSF (e.g., 0.5 ng/ml) and the presence or absence of a test compound. Methods for assessing cell proliferation are known in the art and include, for example, MTT reduction and thymidine incorporation. A compound that reduces the level of proliferation compared to the level observed in the absence of the compound is considered to neutralize G-CSF signaling. By testing multiple concentrations of the compound an $IC_{50}$ is determined, i.e., a concentration at which 50% of the maximum inhibition of cell proliferation occurs. In one example, the $IC_{50}$ is 6 nM or less, such as 5.9 nM or less. In another example, the $IC_{50}$ is 2 nM or less or nM or less or 0.7 nM or cell or 0.6 nM or less or 0.5 nM or less. The foregoing $IC_{50}$s relate to any cell proliferation assay described herein.

In a further example, the compound that inhibits G-CSF signaling reduces mobilization of hematopoietic stem cells and/or endothelial progenitor cells in vivo following G-CSF administration and/or reduces the number of neutrophils in vivo, e.g., following G-CSF administration (however this is not essential). For example, the compound that inhibits G-CSF signaling is administered, optionally before, at the time of or after administration of G-CSF or a modified form thereof (e.g., PEGylated G-CSF or filgrastim). The number of hematopoietic stem cells (e.g., expressing CD34 and/or Thy 1) and/or endothelial progenitor cells (e.g., expressing CD34 and VEGFR2) and/or neutrophils (identified morphologically and/or expressing e.g., CD10, CD14, CD31 and/or CD88) is assessed. A compound that reduces the level of the cell(s) compared to the level observed in the absence of the compound is considered to neutralize G-CSF signaling. In one example, the compound that inhibits G-CSF signaling reduces the number of neutrophils without inducing neutropenia Other methods for assessing neutralization of G-CSF signaling are contemplated by the present disclosure.

Determining Effector Function

As discussed herein, some proteins of the present disclosure have reduced effector function. Methods for assessing ADCC activity are known in the art.

In one example, the level of ADCC activity is assessed using a $^{51}$Cr release assay, an europium release assay or a $^{35}$S release assay. In each of these assays, cells expressing G-CSFR are cultured with one or more of the recited compounds that inhibit G-CSF signaling for a time and under conditions sufficient for the compound to be taken up by the cell. In the case of a $^{35}$S release assay, cells expressing hG-CSFR can be cultured with $^{35}$S-labeled methionine and/or cysteine for a time sufficient for the labeled amino acids to be incorporated into newly synthesized proteins. Cells are then cultured in the presence or absence of the protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the protein compared to in the absence of protein (or a reduced level of the compound compared to the level observed in the presence of an anti-hG-CSFR antibody comprising a human IgG1 Fc) indicates that the protein has reduced effector function. Exemplary publications disclosing assays for assessing the level of ADCC induced by a protein include Hellstrom, et al. *Proc. Natl Acad. Sci. USA* 83:7059-7063, 1986 and Bruggemann, et al., *J. Exp. Med.* 166:1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

C1q binding assays may also be carried out to confirm that the protein is able to bind C1q and may induce CDC. To assess complement activation, a CDC assay may be performed (see, for example, Gazzano-Santoro et al, *J. Immunol. Methods* 202: 163, 1996.

Determining Half Life

Some proteins encompassed by the present disclosure have an improved half-life, e.g., are modified to extend their half-life compared to proteins that are unmodified. Methods for determining a protein with an improved half-life will be apparent to the skilled person. For example, the ability of a protein to bind to a neonatal Fc receptor (FcRn) is assessed. In this regard, increased binding affinity for FcRn increased the serum half-life of the molecule (see for example, Kim et al., *Eur J Immunol.*, 24:2429, 1994).

The half-life of a protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. Alternatively, or additionally, non-radiolabeled proteins can be detected using an enzyme-linked immunosorbent assay (ELISA). The clearance curve thus obtained should be biphasic, that is, an alpha phase and beta phase. For the determination of the in vivo half-life of the protein, the clearance rate in beta-phase is calculated and compared with that of the wild type or unmodified protein.

Therapeutic Efficacy

The therapeutic efficacy of a compound that inhibits G-CSF signaling can be assessed by comparing the degree of severity of the disease or symptoms in subjects administered with the compound relative to subjects not administered the compound. Alternatively, or additionally, therapeutic efficacy of candidate compounds can be assessed in an animal model.

Intratracheal lipopolysaccharide (LPS)-induced pulmonary inflammation is a well-known and well documented animal model for ARDS (see, for example, Matute-Bello et al., 2011, *Am. J. Respir. Cell Mol. Biol.* 44, 725-738; Orfanos et al., 2004, *Intensive Care Med.* 30, 1702-1714; Tsushima et al., 2009, *Intern. Med.* 48, 621-630). In particular, a model in which the animal is administered LPS intratracheally is preferred over other similar models (e.g., intranasal administration) because the intratracheal model replicates several key pathologic processes of ARDS, including loss of vascular integrity, neutrophil infiltration, and accumulation of protein-rich fluid in the airspaces of the lung (Dagvadorj et al., 2015, *Immunity* 42, 640-653).

In an LPS-induced animal model of ARDS, candidate compounds can be assessed for efficacy by measuring the extent of inflammation in the lungs of the animal relative to a suitable control (i.e., placebo). Inflammation in the lungs can be assessed by measuring cell counts from bronchoalveolar lavage (BAL) and levels of total protein or pro-inflammatory cytokines in BALF and lung parenchymal homogenates. LPS-induced permeability in the lung (i.e. extent of acute lung injury) can also be measured.

In some examples, assessing the therapeutic efficacy of a compound comprises detecting and/or quantifying the level of expression of a biomarker in the subject. Suitable biomarkers for assessing efficacy of treating ARDS include G-CSF, plasminogen activator inhibitor-1 (PAI-1), D-dimer, neutrophil elastase, soluble receptor for AGE (sRAGE), interferon gamma (IFN-γ), interleukin 1β (IL-1β), IL-2, IL-4, IL-6, IL-8, IL-10, IL-12p70, IL-13, and tumor necrosis factor alpha (TNF-α).

Detecting and/or quantifying biomarkers can be performed by any method known in the art. For instance, in one example, the levels of biomarkers are assessed using mass spectrometry. The mass spectrometry may be performed in conjunction with ultra-performance liquid chromatography (UPLC), high-performance liquid chromatography (HPLC), gas chromatography (GC), gas chromatography/mass spectroscopy (GC/MS), and UPLC, for example. Other methods of assessing levels of biomarkers include biological methods, such as but not limited to ELISA assays, Western Blot and multiplexed immunoassays etc. Other techniques may include using quantitative arrays, PCR, Northern Blot analysis. To determine levels of components or factors, it is not necessary that an entire component, e.g., a full length protein or an entire RNA transcript, be present or fully sequenced. In other words, determining levels of, for example, a fragment of protein being analyzed may be sufficient to conclude or assess that the level of the biomarker being analyzed is increased or decreased. Similarly, if, for example, arrays or blots are used to determine component levels, the presence/absence/strength of a detectable signal may be sufficient to assess levels of biomarkers.

To assess levels of biomarkers, a sample may be taken from the subject. The sample may or may not processed prior assaying levels of the components of the biomarker profile. For example, whole blood may be taken from an individual and the blood sample may be processed, e.g., centrifuged, to isolate plasma or serum from the blood. The sample may or may not be stored, e.g., frozen, prior to processing or analysis.

Biological samples that may be tested in a method of the invention include whole blood, blood serum, plasma, tracheal aspirate, BALF, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

Compositions

In some examples, a compound as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing a compound into a suitable form for administration (e.g. a pharmaceutical composition) are known in the art and include, for example, methods as described in Remington's Pharmaceutical Sciences (18th ed., Mack Publishing Co., Easton, Pa., 1990) and U.S. Pharmacopeia. National Formulary (Mack Publishing Company, Easton, Pa., 1984).

The pharmaceutical compositions of this disclosure are particularly useful for parenteral administration, such as intravenous administration or subcutaneous administration or administration into a body cavity or lumen of an organ or joint. The compositions for administration will commonly comprise a solution of the compound that inhibits G-CSF signaling dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compound of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, compounds of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

WO2002/080967 describes compositions and methods for administering aerosolized compositions comprising antibodies for the treatment of respiratory conditions, which are also suitable for administration of compounds in accordance with the methods of the present disclosure.

Combination Therapies

In one example, a compound of the present disclosure is administered in combination with another therapy useful for treating or preventing ARDS, either as combined or additional treatment steps or as additional components of a therapeutic formulation.

In some examples, the other therapy is one that is commonly used to treat or prevent ARDS. Contemplated therapies for ARDS, in combination with the methods of the disclosure, include treatments that involve decreasing lung inflammation, decreasing septal edema, decreasing alveolar and/or endothelial inflammation, treating the underlying cause of ARDS, and/or alleviating another symptom of the ARDS. The other therapy may comprise administration of a compound, cell or other molecule, and/or the other therapy may comprise physical or mechanical forms of therapy, for example artificial ventilation and prone positioning.

In some examples, the other therapy comprises prone positioning, fluid management, oxygenation, artificial ventilation (including newer modes of mechanical ventilation including, but not limited to, high frequency oscillatory ventilation), a glucocorticoid, a surfactant, inhaled nitric oxide, an antioxidant, a protease inhibitor, a recombinant human activated protein C, a $\beta$2-agonist, lisofylline, a statin, inhaled heparin, a diuretic, a sedative, an analgesic, a muscle relaxant, am anti-viral, an antibiotic, inhaled prostacyclin, inhaled synthetic prostacyclin analog, ketoconazole, alprostadil, keratinocyte growth factor, beta-agonists, human mAb against TS factor 7a, interferon receptor agonists, insulin, perfluorocarbon, budesonide, recombinant human ACE, recombinant human CC10 protein, tissue plasminogen activator, human mesenchymal stem cells, or nutritional therapy. In other examples of combination therapy, the other therapy is a glucocorticoid, such as, for example, methylprednisolone, dexamethasone, prednisone, prednisolone, betamethasone, triamcinolone, triamcinolone acetonide budesonide, and beclometasone; beta-agonists, such as, for example, albuterol; lisofylline; rosuvastatin, inhaled heparin; inhaled nitric oxide; recombinant human activated protein C; NSAIDS, such as, for example, ibuprofen; naproxen, and acetaminophen; cisatracurium besylate; procysteine; acetylcysteine; inhaled prostacyclin; ketoconazole; alprostadil; keratinocyte growth factor; human mAb against TS factor 7a; insulin; perfluorocarbons, recombinant human ACE; recombinant human CC10 protein; tissue plasminogen activator; human mesenchymal stem cells; or nutritional therapy such as a combination of omega-3 fatty acids, antioxidants, and $\gamma$-linolenic acids with isocaloric foods and extracorporeal membrane oxygenation (ECMO).

NSAIDS include, but are not limited to, aspirin, acetaminophen, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, and firocoxib.

Analgesics include, but are not limited to, NSAIDS and opioids (narcotics). Opioids include, but are not limited to, dextropropoxyphene, codeine, tramadol, tapentadol, anileridine, alphaprodine, pethidine, hydocodone, morphine, oxycodone, methadone, diamorphine, hydromorphone, oxymorphone, levorphanol, 7-hydroxymitragynine, buprenorphine, fentanyl, sufentanil, bromadol, etorphine, dihydroetorphine, and carfentanil.

Glucocorticoids include, but are not limited to, hydrocortisone, cortisone, prednisone, prednisolone, methylprednisolone, dexamethasone, betamethasone, triamcinolone, beclometasone, or fludrocortisones.

In some examples, the other therapy is a standard of care therapy. Standard of care therapies that are commonly used to treat or prevent ARDS include treatment of the underlying condition (e.g., infection), mechanical or noninvasive ventilation, fluid and hemodynamic therapy, prone positioning, treatment of opportunistic infection, nutrition, and pharmacologic therapy. For example, the Faculty of Intensive Care Medicine (FICM) and Intensive Care Society (ICS) recently released guidelines for standard of care therapy for adult patients with ARDS (Griffiths et al., 2019, *BMJ Open Resp Res* 6: e000420). Where mechanical ventilation is required, the use of low tidal volumes (<6 ml/kg ideal body weight) and airway pressures (plateau pressure <30 cmH2O) was recommended. For patients with moderate/severe ARDS ($PaO_2/FiO_2$ ratio of less than or equal to 150 mmHg), prone positioning was recommended for at least 12 hours per day. The use of a conservative fluid management strategy was suggested for all patients, whereas mechanical ventilation with high positive end-expiratory pressure and the use of the neuromuscular blocking agent cisatracurium for 48 hours was suggested for patients with ARDS with arterial oxygen partial pressure to fractional inspired oxygen ($PaO_2/FiO_2$) ratios less than or equal to 200 mmHg and 150 mmHg, respectively. Extracorporeal membrane oxygenation was suggested as an adjunct to protective mechanical ventilation for patients with very severe ARDS. The methods of the disclosure can be performed in combination with any of the above therapies for treatment or prevention of ARDS.

In some examples, the other therapy is one that is used to treat the underlying cause of ARDS. For instance, in one example, the other therapy comprises administration of an antiviral or antibiotic (e.g., where the underlying cause of ARDS is an infection). In one example, the other therapy comprises administration of remdesivir.

In one example, the compound that inhibits G-CSF signaling is administered simultaneously with the other therapy. In one example, the compound that inhibits G-CSF signaling is administered before the other therapy. In one example, the compound that inhibits G-CSF signaling is administered after the other therapy.

In some examples, the compound that inhibits G-CSF signaling is administered in combination with a cell. In some examples, the cell is a stem cell, such as a mesenchymal stem cell. In some examples, the compound that inhibits G-CSF signaling is administered in combination with a gene therapy.

Dosages and Timing of Administration

Suitable dosages of compounds of the present disclosure will vary depending on the specific compound and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment, data from cell culture assays or animal models can are used, wherein a suitable dose is within a range of circulating concentrations that include the $ED_{50}$ of the active compound with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

In some examples, the compound that inhibits G-CSF signaling is administered systemically. In some examples, the compound that inhibits G-CSF signaling is administered locally.

In some examples, a method of the present disclosure comprises administering a therapeutically effective amount of a compound described herein.

The term "therapeutically effective amount" is the quantity which, when administered, improves the prognosis and/or state of the subject and/or that reduces or inhibits one or more symptoms of ARDS to a level that is below that observed and accepted as clinically diagnostic or clinically characteristic of that condition. Alternatively, a therapeutically effective amount is a quantity which, when administered prevents the occurrence or exacerbation of one or more symptoms of ARDS. The amount to be administered will depend on the particular characteristics of the subtype of ARDS to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of compound, rather the present disclosure encompasses any amount of the compound that inhibits G-CSF signaling sufficient to achieve the stated result in a subject. In one example, a therapeutically effective amount of the compound that inhibits G-CSF signaling does not induce neutropenia.

In some examples, a method of the present disclosure comprises administering a prophylactically effective amount of a compound described herein. As used herein, the term "prophylactically effective amount" shall be taken to mean a sufficient quantity of a compound to prevent or inhibit or delay the onset of one or more detectable symptoms of ARDS. The skilled artisan will be aware that such an amount will vary depending on, for example, the specific compound administered and/or the particular subject and/or the type or severity or level of condition and/or predisposition (genetic or otherwise) to the condition. Accordingly, this term is not to be construed to limit the present disclosure to a specific quantity, e.g., weight or amount of compound, rather the present disclosure encompasses any amount of the compound that inhibits G-CSF signaling sufficient to achieve the stated result in a subject. In one example, a prophylactically effective amount of the compound that inhibits G-CSF signaling does not induce severe neutropenia.

For in vivo administration of the compounds described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In one example, the protein is administered at a dose of between 0.1 mg/kg and 1 mg/kg. In an example, the protein is administered at a dose of between 0.1 mg/kg and 0.9 mg/kg, for example, between 0.1 mg/kg and 0.8 mg/kg, for example between 0.1 mg/kg and 0.6 mg/kg. As used in this context, the term "between" includes the values recited at each end of the range specified.

In one example, the protein is administered at a dose of between 0.1 mg/kg and 0.8 mg/kg. In one example, the protein is administered at a dose of between 0.3 mg/kg and 0.6 mg/kg. In one example, the protein is administered at a dose of between of 0.1 mg/kg and 0.6 mg/kg. In one example, the protein is administered at a dose of 0.1 mg/kg or 0.3 mg/kg or 0.6 mg/kg. In one example, the protein is administered at a dose of about 0.1 mg/kg. In one example, the protein is administered at a dose of about 0.2 mg/kg. In one example, the protein is administered at a dose of about 0.3 mg/kg. In one example, the protein is administered at a dose of about 0.4 mg/kg. In one example, the protein is administered at a dose of about 0.5 mg/kg. In one example, the protein is administered at a dose of about 0.6 mg/kg. In one example, the protein is administered at a dose of about 0.7 mg/kg. In one example, the protein is administered at a dose of about 0.8 mg/kg.

In some examples, the protein is administered multiple times. Where multiple doses are administered, any of the above doses can be combined.

In some examples, subsequent doses are separated by 2 to 5 days. The period of time separating each subsequent dose can be the same or different.

In some examples, the compound that inhibits G-CSF signaling is administered with a loading dose which is higher than a subsequent one or more maintenance dose(s).

In the case of a subject that is not adequately responding to treatment, multiple doses in a week may be administered. Alternatively, or in addition, increasing doses may be administered.

In another example, for subjects experiencing an adverse reaction, the initial (or loading) dose may be split over numerous days in one week or over numerous consecutive days.

Administration of a compound according to the methods of the present disclosure can be continuous or intermittent, depending, for example, on the recipient's physiological condition, whether the purpose of the administration is therapeutic or prophylactic, and other factors known to skilled practitioners. The administration of a compound may be essentially continuous over a preselected period of time or may be in a series of spaced doses, e.g., either during or after development of a condition.

In another example, the compound that inhibits G-CSF signaling is administered in an amount sufficient to reduce circulating neutrophils in the subject without causing grade 3 or grade 4 neutropenia for greater than seven consecutive days.

Kits

Another example of the disclosure provides kits containing compounds useful for the treatment or prevention of ARDS as described above.

In one example, the kit comprises (a) a container comprising a compound that inhibits G-CSF signaling as described herein, optionally in a pharmaceutically acceptable carrier or diluent; and (b) a package insert with instructions for treating, preventing, or reducing an effect of ARDS in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating or preventing the ARDS and may have a sterile access port (for example, the container may be an intravenous solution bag or a vial having a stopper pierceable by a hypodermic injection needle). At least one active agent in the composition is the compound that inhibits G-CSF signaling. The label or package insert indicates that the composition is administered to a subject eligible for treatment, e.g., one having or at risk of developing ARDS, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/ or dextrose solution. The kit may further include other materials desirable from a commercial and user standpoint, including other buffers, diluents, filters, needles, and syringes.

The present disclosure includes the following non-limiting Examples.

EXAMPLES

Example 1: Safety, Pharmacokinetics (PK) and Pharmacodynamics (PD) of C1.2G, an Antibody that Binds to G-CSFR, Administered to Healthy Adult Subjects A Phase 1 clinical trial was conducted to assess the safety and tolerability of single ascending dose (Parts A and B) and repeated (Part C) intravenous (IV) infusions of CSL324 (also referred to as C1.2G herein) in healthy subjects.

Method

The trial was a first-in-human, single center, randomized, double-blind, placebo-controlled study assessing the safety, tolerability, PK, and pharmacodynamics (PD) of single ascending doses and repeat doses of IV CSL324 in healthy human subjects. The study consisted of 3 parts. Parts A, B, and C. Regular blinded review of safety, tolerability, PK, and selected PD data was conducted by the Safety Review Committee (SRC) to guide dose selection. This trial is described at the Australian New Zealand Clinical Trials Registry (ANZCTR) under Registration Number ACTRN12616000846426, title: "Dose escalation, placebo-controlled phase 1 study to assess the safety and tolerability of CSL324 in healthy adults".

Part A: Single Ascending Dose

Part A assessed single ascending doses of CSL324 administered to 5 sequential cohorts (Cohorts A1 to A5). Each cohort comprised 6 subjects randomized to receive either CSL324 (n=4) or placebo (n=2) on Day 1. Single ascending doses of 0.1, 0.3, 1.0, 3.0, and 10 mg/kg of CSL324 were planned for the 5 sequential cohorts. At the recommendation of the SRC, the highest dose administered was 1.0 mg/kg of CSL324 (Cohort A3); Cohorts A4 and A5 received intermediate doses of 0.6 and 0.8 mg/kg CSL324, respectively. Subjects were followed up until Day 85.

Part B—Single Ascending Dose with G-CSF Challenge

Part B assessed single doses of CSL324 during a G-CSF challenge. Cohorts B1, B2, and B3 each comprised 4 subjects randomized to receive either CSL324 (n=3) or placebo (n=1) on Day 1. Cohort B1 received 0.1 mg/kg CSL324, and Cohorts B2 and B3 received 0.3 and 0.8 mg/kg CSL324, respectively, at the recommendation of the SRC. Subjects were administered a G-CSF challenge (5 μg/kg filgrastim) before and after CSL324 (on Days −3, −2, −1, 1, 2, and 3). Cohort B4 comprised 6 subjects randomized to receive either CSL324 (n=4) or placebo (n=2) on Day 1. Subjects received 0.8 mg/kg CSL324 and were administered a G-CSF challenge (5 μg/kg filgrastim) after CSL324 only (on Days 2, 3, and 4) Subjects were followed up until Day 85.

Part C—Repeat Dose

Part C assessed 3 repeat doses of CSL324 administered at 21-day intervals (Days 1, 22, and 43). Ten subjects were randomized to receive either CSL324 (n=6) or placebo (n=4). Subjects were administered 0.6 mg/kg CSL324 at the recommendation of the SRC. Subjects were followed up until Day 126.

Safety, Pharmacokinetic (PK), and Pharmacodynamic (PD) Assessments

In all study parts, safety assessments included adverse events (AEs), vital signs including orthostatic challenge, physical and neurological examination, 12-lead electrocardiogram (ECG), cardiac monitoring using ECG telemetry, clinical laboratory tests (hematology, blood chemistry, coagulation, and urinalysis), fatigue measured on a visual analogue scale, and CSL324 immunogenicity.

CSL324 was measured in serum (all cohorts) and cerebrospinal fluid (Cohort A5 only).

PD assessments included neutrophil functional attributes (phagocytic activity, oxidative burst activity, G-CSF receptor phospho-signal transducer and activator of transcription-3 [pSTAT-3] signaling [Part A only], and granulocyte macrophage colony stimulating factor [GM-CSF] receptor pSTAT-3 signaling [Parts A and C only]); neutrophil G-CSF receptor occupancy/saturation (Parts A and C only); and serum G-CSF, cytokines, and chemokines.

Diagnosis and Main Criteria for Inclusion

Healthy male or female subjects, 18 to 55 years of age, with body mass index of 18.5 to 32.0 kg/m2 (inclusive) and weight ≥50 kg and <100 kg, who provided written informed consent. Female subjects were to be of non-childbearing potential; male subjects and their female spouse/partner of childbearing potential were to use 2 forms of highly effective birth control from Screening until 90 days after the final IV infusion.

Subjects were excluded if they had a history or evidence of any clinically significant cardiovascular, gastrointestinal, endocrine, hematologic, hepatic, immunologic, metabolic, urologic, pulmonary, neurologic, dermatologic, psychiatric, renal and/or other major disease or malignancy, as judged by the Investigator; a history of venous thrombosis, polycythemia, or thrombophilia; a history of autoimmune disease; cyclic neutropenia or a Screening absolute neutrophil count (ANC) $<2.0\times10^9$/L; any clinically significant abnormality identified at Screening or site admission; pulse rate <40 or >100 beats per minute, mean systolic blood pressure >145 mmHg, or mean diastolic blood pressure >90 mmHg at Screening or site admission, mean corrected QT interval using Fridericia's formula >450 msec at Screening; or use of any prescribed or non-prescribed drugs in the 10 days before IV infusion, except for the occasional use of paracetamol (up to 2 g/day). For Parts A and B only, subjects were excluded if they had any tattoo or compromised skin health, or a history of keloid formation, hypertrophic scarring, or lymphangitis.

CSL324 Antibody Dose and Mode of Administration

CSL324 was provided as a sterile solution for injection in 10 ml, vials. CSL324 was administered IV at a volume determined by the subject's weight on Day 1 and cohort dose.

Placebo, 0.9% sodium chloride, was administered IV at an equivalent volume to CSL324 according to the subject's weight on Day 1 and cohort dose.

All CSL324 infusions were to be given over 60±5 minutes in a forearm vein using a syringe pump (doses ≤1.0 mg/kg).

Duration of Treatment

Subjects in Parts A or B received CSL324 or placebo as a single dose on Day 1, and were followed up until Day 85. Subjects in Part C received 3 doses of CSL324 or placebo at 21-day intervals on Days 1, 22, and 43, and were followed up until Day 126.

Criteria for Evaluation:

Primary endpoint: Incidence, causality, and severity of AEs during the study.

Secondary Endpoints:

Pharmacokinetic parameters of CSL324 in serum:

Parts A and B:

$AUC_{0-inf}$—Area under the concentration-time curve from time 0 extrapolated to time infinity $AUC_{0-4}$—Area under the concentration-time curve from time 0 to collection time t $C_{max}$— Maximum concentration $CL_{tot}$—Total systemic clearance after IV dosing $t_{max}$—Time of maximum concentration $t_{1/2}$—Terminal elimination half-life $V_z$—Volume of distribution after IV dosing during the terminal elimination phase Part C:

$AUC_{0-4}$—Area under the concentration-time curve from time 0 to collection time t $AUC_{0-tau}$—Area under the concentration-time curve during dosing interval at steady state $C_{min,ss}$—Minimum (trough) concentration at steady state $C_{max,ss}$—Maximum concentration at steady state $t_{max,ss}$—Time of maximum concentration at steady state $t_{1/2,ss}$—Terminal elimination half-life at steady state $CL_{tot,ss}$—Total systemic clearance at steady state after IV dosing $V_{z,ss}$—Volume of distribution at steady state after IV dosing during the terminal elimination phase Concentrations of CSL324 and of G-CSF in cerebrospinal fluid (Cohort A5 only).

Presence of anti-CSL324 antibodies in serum.

Non-compartmental PD parameters for ANC, including the maximum effect ($E_{max}$) of ANC from Day 1 and the area under the effect curve from time 0 to 24 hours for ANC ($AUEC_{0-24,ANC}$), after G-CSF challenge following CSL324 or placebo dosing (Part B only).

Statistical Methods

Analysis Populations

The Full Analysis Set (FAS) comprised all subjects who provided written informed consent and who were eligible for inclusion in the study after Screening. The FAS was used for demographics, baseline characteristics, and immunogenicity. The Safety Population comprised all subjects who received at least 1 dose of CSL324, analyzed according to the dose and medication received, and was used for all safety analyses.

The PK Population comprised all subjects who received at least 1 dose of CSL324 and had at least 1 measured PK concentration, and was used for all PK analyses.

The PD Population comprised all subjects who received at least 1 dose of CSL324 and for whom PD data were available before CSL324 infusion and for at least 1 time point after CSL324 infusion. The PD Population was used for all PD analyses.

General Considerations

All data were listed by subject. Summary statistics were presented using descriptive statistics. All statistical tests were 2-sided and performed at the 5% level of significance, unless otherwise stated.

Pharmacokinetic (PK) Analyses

PK parameters were derived from serum CSL324 concentrations by standard noncompartmental analysis using actual sampling times. Dose proportionality was assessed for the PK parameters $C_{max}$, $AUC_{0-4}$, and $AUC_{0-inf}$ for the single dose cohorts in Part A and Part B separately. Dose proportionality was analyzed using a power model which included loge-transformed body weight-adjusted dose level as an independent variable. Linear proportionality between the PK parameter and dose could be declared if the 90% confidence interval (CI) was within the critical interval of 0.85 to 1.15. Correlation of PK parameters $C_{max}$, $AUC_{0-4}$, and $AUC_{0-inf}$ with total dose (mg) and body weight-adjusted dose (mg/kg) was investigated for Part A and Part B using Pearson correlation analysis.

The relative bioavailability of CSL324 without (Part A) and with (Part B) co-administration of G-CSF was assessed using a mixed-effect model (with treatment as fixed effect and subject as random effect) and the loge-transformed PK parameters $C_{max}$, $AUC_{0-4}$, and $AUC_{0-inf}$. Administration of CSL324 without (Part A) and with (Part B) co-administration of G-CSF was considered equivalent if the 90% CI for the geometric mean ratio was between 80% and 125% for any comparison.

Attainment of steady state after 3 doses of CSL324 every 21 days (Part C) was assessed by repeated measures analysis of variance (ANOVA) of minimum trough concentration (Cmin). The first non-significant comparison was the dosing interval at which steady state was attained.

Pharmacodynamic (PD) Analyses

PD parameters were derived using standard noncompartmental analysis. The PD parameters for serum cytokine and chemokine concentrations, neutrophil phagocytic and oxidative burst activity, G-CSF receptor occupancy, and pSTAT-3 signaling for Part A were compared between each CSL324 dose in Part A and the pooled placebo group for Part A by ANOVA.

Correlation of PD parameters with CSL324 total dose (mg) and body weight-adjusted dose (mg/kg) was investigated using Pearson correlation analysis.

Safety Analyses

Treatment-emergent AEs (TEAEs) were coded using Medical Dictionary for Regulatory Activities (MedDRA; Version 20.1). The severity of each TEAE was assessed by the Investigator using the National Cancer Institute Common Terminology Criteria for Adverse Events Version 4, except for TEAEs of abnormal ANC values which were graded using Club Phase 1 criteria. Box plot comparisons between subjects with cumulative positive and negative immunogenicity results were done for CSL324 clearance (CLtot or CLtot,ss) and selected PD parameters (ANC and G-CSF concentration).

Results

Subject Disposition

A total of 58 subjects provided informed consent and were randomized into the study. In Part A (n=30), 4 subjects received CSL324 and 2 subjects received placebo in each of the 5 cohorts (Cohorts A1 to A5). In Part B (n=18), 3 subjects received CSL324 and 1 subject received placebo in each of Cohorts B1 to B3, and 4 subjects received CSL324 and 2 subjects received placebo in Cohort B4. In Part C (n=10), 6 subjects received CSL324 and 4 subjects received placebo.

Overall, 55 subjects (94.8%) completed the study; 1 placebo-treated subject was discontinued from Part A (Cohort A5) due to withdrawn consent, and 2 subjects (1 CSL324-treated and 1 placebo-treated) were discontinued after completing the 3 doses in Part C due to other reasons. Two subjects who completed Part C of the study did not receive CSL324 Dose 3 at the recommendation of the SRC.

Demographics

Study subjects were male (100%) and predominantly White (65.5%), with a mean age of 30.3 years (range: 19 to 54 years). There were no major differences in demographic characteristics between subjects in Parts A, B, or C Overall, the subject medical and surgical histories were consistent with a healthy volunteer population.

Pharmacokinetics (PK)

Figure 1:
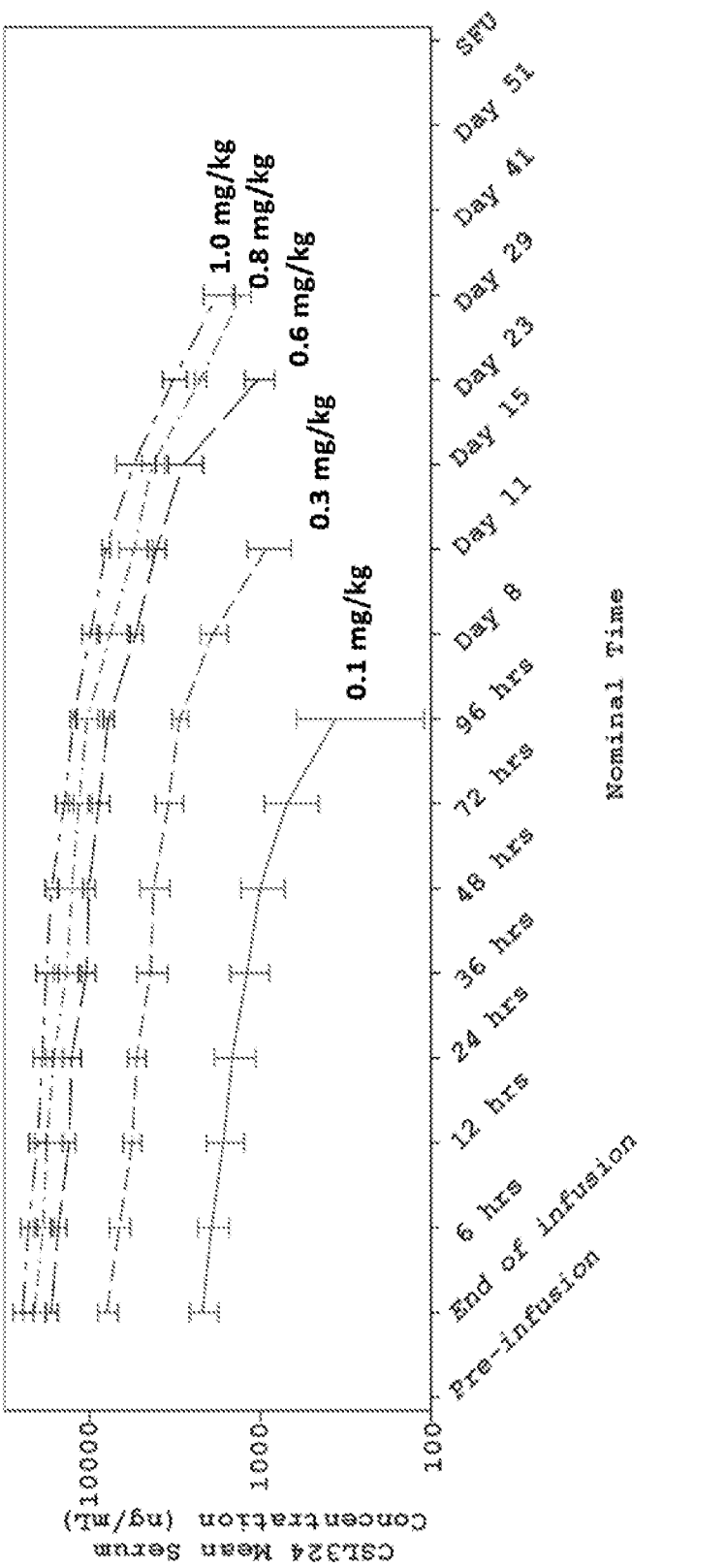
FIG. 1 is a graph which illustrates mean serum CSL324 concentrations over time in healthy subjects administered a single dose of 0.1, 0.3, 0.6, 0.8, and 1.0 mg/kg CSL324, as described in Example 1.

After single IV doses of CSL324, mean serum CSL324 concentrations peaked at the end of infusion, with $C_{max}$ showing linear proportionality to CSL324 dose (FIG. 1). Exposure to CSL324, measured as $AUC_{0-4}$ and $AUC_{0-inf}$, increased with higher CSL324 doses but did not demonstrate dose linearity as the confidence limits for both parameters were outside the 0.85 to 1.15 critical interval (estimated slope 1.68 [90% CI: 1.58 to 1.79] for $AUC_{0-4}$ and 1.67 [90% CI: 1.56 to 1.78] for $AUC_{0-inf}$). Mean $CL_{tot}$ of CSL324 was not constant across the range of doses tested, decreasing by 80% with a 10-fold increase in CSL324 dose.

After single TV doses, mean tin ranged from 40.5 hours with 0.1 mg/kg CSL324 to 206 hours with 1.0 mg/kg CSL324. After 3 doses of 0.6 mg/kg CSL324, administered at 21-day intervals, mean $t_{1/2}$ was 251 hours.

Administration of G-CSF before and after CSL324 infusion lowered the relative bioavailability of single CSL324 doses, measured as $AUC_{0-inf}$ and $AUC_{0-4}$, and had minimal effect on $C_{max}$. The reduction in CSL324 exposure by G-CSF was greater when G-CSF was administered before and after CSL324 dosing compared with after CSL324 dosing only.

Steady state was not achieved after 3 doses of 0.6 mg/kg CSL324 administered at 21-day intervals based on trough concentrations. Peak mean serum CSL324 concentrations were similar after Dose 1 and Dose 3.

CSL324 was not detectable in cerebrospinal fluid after a single 0.8 mg/kg CSL324 dose.

Pharmacodynamics

Mean ANC decreased after single and repeat CSL324 doses, administered without G-CSF challenge, when compared with placebo. Across the single CSL324 doses, mean ANC minimum effect ($E_{min}$) was lowest with the 1.0 mg/kg CSL324 dose ($1.3 \times 10^9$/L) and highest with placebo ($2.49$-$10^9$/L). Mean ANC $E_{min}$ decreased to $1 \times 10^9$/L after repeat CSL324 dosing, with $E_{min}$ occurring after Dose 3 (at approximately Day 48).

Higher doses of CSL324 (0.3 and 0.8 mg/kg) inhibited the G-CSF-mediated stimulation of elevated ANC; the ANC response to G-CSF challenge was similar with 0.1 mg/kg CSL324 and placebo. ANCs were negatively correlated with CSL324 dose and CSL324 exposure, based on $AUC_{0-4}$.

CSL324 had no apparent effects on neutrophil function when measured ex vivo as neutrophil phagocytic and oxidative burst activity. Higher single doses of CSL324 (0.3 to 1.0 mg/kg) increased the G-CSF half-maximal effective concentration (EC50) for ex vivo stimulation of neutrophil pSTAT-3 signaling compared with placebo; however, the assay data showed large variability, limiting interpretation. No consistent effect of CSL324 was seen on the ratio of GM-CSF stimulated versus unstimulated neutrophil pSTAT-3 signaling.

Figure 2:
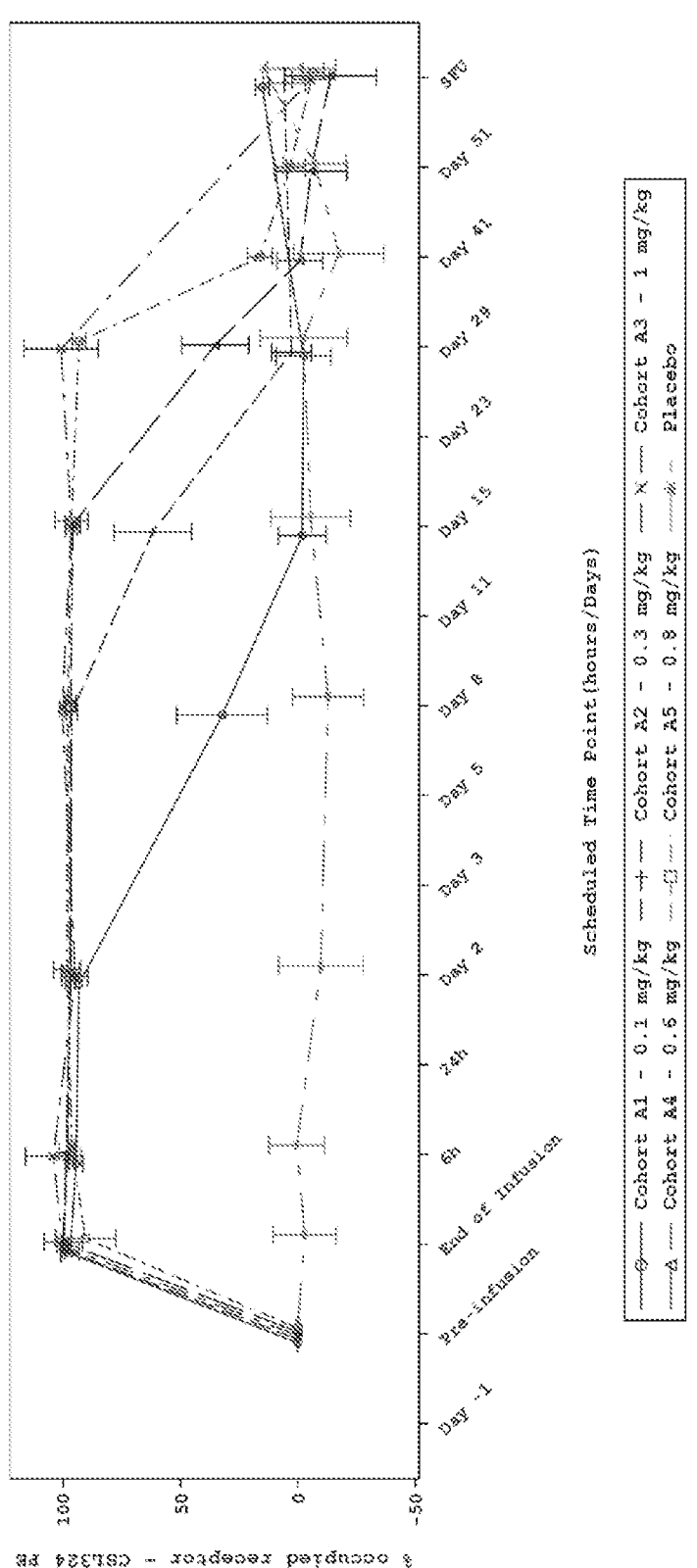
FIG. 2 is a graph which illustrates percent occupied target receptor (G-CSFR) over time in healthy subjects administered a single dose of 0.1, 0.3, 0.6, 0.8, and 1.0 mg/kg CSL324, as described in Example 1.

Neutrophil G-CSF receptor saturation was achieved rapidly with single CSL324 doses from 0.1 to 1.0 mg/kg. The duration of approximately 100% receptor occupancy increased with increasing CSL324 dose, lasting until Day 3 with 0.1 mg/kg CSL324 and until Day 29 with 0.8 and 1.0 mg/kg CSL324 (FIG. 2).

Single CSL324 doses increased peak serum G-CSF concentrations and exposure compared with placebo, with G-CSF $AUEC_{0-4}$ and $AUEC_{0-24}$ showing a positive correlation with CSL324 systemic exposure and dose. Repeat CSL324 doses produced a sustained increase in serum G-CSF, with peak concentrations occurring 2 days after each dose. G-CSF was not detectable in cerebrospinal fluid after a single 0.8 mg/kg CSL324 dose.

Serum concentrations of cytokines and chemokines showed no clear patterns over time after CSL324 dosing in comparison with placebo. Serum interleukin (IL)-8 concentrations showed small increases with CSL324 and placebo, suggesting an effect of the TV infusion. Serum IL-1 receptor antagonist (IL-IRA) levels increased after G-CSF challenge and then decreased after administration of the higher CSL324 doses (0.3 to 1.0 mg/kg).

Safety

Overall, the frequency of TEAEs was similar with CSL324 (82.10%) and placebo (94.7%). Treatment-related TEAEs occurred for 64.1% of subjects in the overall CSL324 group and 57.9% in the placebo group. TEAEs that occurred more frequently with CSL324 than with placebo were Neutropenia (19.2% versus no subjects), Infusion site pain (7.7% versus no subjects), and Nasal congestion (7.7% versus no subjects). No TEAEs were serious or fatal. Two subjects did not receive Dose 3 at the recommendation of the SRC.

There was no CSL324 dose-dependent trend in overall TEAE frequency across dose cohorts. All subjects (100%) experienced TEAEs after repeat dosing with CSL324 or placebo.

The majority of TEAEs were Grade 1 or 2 All treatment-related TEAEs after CSL324 treatment had resolved by the Safety Follow-up Visit, except for one TEAE of Grade 2 Erythema which was ongoing.

CSL324 reduced ANC in a dose-dependent manner, characterized by neutropenia up to Grade 3 severity, which resolved spontaneously the following day (FIG. 3 and FIG. 4).

One subject had a TEAE of Grade 3 Neutropenia on Day 4 after a single dose of 1.0 mg/kg CSL324 (FIG. 3) and 4 subjects had 7 TEAEs of Grade 3 Neutropenia with repeat 0.6 mg/kg CSL324 doses (FIG. 4). Two subjects who experienced more than 1 event of Grade 3 Neutropenia did not receive CSL324 Dose 3 in Part C at the recommendation of the SRC after review of available safety, tolerability, PK, and selected PD data. All TEAEs of Grade 3 Neutropenia resolved spontaneously without treatment by the next day.

ANCs meeting the criteria for neutropenia Grade 2 or 3 were experienced by 6 of 20 subjects treated with a single CSL324 dose, and tended to occur within 1 to 4 days after CSL324 dosing. Five of 6 subjects who received repeat CSL324 doses had ANCs meeting the criteria for neutropenia Grade 2 or 3, which tended to occur after Dose 3.

No infusion reactions or local tolerability reactions were observed. TEAEs of infusion site pain, puncture site erythema, and puncture site pain were experienced by 5% of CSL324-treated subjects and no placebo-treated subjects.

No safety signals were identified from laboratory parameters, vital signs including orthostatic challenge, ECG, physical findings, or fatigue scores.

No subjects developed anti-CSL324 antibodies after single and repeat IV dosing.

Conclusions

CSL324 was safe and well tolerated when administered as a single dose up to 0.8 mg/kg or as repeat doses of 0.6 mg/kg at 21-day intervals. CSL324 reduced ANC levels in a dose-dependent manner, characterized by neutropenia up to Grade 3 severity which resolved spontaneously without treatment by the next day. Systemic CSL324 exposure increased with increasing dose, with $C_{max}$ showing linear proportionality to CSL324 dose. Higher CSL324 doses had a longer $t_{1/2}$ and slower $CL_{tot}$. CSL324 showed rapid G-CSF receptor saturation and inhibited the G-CSF-mediated stimulation of ANC at higher doses, with minimal effects on inflammatory mediators. weeks post last dose) and the follow up assessment.

Example 2—CSL324 Reduces Neutrophil Migration Associated with CXCR1 Expression CSL324 Reduces CXCR1 and CXCR2 Expression Induced by G-CSF Whole blood samples obtained from healthy human donors were used to assess the expression of chemokine receptors CXCR1 and CXCR2 on neutrophils and to assess the effects of CSL324 in the presence or absence of G-CSF on the levels of these migratory receptors. Samples were pre-incubated with 1 mg/mL of CSL324 for 30 minutes prior to the stimulation of the cells with recombinant human G-CSF (30 ng/mL; n=11) or recombinant human GM-CSF (30 ng/mL; n=4) and cultured for 20 hours at 37° C., 5% C02. Neutrophils were identified by high side scatter (SSC) and the CD11b+CD49d-phenotype. The mean fluorescence intensity of conjugated antibodies to CXCR1 or CXCR2 was normalized relative to cells cultured in media alone.

Figure 5A:
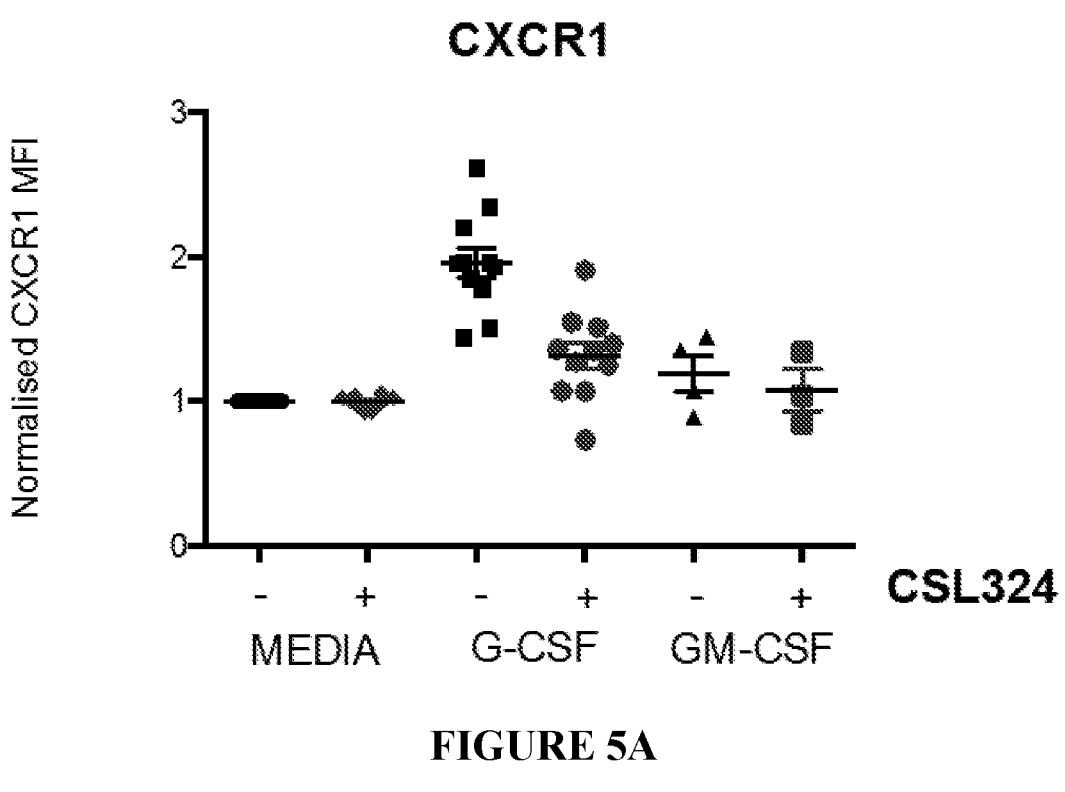
FIG. 5 shows graphs illustrating the effect of CSL324 on G-CSF-induced CXCR1 (FIG. 5A) and CXCR2 (FIG. 5B) expression on neutrophils. CSL324 (grey) did not alter the expression of either CXCR1 or CXCR2 compared to media alone, in the absence of G-CSF. Culture of neutrophils in the presence of G-CSF alone (black) increased the cell surface expression of CXCR1 and CXCR2 compared to media alone. Pre-incubation with CSL324 (grey) was able to reduce the G-CSF induced up-regulation of CXCR1 and CXCR2 expression.
Figure 5B:
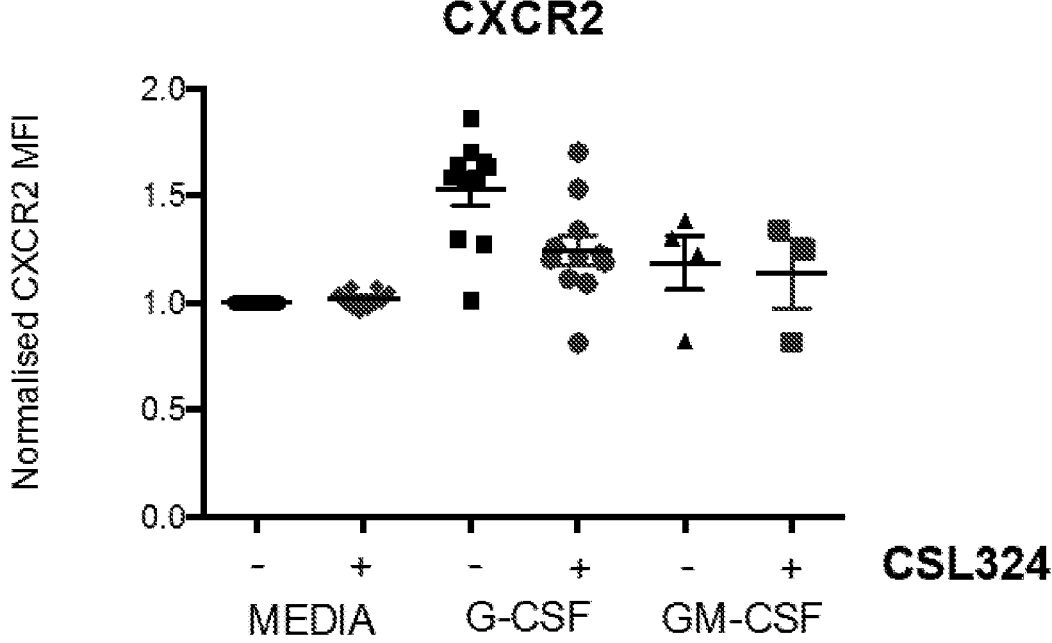

As shown in FIG. 5, culture of neutrophils with G-CSF alone (black) increased the cell surface expression of CXCR1 and CXCR2 compared to media alone. Pre-incubation with CSL324 (grey) caused a reduction in the G-CSF induced up-regulation of CXCR1 and CXCR2, with the mean fluorescence intensity (MFI) of CXCR1 or CXCR2 staining comparable to that seen when neutrophils were incubated in cell culture media alone. Culture of cells in the presence of GM-CSF did not significantly alter the levels of surface markers, and further, was not altered by the pre-incubation of samples with CSL324.

CSL324 Reduces Cell Migration Induced by G-CSF

A cell migration assay was used to assess the ability of CSL324 to inhibit G-CSF mediated neutrophil migration towards MIP-2. Specifically, purified neutrophils were isolated (>95% purity) and pre-cultured with or without 1 μg/mL CSL324 for 30 minutes before being stimulated with 30 ng/mL human G-CSF or 30 ng/mL human GM-CSF overnight. Chemotaxis to MIP-2 (500 ng/mL) was measured using transwell inserts (5 μm pores).

As shown in FIG. 6, pre-incubation with G-CSF resulted in increased migration of neutrophils to MIP-2, which was reduced to the same levels as the media alone condition by pre-incubation with CSL324 (FIG. 6A, grey bars). The pro-migratory effects of GM-CSF were not inhibited by pre-incubation with CSL324, indicating specificity to the effects of engaging the G-CSF receptor. Pre-incubation with G-CSF resulted in up-regulation of CXCR1 and CXCR2 that correlated with increased migration of neutrophils to MIP-2 (FIGS. 6B and 6C).

Together, these data demonstrate that:

CXCR1 (and CXCR2) expression is positively correlated with neutrophil migration (FIGS. 6B and 6C);

CSL324 inhibits G-CSF-induced CXCR1 (and CXCR2) expression on neutrophils (FIGS. 5A and 5B); and CSL324 inhibits G-CSF-induced neutrophil migration (FIG. 6A).

Example 3—VR81 Reduces Lung Inflammation in an Animal Model or ARDS

Materials and Methods

Antibodies

VR81 is a mouse monoclonal IgG1κ antibody produced against the extracellular domain of murine G-CSFR and blocks G-CSF binding to G-CSFR as described (Campbell et al. *Journal of Immunology,* 197(11) (2016) 4392-4402). In this regard, VR81 is a mouse surrogate antibody for C1.2 and C1.2G described herein and in WO2012/171057 BM4 is a monoclonal mouse isotype IgG1u control antibody.

Animal Model of ARDS

Female C57BL/6 mice, aged 8-12 weeks were obtained from the Animal Resources Centre (ARC), Canning Vale, WA, Australia. Mice were anaesthetised and then intubated by intratracheal (i.t.) instillation of 3 µg LPS into the lungs. This was accomplished by gently inserting a cannula attached to a 50 µl Hamilton syringe into the mouth and then the trachea of the mouse. Mice were euthanised 24 h after LPS intubation by lethal injection of pentobarbital.

Both prophylactic and therapeutic protocols were evaluated. (i) Prophylactic protocol: Mice were administered 500 µg (25 mg/kg) VR81 or BM4 intravenously (i.v.) 24 h prior to the intubation of LPS. (ii) Therapeutic protocol: Mice were administered 500 µg (25 mg/kg) VR81 or BM4 intravenously (i.v.) 6 h after the intubation of LPS. For both protocols, lung inflammation (e.g., total cell counts), protein concentration and neutrophil elastase activity in BALF was assessed 24 h after LPS administration.

BALF was obtained by cannulating the trachea with a 20G catheter. Both lungs were lavaged three times (each aliquot 0.4 ml PBS); total returns averaged 0.9-1.1 ml/mouse.

Measurement of Cell Counts in BALF

Total cell numbers in BALF were first determined by counting with a haemocytometer. Differential counts were done on cytocentrifuged preparations (Cytospin 4; Thermo Scientific), fixed and stained with Geimsa (Sigma) Differential counts were based on counts of 200 cells using standard morphologic criteria to classify the cells as neutrophils, macrophages or lymphocytes. Counts were performed by a single observer blinded to the treatment groups.

Measurement of Total Protein in BALF

BALF was centrifuged at 4000 rpm for 5 min at 4° C. Total protein was measured in the cell-free supernatant using a Pierce m BCA protein assay kit (Thermo Scientific).

Measurement of Neutrophil Elastase Activity in BALF

Cell-free BALF samples were transferred to 96-well black fluorescence plates and incubated with chromogenic elastase substrate (Elastase V Substrate; Calbiochem) diluted in 0.1 M Tris buffer, pH 8.0, containing 0.5 M NaCl and 0.1 mM $Ca^{2+}$ at a final concentration of 70 µM. After 1 h incubation at 37° C., the fluorescent product was measured at an excitation wavelength of 390 nm and emission wavelength of 460 nm. Under these conditions, generation of fluorescent product was linear with respect to the enzyme concentration. Porcine pancreatic elastase (Sigma-Aldrich) was used at 2-200 nM as control. Results are expressed as arbitrary units.

Measurement of Wet-to-Dry Hug Weight Ratio

The lung wet-to-dry (W/D) weight ratio was used to evaluate edema formation in the lungs of mice administered with LPS. To determine W/D ratio, the left lung lobe was weighed on excision (wet weight) from the animal. The lung tissue was then dried in an oven at 60° C. for 5 days until a constant dry weight was achieved. The W/D weight ratio was calculated by dividing the wet weight by the dry weight.

VR81 Reduces Cell Counts in BALF

High cell counts in BALF are an indicator of lung inflammation and are associated with ARDS. The animal model of ARDS described above was used to assess the ability of VR81 to reduce the level of cells, both total cell and absolute immune cell counts, present in the lungs in response to LPS-induced inflammation.

FIG. 7 shows that administration of 500 µg/mouse of VR81 one day prior to LPS significantly reduced the total cell count in BALF relative to mice administered PBS (FIG. 7A) or the isotype control antibody, BM4 (FIG. 7B). Similarly, FIG. 8 shows that administration of VR81 significantly reduced absolute immune cell counts in BALF, relative to mice administered PBS The reduction in immune cell count included an approximate 70% decrease in the levels of neutrophils in response to VR81 administration.

VR81 Reduces Total Protein in BALF

High levels of total protein in BALF, like cell counts, are an indicator of lung inflammation and edema, which are both associated with ARDS. The animal model of ARDS described above was used to assess the ability of VR81 to reduce the level of total protein present in the lungs in response to LPS-induced inflammation.

FIG. 9 shows that administration of 500 µg/mouse of VR81 one day prior to LPS significantly reduced the total protein levels in BALF relative to mice administered PBS (FIG. 9A) or the isotype control antibody, BM4 (FIG. 9B).

VR81 Reduces Neutrophil Elastase Activity in BALF

Neutrophil elastase is an enzyme stored within cytoplasmic azurophilic granules in neutrophils and is released upon immune stimulation where it acts either as free protein or is associated with networks of extracellular traps (NET), causing inflammation and degradation of invading pathogens. Neutrophil elastase plays an important role in the development and progression of ARDS.

The animal model of ARDS described above was used to assess the ability of VR81 to reduce the level of neutrophil elastase activity in the lungs in response to LPS-induced inflammation. FIG. 10 shows that administration of 500 µg/mouse of VR81 one day prior to LPS significantly reduced the level of neutrophil elastase activity in BALF, relative to mice administered PBS (FIG. 10A) or the isotype control antibody, BM4 (FIG. 10B).

VR81 Reduces Wet-to-Dry Lung Weight Ratio

The animal model of ARDS described above was used to assess the ability of VR81 to reduce lung wet-to-dry (W/D) weight ratio in response to LPS-induced inflammation. W/D ratio can be used as a measure of lung edema.

FIG. 15 shows that administration of 500 µg/mouse of VR81 one day prior to LPS significantly reduced edema formation, as measured by W/D ratio, relative to mice administered the isotype control antibody, BM4.

VR81 Reduces Immune Cell Counts when Administered after Disease Onset

FIG. 11A shows that total cell count in BALF of mice administered 3 µg LPS intratracheally has significantly increased by 6 h after administration and peaks at 24 h after administration. Similarly, FIG. 11B shows that neutrophil elastase activity has also significantly increased after 6 h and peaks at 48 hours. These data show that disease progression occurs by 6 h after LPS administration in the mouse model of ARDS used in this Example.

To assess the therapeutic efficacy of VR81 after disease onset, mice were treated intravenously with 500 μg VR81 or the isotype control BM4 6 h after LPS administration. As shown in FIG. 12, there was a significant difference (P<0.0001) in neutrophil numbers in BALF between the VR81 and BM4 groups (Student's t-test); n=2 (PBS), 6 (BM4) and 7 (VR81) This experiment was repeated with similar results.

The results described above in this Example demonstrate that inhibition of G-CSF signalling using an anti-G-CSFR antibody is effective in reducing lung inflammation in an animal model of ARDS, when administered either before or after disease onset.

Example 4—a Phase 2, Multicenter, Double-Blind, Randomized, Placebo-Controlled Study to Evaluate CSL324 in ARDS Associated with Coronavirus Disease 2019 (COVID-19)

This study evaluates the safety and efficacy of CSL324 in severe COVID-19 patients. CSL324 is hypothesized to mitigate neutrophil mediated lung damage in COVID-19 patients by:

Attenuating heightened neutrophil trafficking into the lungs;

Blocking G-CSF-mediated neutrophil survival, thereby decreasing the lifespan of neutrophils infiltrating the lungs; and

Reducing neutrophil-derived inflammatory mediators, including IL-1 and IL-6, as well as, neutrophil extracellular trap formation, the latter known to activate the contact phase system, thereby exacerbating inflammation and causing vascular leakage.

Study Overview

This is a Phase 2, prospective, multicenter, randomized, double-blind, placebo controlled, parallel group study to evaluate the safety and efficacy of CSL324 administered IV in combination with standard of care (SOC) treatment in patients with COVID-19. The study consists of a Screening Period of up to 2 days and a Treatment Period of up to 28 days. Eligible subjects are randomly assigned to receive multiple IV doses of either CSL324 or placebo in addition to SOC treatment (CSL324+SOC or placebo+SOC) on Days 1, 4 and 8. The primary endpoint for this study is the incidence of endotracheal intubation or death prior to endotracheal intubation from randomization to Day 28.

Potential Risks and Benefits

The safety of CSL324 is known from an earlier study conducted in healthy subjects (Example 1) where CSL324 was administered intravenously.

Risks in COVID19 Patients

The potential risks of CSL324 TV administration and mitigation strategies are described in Table 1.

TABLE 1

| Potential Risks of CSL324 Intravenous Administration and | | |
| --- | --- | --- |
| Risk | Rationale/Summary of data | Mitigation strategies |
| 1. Neutropenia | Neutropenia was observed in the phase 1 CSL324_1001 study of healthy volunteers (Example 1), with a maximum severity of Grade 3 (ANC < 1.0 to 0.5 × 109/L), being observed in 1 subject administered a single dose of 1.0 mg/kg CSL324 and 4 subjects administered up to 3 repeat doses of 0.6 mg/kg CSL324. There were no clinical signs and symptoms reported concurrent with neutropenia. All episodes of neutropenia were transient and resolved spontaneously and no treatment was required. Neutropenia has not been observed in the ongoing CSL324_1002 study in patients with Hidradenitis suppurativa and palmoplantar pustulosis. Patients with severe COVID-19 have higher values (>7 × $10^9$/L) and may therefore may have a reduced risk of ANC values dropping below the lower limit of normal | Exclusion of subjects not meeting a minimum ANC value at Screening and before dosing with CSL324 ANC assessment prior to each dose Regular ANC assessments at scheduled time points up to the End of Study Visit (Day 28) Provision of a recombinant human GM-CSF as rescue medication for severe neutropenia Monitoring Grade 3 and 4 neutropenia as AESIs ANC-specific subject and study stopping and halting criteria |
| 2. Hospital acquired infections | There is a potential risk to develop an infection if neutropenia is prolonged. In the phase 1 CSL324_1001 (IV administration) study (Example 1): No evidence of an increased susceptibility to infection was noted CSL324 was shown to have no apparent effects on neutrophil function when measured ex vivo as neutrophil phagocytic activity (in an *Escherichia coli* assay) and | Monitoring for signs and symptoms of new or worsening infection throughout the study Monitoring Grade 3 and 4 infection as AESIs Exclusion criteria: Subjects who have procalcitonin levels above 0.25 ng/ml Procalcitonin assessment prior to each dose Infection-specific halting criteria |

TABLE 1-continued

| Potential Risks of CSL324 Intravenous Administration and | | |
| --- | --- | --- |
| Risk | Rationale/Summary of data | Mitigation strategies |
| | oxidative burst activity (in *Escherichia coli*, N-formylmethionyl-leucylphenylalanine, and phorbol myristate acetate assays) Nonclinical studies showed that the murine analogue of CSL324, VR81, did not worsen infection outcomes in viral (X31 influenza virus), fungal (*Candida albicans*), or bacterial (*Streptococcus pneumonia*) mouse models (ie, clearance of infectious load or impact on survival outcomes). | |
| 3. Systemic administration-related-reactions (SARR) | Administration of a mAb, such as CSL324, may be associated with the risk of systemic administration-related reactions, including hypersensitivity, anaphylactic shock, and AEs related to cytokine release, some of which can be serious and life threatening. | Administration will be performed in hospital under supervised conditions Monitoring and assessment Exclusion of subjects with known or suspected infusion related reaction to monoclonal antibodies or CSL324 or excipients Halting criteria related to the symptoms of systemic administration-related reactions Cytokine profiling and laboratory assessments included as part of pre- and post- dosing |
| 4. Local administration site reactions | IV injection of a mAb may result in AEs localized to the administration site (eg. Pain, erythema). Infusion site pain was seen in 7.7% of subjects in the CSL324_1001 clinical study (Example 1). There were no CSL324-related adverse findings at the injection sites in two preclinical repeat dose toxicity studies (APQ0045, APQ0046). | Monitoring and assessment (including photographs, if needed) of the administration site at scheduled time points |
| 5. Immunogenicity | All mAbs are potentially immunogenic, in addition to the possibility of immediate hypersensitivity responses. In Study CSL324_1001, no subjects had CSL324-emergent immunogenicity after single and repeat IV dosing. | ADA assessment at scheduled time points up to the End of Study Visit |

ADA = anti-drug antibody;
AE = adverse event;
AESI = adverse event of special interest;
ANC = absolute neutrophil count;
GM-CSF = granulocyte-macrophage colony-stimulating factor;
IV = intravenous;
mAb = monoclonal antibody;
SC = subcutaneous;
SRC = safety review committee.

Given the potential benefit of CSL324 in patients with COVID-19, and the risk mitigation strategies incorporated in this protocol (ie, predefined inclusion/exclusion criteria, subject, and study halting rules, monitoring of AESIs and regular medical monitoring including ANC and procalcitonin measurement), the associated benefit-risk assessment is considered acceptable. The benefit-risk profile of CSL324 is determined as data from patient studies (ongoing and planned) becomes available.

Primary Objective and Endpoint of Study

Primary Objective

The primary objective of the study is to evaluate the treatment benefit of CSL324 after IV infusion in patients with COVID-19.

Primary Endpoint

Incidence of endotracheal intubation or death prior to endotracheal intubation is the primary endpoint. This is assessed by the proportion of subjects progressing to endotracheal intubation or death prior to endotracheal intubation from randomization to Day 28.

Secondary Objectives and Endpoints of Study

Secondary Objectives

The secondary objectives of the study are:

1. To further evaluate the efficacy of CSL324

2. To evaluate the safety of CSL324

3. To evaluate the pharmacokinetics (PK) of CSL324

Secondary Endpoints

TABLE 2

Secondary endpoints

| Secondary Objective | Endpoint | Summary Measure |
|---|---|---|
| 1 | All-cause mortality | Proportion of deaths from all causes occurring from randomization to Day 28 |
| 1 | Incidence of endotracheal intubation | Proportion of subjects intubated from, randomization to Day 28 |
| 1 | Days alive and ventilator free | Median number of days subjects were alive and ventilator free |
| 1 | Hospital length of stay (LOS) | Median LOS in hospital |
| 1 | Clinical status as assessed on an 8-point National Institute of Allergy and Infectious Disease (NIAID) ordinal scale | Number and proportion of subjects with at least a 2-point improvement in the ordinal scale<br>Number and proportion of subjects within each of the categories of the ordinal scale |
| 1 | Use of continuous positive airway pressure (CPAP) or bilevel positive airway pressure (BiPAP) | Proportion of subjects using CPAP or BiPAP |
| 1 | Use of high-flow nasal cannula (HFNC) | Proportion of subjects using HFNC |
| 1 | Use of extracorporeal membrane oxygenation (ECMO) | Proportion of subjects using ECMO |
| 1 | Change in Sequential Organ Failure Assessment (SOFA) score | Median of maximum change from baseline in SOFA score<br>Median of average change from baseline in SOFA score |
| 2 | Adverse events (AEs)<br>Serious adverse events (SAEs)<br>Adverse events of special interest (AESIs)<br>Clinically significant abnormalities in laboratory assessment that are reported as AEs | Number and proportion of subjects experiencing the specified safety events |
| 2 | Anti-drug antibodies | Levels of anti-CSL324 antibodies in subjects administered CSL324 |
| 3 | CSL324 PK:<br>Maximum concentration ($C_{max}$)<br>Time to reach maximum concentration ($T_{max}$)<br>Area under the concentration-time curve (AUC) | Mean ($\pm$SD) and geometric mean (geometric percent coefficient of variation [CV %]) for all PK parameters except $T_{max}$<br>Median (minimum, maximum) for $T_{max}$ |

Exploratory Objectives and Endpoints of Study

Exploratory Objectives

The exploratory objectives of the study are:

To evaluate exploratory efficacy endpoints

To evaluate the pharmacodynamic (PD) profile of CSL324

To evaluate exploratory biomarkers in blood and tracheal aspirates in intubated patients (where available)

To explore the correlation of PK, PD and clinical outcome

Exploratory Endpoints

The exploratory clinical efficacy endpoints are as follows:

| Endpoint | Summary Measure |
|---|---|
| Time on mechanical ventilation | Median number of days subject require mechanical ventilation in intubated subjects |
| ICU LOS | Median LOS in ICU |

Pharmacodynamic and exploratory research biomarkers may include, but not limited to:

Change from baseline in ANC

Serum levels of pro-inflammatory cytokines (eg, IL-1, IL-6, IL-8, IL-18, TNF, G-CSF)

Serum levels of myeloperoxidase (MPO), neutrophil elastase (NE) alpha 1 protease inhibitor complexes, proteinase 3 (PR3) alpha 1 protease inhibitor complexes, as well as complexes of NE and PR3 with alpha-2-macroglobulin and NE-specific fibrinopeptides may help understand the status of in vivo neutrophil activation.

Serum levels of potential markers of lung injury (soluble form of receptor for advanced glycation end products [sRAGE] and plasminogen activator inhibitor-1 [PAI-1]) may reflect the degree of microvascular injury.

Whole blood mRNA analyses (including RNAseq)

These exploratory analyses are aimed at understanding the following:

Pathogenesis and severity of COVID-19

Correlations to clinical status and response to CSL324 treatment

Predictors of disease prognosis and response to CSL324

Response to CSL324

Pharmacology of CSL324

Safety of CSL324 in COVID-19 patients

Study Design

This is a Phase 2, prospective, multicenter, randomized, double blind, placebo controlled, parallel group study to evaluate the safety and efficacy of IV administration of CSL324, administered in combination with standard of care (SOC) treatment, in patients with COVID-19. Key elements of the study design are presented in FIG. 13 and Table 3.

TABLE 3

| Study design | |
| --- | --- |
| Study Type | Prospective/Interventional |
| Study Periods | Screening Period (≤2 days) |
| | Treatment Period (28 days) |
| Blinding Type | Double blind |
| Study Configuration | Parallel group |
| Method of Assignment to Treatment | Randomized in 1:1 ratio to |
| | CSL324 + SOC or placebo + SOC |

SOC = standard-of-care treatment

Aggregate data from groups of subjects are reviewed frequently by an Independent Data Monitoring Committee (IDMC), both early and at predetermined intervals during the conduct of the study, to ensure safety of subjects enrolled in the study Dose Rationale To maximize the potential clinical benefit of CSL324 in patients with COVID-19, a dose regimen is utilized that maximizes target engagement with the G-CSF receptor (~90% receptor occupancy) and demonstrates a decrease in circulating neutrophils for a period of approximately 14 days, but avoid neutropenia and maintain ANC above 1.5× $10^9$/L. CSL324 is administered by IV infusion at 0.3 mg/kg (NOAEL) as 100 mg/kg therefore supporting the proposed clinical doses with more than a 100-fold exposure margin for the anticipated clinical $C_{max}$ and AUC exposure.

Pharmacokinetics and safety of CSL324 was evaluated in a completed first-in-human (FIH), single-center, randomized, double-blind, placebo-controlled clinical study (CSL324_1001—Example 1) in healthy subjects. CSL324 was safe and well-tolerated when administered as a single dose up to the maximum tolerated dose of 0.8 mg/kg or as 3 repeated doses of 0.6 mg/kg at 21-day intervals. Transient Grade 3 neutropenia was observed in 1 subject (1 event) administered a single dose of 1 mg/kg CSL324, and 4 subjects (7 events) administered repeat doses of 0.6 mg/kg CSL324. To understand the relationship between CSL324 exposure and effects on circulating neutrophils, a semi-mechanistic population pharmacokinetic and pharmacodynamic model was developed that was able to describe the time course of receptor occupancy and ANC based on the observed data from the FIH study after single and repeat doses of CSL324.

This model was therefore used to predict receptor occupancy and ANC profiles for alternative dosing regimens for this study in COVID-19 patients. The predictions for receptor occupancy and ANC counts over time are shown in FIG. 14. The exposure associated with this dose regimen is below the exposure observed at the MTD in FIH study and GLP toxicology study (Study Number APQ0045) as listed in Table 4.

TABLE 4

| Predicted Exposures at Planned CSL324 Doses and Safety Margins Relative to the NOAEL in the Cynomolgus Monkeys and the MTD in Healthy Human Subjects | | | | | | |
| --- | --- | --- | --- | --- | --- | --- |
| Dose | $C_{max}$ [a] | $C_{max}$ Safety Margin | | AUC [a] | AUC Safety Margin | |
| (mg/kg) | (µg/mL) | NOAEL [b] | MTD [c] | (µg · h/mL) | NOAEL [b] | MTD [c] |
| 0.3 on Day 1 | 7.51 (±1.35) | 533.3 | 2.8 | 1260 (±499.2) | 327.8 | 3.2 |
| 0.1 on Day 4 | | | | | | |
| 0.1 on Day 8 | | | | | | |

AUC = area under the concentration-time curve;

$AUC_{0-168h}$ = area under the concentration-time curve from zero to 168 hours;

$C_{max}$ = maximum concentration;

IV = intravenous;

MTD = maximum tolerated dose;

NOAEL = no-observed-adverse-effect level.

[a] Simulated results: mean (±standard deviation)

[b] The safety margin was calculated using the mean $C_{max}$ of 4005 µg/mL on day 78 and mean $AUC_{0-168h}$ of 413,000 µg · h/mL at the twelfth week in female and male monkeys administered the NOAEL dose of 100 mg/kg CSL324 IV weekly for 12 weeks (Study Number APQ0045).

[c] The safety margin was calculated using the mean $C_{max}$ of 21.2 µg/mL and mean AUC of 4060 µg · h/mL in healthy male subjects administered the MTD dose of 0.8 mg/kg CSL324 IV (Study Number CSL324_1001).

on Day 1, 0.1 mg/kg on Day 4, and 0.1 mg/kg on Day 8. The dose regimen is selected based on safety, PK, and PD (RO and ANC) data observed in a phase 1 Study in healthy volunteers (CSL324_1001—Example 1), as well as the simulated results obtained from a semi-mechanistic population PK and PD model.

The nonclinical toxicology program, which covers the ICH requirements for development of a monoclonal antibody, includes a pivotal 12-week repeat-dose GLP study in cynomolgus monkeys evaluating doses of 1, 10, 30, and 100 mg/kg administered weekly as a 1-hour IV slow bolus injection. No CSL324-related adverse effects were identified in the study defining the no-observed-adverse-effect level Planned Number of Subjects PGP-25n This study enrolls a total of approximately 124 subjects.

Planned Study Duration

The duration of an individual subject's study participation is expected to be up to 31 days. This estimate is based on:

A Screening Period of up to 2 days

A Treatment Period of up to 28 days

The overall study duration (ie, first subject's screening visit to last subject's last study visit) is approximately 4.5 months.

Description of Investigational Medicinal Product CSL324

Key characteristics of CSL324 are described in Table 5.

TABLE 5

| Description of CSL324 | |
| --- | --- |
| Substance name | CSL324 |
| Active substance | Recombinant Anti-G-CSF Receptor Monoclonal Antibody |
| Storage | +2° C. to +8° C. |
| Dosage form | Sterile solution for infusion containing 10 mg/mL of CSL324 in 10-ml vials |
| Dosing regimen [a] | 0.3 mg/kg Treatment Period Day 1 [b] 0.1 mg/kg on Treatment Period Day 4 0.1 mg/kg on Treatment Period Day 8 |
| Route of administration | Intravenous infusion |
| Anatomic location of administration | Peripheral vein |

INN = international nonproprietary name
[a] Infusion time is to be approximately 1 hour
[b] Administration of the first dose of IMP is to occur ≤6 hours after randomization.

CSL324 is manufactured in accordance with ICH Good Manufacturing Practice (GMP) guidelines and local regulatory requirements.

Placebo

The placebo comparator is sterile normal saline (0.9% sodium chloride) that is commercially available and will be supplied by the study site (Table 6).

TABLE 6

| Description of placebo | |
| --- | --- |
| Substance name | Not applicable |
| Active substance | Normal saline (0.9% sodium chloride) |
| Trade name | Not applicable |
| Dosage form | Sterile solution for infusion |
| Route of administration | Intravenous infusion |

Rescue Medication/Procedure

Neutropenia

Sargramostim (Leukine®), a recombinant human granulocyte-macrophage colony-stimulating factor (GM-CSF), is used, if needed, to treat severe neutropenia.

Subjects who have severe neutropenia, as determined by the Investigator, at any time during the study are administered sargramostim, if clinically indicated for emergency granulopoiesis. Sargramostim is used because CSL324 does not antagonize the actions of GM-CSF, which can also support granulopoesis. If administration of GM-CSF (sargramostim) is being considered, consultation with a physician with expertise in the management of neutropenia and ideally the use of GM-CSFs, such as sargramostim, is strongly recommended. The dosage regimen of 250 μg/m$^2$/day sargramostim administered by IV infusion over 4 hours or by SC injection once daily may be used; however, other regimens may be used as advised by a physician familiar with the use of sargramostim. The full Leukine® US Prescribing Information provides further information on preparation and dosage and administration.

The appropriate treatment for any subject with a low ANC of clinical significance must always be guided by the medical judgement of the treating physician(s), and should include consultation with a physician with expertise in the management of neutropenia. Hospitalization should be considered if after discharge a subject has any signs or symptoms of infection or is at high risk for medical complications (ie, prolonged ANC <0.5×10$^9$/L for >7 days, clinically unstable, presence of uncontrolled comorbidity, or other subject-specific factors).

Management of subjects with low absolute neutrophil counts is summarized in Table 7.

TABLE 7

| Management of Subjects with Low Absolute Neutrophil Counts | |
| --- | --- |
| ANC | Action |
| 0.5 to ≤1.0 × 10$^9$/L | Monitor closely Repeat ANC test as soon as possible and every 1 to 2 days until ANC >1.0 × 10$^9$/L Monitor for signs and symptoms of infection (other than SARS-CoV2) and, if present, strongly recommend consulting a physician with expertise in the management of neutropenia. |
| <0.5 × 10$^9$/L | Repeat ANC test as soon as possible Monitor for signs and symptoms of infection (other than SARS-CoV2) and presence of aphthous ulcers and consider hospitalization (if patient has been discharged) Consultation with a physician with expertise in the management of neutropenia is strongly recommended Consider GM-CSF (sargramostim [Leukine ®]) [a] in subjects with risk factors for poor clinical outcomes resulting from febrile neutropenia or infection: Prolonged ANC <0.5 × 10$^9$/L for >10 days Profound (<0.1 × 10$^9$/L) neutropenia Age >65 years Pneumonia or other clinically documented infections Sepsis syndrome Invasive fungal infection Hospitalization at the time of the development of fever |

ANC = absolute neutrophil count:
GM-CSF = granulocyte-macrophage colony-stimulating factor.
[a] Dosage and administration: 250 μg/m$^2$/day administered by intravenous infusion over 4 hours or by subcutaneous injection once daily.

Eligibility Criteria

The study population is selected on the basis of the inclusion and exclusion criteria described in the sections below. Subject eligibility is reviewed and documented by an appropriately medically qualified member of the investigator's study team before subjects are included in the study.

Inclusion Criteria

To be enrolled and randomized into the study, a subject must meet all of the following inclusion criteria:

1. Capable of providing written informed consent (an individual legally permitted to make medical decisions on the subject's behalf can provide written informed consent)
2. Willing and able to adhere to all protocol requirements
3. Age ≥18 years at the time informed consent is obtained
4. Positive for SARS-CoV-2 infection determined by a diagnostic test approved by the Food and Drug Administration (FDA) or allowed under an emergency use authorization
5. Chest computed tomography (CT) scan or X-ray results confirming interstitial pneumonia
6. At least one of the following (subjects improving while on respiratory support still qualify):
   respiratory frequency >30 breaths per minute,
   Peripheral (capillary) oxygen saturation (SpO$_2$)≤93% on room air,
   ratio of arterial partial pressure of oxygen to fraction of inspired oxygen (PaO$_2$/FiO$_2$)<300, SpO$_2$/FiO$_2$ ratio<218 (if PaO$_2$/FiO$_2$ ratio is not available), or radiographic lung infiltrates >50%.

Exclusion Criteria

Subjects must not be enrolled into the study or randomly assigned to treatment if they meet any of the following exclusion criteria:

1. Currently enrolled, planning to enroll, or participated, within the last 30 days, in a clinical study requiring administration of an IMP, including expanded access or compassionate use Exceptions:

Administration of investigational product with emergency use authorization granted for treatment of COVID 19 (eg, remdesivir) is permitted Convalescent plasma as part of approved special access programs such as expanded access, emergency IND, or compassionate use is permitted 2. Pregnant or breastfeeding (female subjects)

3. Intubated and require mechanical ventilation (including ECMO) at the time of randomization Exception: use of HFNC oxygen and noninvasive ventilation are permitted 4. Endotracheal intubation is imminent, in the opinion of the investigator 5. In the opinion of the investigator, the subject is not expected to survive for more than 48 hours after admission 6. Presence of any of the following comorbid conditions prior to randomization and prior to SARS-CoV-2 infection:

a. New York Heart Association class 4 heart failure b. Stage 4 or greater end stage renal disease or require renal replacement therapy c. Biopsy proven cirrhosis, portal hypertension or hepatic encephalopathy d. Stage 4 malignancies e. Chronic lung disease requiring home oxygen f. Active TB 7. History or evidence of pulmonary alveolar proteinosis 8. Confirmed diagnosis or clinical suspicion of bacterial pneumonia or active uncontrolled bacterial, fungal, or non SARS-CoV-2 viral infection at Screening 9. ANC <5×10$^9$ cells/L (can be lowered after IDMC review of safety data, if CSL324-induced neutropenia is not assessed as a safety concern).

10. Currently receiving a prohibited therapy including G-CSF, GM-CSF or anti-IL-6/6R 11. Any clinical or lab abnormality or other underlying conditions (eg, psychological disorders, substance abuse) that would render the subject unsuitable for participation in the study, in the opinion of the investigator.

Additional and/or alternative exclusion criteria may include:

1. Subjects with a Do-Not-Intubate or Do-Not-Resuscitate order

2. Procalcitonin levels >0.25 ng/mL

3. Received any live virus or bacterial vaccination within 3 months before the administration of the first dose of CSL324 or has had a *bacillus* Calmette-Guerin (BCG) vaccination within 12 months before Screening 4. Known or suspected infusion-related reaction or hypersensitivity (per Common Terminology Criteria for Adverse Events [CTCAE]) to monoclonal antibody therapy, or hypersensitivity to the IMP or any excipients of the IMP 5. Male or female subject of childbearing potential either not using or not willing to use a highly effective method of contraception to avoid pregnancy or not sexually abstinent at any time during the study and for ≥3 months after administration of IMP Study Assessments The schedule of planned assessments through Day 28 is shown in Table 8 below.

TABLE 8

| | Schedule of assessments | | | | | | | | | | | |
|---|---|---|---|---|---|---|---|---|---|---|---|---|
| | | Treatment Period $^a$ | | | | | | | | | | |
| | Screening | Week 1 | | | | | | | | | | |
| | Week −1 | Day 1 | | | | | | | | | Week 2 | |
| | Day −2 | Before | After $^c$ | | Day | Day | Day | Day | Day | Day | Day | Day |
| | to Day 1 $^a$ | Dosing $^b$ | 90 min | 6 h | 2 | 3 | 4 | 5 | 6 | 7 | 8 | 9 |
| Written informed consent $^g$ | X | | | | | | | | | | | |
| Inclusion/exclusion criteria | X | | | | | | | | | | | |
| Confirm SARS-CoV-2 positive $^h$ | X | | | | | | | | | | | |
| Medical history/demographics | X | | | | | | | | | | | |
| Chest CT scan or X-ray $^i$ | X | | | | | | | | | | | |
| Physical examination $^j$ | X | | | | | | | | | | | |
| Height and body weight | X | | | | | | | | | | | |
| Pregnancy test $^k$ | X | | | | | | | | | | | |
| Urinalysis $^l$ | X | | | | | | | | | | | |
| Vital signs $^m$ | | X | X | X | X | X | X | X | X | X | X | X |
| Respiratory parameters $^n$ | | X | X | X | X | X | X | X | X | X | X | X |
| Assisted ventilation Parameters $^o$ | | | X | X | X | X | X | X | X | X | X | X |
| SOFA score | X | X | | | X | X | | X | | X | | |
| Randomization | | X | | | | | | | | | | |
| IRT Assignment to IMP kits $^p$ | | X | | | | | X | | | X | | |
| Administration of IMP $^q$ | | X $^r$ | | | | | X | | | X | | |
| Blood samples for laboratory testing — Local Hematology/ANC | X | X | X | X | X | X | X | X | X | X | X | X |
| Blood samples for laboratory testing — Biochemistry/ferritin | X | X | | | X | X | | X | | X | | |

TABLE 8-continued

Schedule of assessments

|  |  |  |  |  |  |  |  |  |  |  |  |  |
|---|---|---|---|---|---|---|---|---|---|---|---|---|
|  |  | Coagulation | X | X |  |  | X | X |  | X |  | X |  |
|  |  | Procalcitonin | X | X |  |  |  |  | X |  |  |  | X |
| Per | | Biomarkers [s] | X | X | X | X | X | X | X |  | X | X |
| CSL | ADA |  | X |  |  |  |  |  |  |  | X |  |
|  | RNA |  | X |  | X | X |  |  |  |  |  |  |
|  | PK [t] |  |  | X | X | X | X | X | X |  | X | X |
| Outcome assessments |  |  | X | X | X | X | X | X | X | X | X | X | X |
| AEs |  | X | X | X | X | X | X | X | X | X | X | X |
| Concomitant medication/therapy |  | X | X | X | X | X | X | X | X | X | X | X |

| | | | Treatment Period [a] | | | | | | | | |
|---|---|---|---|---|---|---|---|---|---|---|---|
| | | | Week 2 | | | | | Week 3 | | Week 4 | |
| | | | Day 10 | Day 11 | Day 12 | Day 13 | Day 14 | Days 15-20 [d] | Day 21 | Days 22-27 [e] | Day 28 (EOS) [f] |
| Written informed consent [g] | | | | | | | | | | | |
| Inclusion/exclusion criteria | | | | | | | | | | | |
| Confirm SARS-CoV-2 positive [h] | | | | | | | | | | | |
| Medical history/demographics | | | | | | | | | | | |
| Chest CT scan or X-ray [i] | | | | | | | | | | | X |
| Physical examination [j] | | | | | | | | | | | X |
| Height and body weight | | | | | | | | | | | |
| Pregnancy test [k] | | | | | | | | | | | |
| Urinalysis [l] | | | | | | | | | | | X |
| Vital signs [m] | | | X | X | X | X | X | X | X | X | X |
| Respiratory parameters [n] | | | X | X | X | X | X | X | X | X | X |
| Assisted ventilation Parameters [o] | | | X | X | X | X | X | X | X | X | X |
| SOFA score | | | X | | | | X | | X | | X |
| Randomization | | | | | | | | | | | |
| IRT Assignment to IMP kits [p] | | | | | | | | | | | |
| Administration of IMP [q] | | | | | | | | | | | |
| Blood samples for laboratory testing | Local | Hematology/ANC | X | X | X | X | X | | X | | X |
| | | Biochemistry/ferritin | X | | | | | X | X | | X |
| | | Coagulation Procalcitonin | X | | | | | X | X | | X |
| | Per CSL | Biomarkers [s] | | | | | | X | X | | X |
| | | ADA RNA | | | | | | X | X | | X |
| | | PK [t] | | | | | | X | X | | X |
| Outcome assessments | | | X | X | X | X | X | X | X | X | X |
| AEs | | | X | X | X | X | X | X | X | X | X [u] |
| Concomitant medication/therapy | | | X | X | X | X | X | X | X | X | X |

AE = adverse event;
aPTT = activated partial thromboplastin time;
β-hCG = beta human chorionic gonadotropin;
BiPAP = bilevel positive airway pressure;
C1-INH = C1 esterase inhibitor;
CPAP = continuous positive airway pressure:
CT = computed tomography;
ECMO = extracorporeal membrane oxygenation;
EOS = end of study;
$FiO_2$ = fraction of inspired oxygen;
h = hours;
HFNC = high-flow nasal cannula;
ICU = intensive care unit;
IMP = investigational medicinal product;
INR = international normalized ratio;
IV = intravenous;
min = minutes;
NA = not applicable;
NIV = non-invasive ventilation;
$O_2$ = oxygen;
PAI-1 = plasminogen activator inhibitor-1;
$PaO_2$ = partial pressure of arterial oxygen;
PD = pharmacodynamics;
PK = pharmacokinetic;
PT = prothrombin time;
SARS-Co-V-2 = Severe Acute Respiratory Syndrome Coronavirus-2;
SOC = standard of care;
SOFA = Sequential Organ Failure Assessment;
$SpO_2$ = saturation of peripheral (capillary) oxygen;
sRAGE = soluble form of receptor for advanced glycation end products;
TT = thrombin time.

TABLE 8-continued

Schedule of assessments

[a] For subjects discharged from the hospital before Day 28 who are unable or unwilling to visit the hospital to complete planned assessments, a weekly phone call is made to assess clinical status and AEs. These subjects are encouraged to return for the Day 28 Visit, but if they are unable to do so, a phone call is made on Day 28 to assess clinical status and AEs.
[b] If Screening occurs on Day 1, then assessments scheduled to occur at both Screening and before dosing on Day 1 are performed only once (ie, do not need to be repeated).
[c] Time for assessments required to be performed after dosing, is calculated from the start of the infusion of IMP.
[d] Assessments are performed on each of Days 15, 16, 17, 18, 19, and 20.
[e] Assessments are performed on each of Days 22, 23, 24, 25, 26, and 27.
[f] For subjects who withdraw from the study before Day 28, attempts are made to complete Day 28 (EOS) assessments. If a subject is not able to participate in the Day 28 visit in person, then the subject is contacted by telephone.
[g] Written informed consent must be obtained before any study-specific assessments or procedures are performed. An individual legally permitted to make medical decisions on the subject's behalf can provide written informed consent.
[h] Positive result for SARS-CoV-2 using a clinically acceptable test; test at Screening can be waived if positive result was available using clinically acceptable test within 14 days before screening.
[i] Thoracic CT scan or X-ray can be waived if available and taken within 48 hours prior to randomization
[j] A physical examination is conducted per the investigator's standard procedure.
[k] A urine test for $\beta$-hCG is performed at the local laboratory for all female subjects of childbearing potential to rule out pregnancy during Screening. A serum pregnancy test is performed by the site if urine result is inconclusive.
[l] Urinalysis and urine pregnancy testing is performed at the local laboratory.
[m] Vital sign assessments include blood pressure (systolic and diastolic), pulse rate, and body temperature. Blood pressure and heart rate is measured with the subject in a supine or seated position after resting for $\geq 5$ minutes. Body temperature is measured either sublingually or tympanically, and the method of measurement should be consistent throughout the study for a given subject. Vital signs should be measured once daily, ideally performed together at the same time of the day in the morning during the course of the study.
[n] Respiratory parameters include the following: respiratory rate (breaths per minute), $SpO_2$ (%), $FiO_2$ (room air includes 21% oxygen, which is equivalent to $FiO_2$ of 0.21), and $PaO_2$ (mmHg). Respiratory parameters should be measured once daily, ideally performed together at the same time of the day in the morning.
[o] Assisted ventilation parameters is recorded once daily if and when assisted ventilation is commenced and until cessation or death. All methods including $O_2$ supplementation, HFNC, CPAP, BiPAP, ECMO, intubation and mechanical ventilation (include mode, $FiO_2$, rate, peak inspiratory pressure, positive end expiratory pressure, mean airway pressure, tidal volume, recorded after subject has been in the supine position for $\geq 30$ minutes).
[p] Blinded IMP is either CSL324 or placebo.
[q] Administration of each dose occurs only if ANC is $\geq 1.5 \times 10^9$ cells/L and if procalcitonin is <0.25 ng/mL.
[r] Administration of the first dose of IMP occurs $\leq 6$ hours after randomization.
[s] Biomarkers may include (but are not limited to) the following: G-CSF, inflammatory cytokines, neutrophil elastase, and sRAGE, PAI-1. Any remaining biomarkers blood samples may be retained for further exploratory biomarker analysis and research relevant to the study objectives.

Efficacy Assessments

Outcome assessments include the subject's use of supplemental oxygen, CPAP, BiPAP, HFNC, endotracheal intubation/mechanical ventilation, extubation, clinical status on standardized scales, ICU admission and discharge; and hospital discharge or death.

Demographics and Safety Assessments

The clinical procedures conducted during this study related to the evaluation of safety are provided below in Table 9.

TABLE 9

Safety assessments

| Assessment | Description | | |
|---|---|---|---|
| Demographics | Year of birth/age | Sex | Race and ethnicity |
| Medical History | Relevant medical history | Previous/concomitant medications/therapies | |
| | Smoking history | Contraception method (if relevant) | |
| Pregnancy Test (local laboratory) | $\beta$-hCG urine test (female subjects of childbearing potential serum pregnancy test will be performed by the site if urine result is inconclusive | | |
| Physical Examination | As per the site's standard procedure | | |
| Chest Imaging | Chest CT scan or X-ray | | |
| Adverse Events | Evaluation of all AEs (eg, causality/relatedness, severity, seriousness) AESIs: Grade 3 and 4 neutropenia Grade 3 and 4 hospital-acquired infections | | |
| Vital Signs | Blood pressure (systolic/diastolic) | Temperature | |
| | Respiratory rate | Height | |
| | Pulse rate | Weight | |
| Respiratory Parameters | Respiratory rate | $FiO_2$ | |
| | $SpO_2$ | $PaO_2$ | |
| Urinalysis (dipstick) (test kits provided for local laboratory) | Specific gravity | Nitrite | Protein |
| | pH | Ketones | Glucose |
| | Leukocyte esterase | Bilirubin | |
| | Occult blood | Urobilinogen | |
| Hematology (local laboratory) | Hemoglobin | Reticulocytes | |
| | Hematocrit | Platelets | |
| | Erythrocytes (RBC count) | Leukocytes (WBC count) | |
| | RBC indices: mean corpuscular volume; mean corpuscular hemoglobin; mean corpuscular hemoglobin concentration; erythrocyte distribution width | Differential (percentage or absolute): neutrophils; neutrophil band forms; lymphocytes; monocytes; eosinophils; basophils | |
| Biochemistry (local laboratory) | Sodium | AST | |
| | Potassium | GGT | |
| | Chloride | Bilirubin, total | |
| | Bicarbonate | Direct bilirubin | |
| | Carbon dioxide, total | Magnesium | |

TABLE 9-continued

| Safety assessments | | |
|---|---|---|
| Assessment | Description | |
| | Calcium | Phosphate |
| | Blood urea nitrogen | CRP |
| | Urea | Cholesterol, total |
| | Creatinine | Triglycerides |
| | Glucose | HDL cholesterol |
| | Protein, total | LDL cholesterol |
| | Albumin | Urate (uric acid) |
| | Alkaline phosphatase | CK, CPK |
| | ALT | C3, C4 |
| | LDH | Ferritin |
| | | Procalcitonin |
| Coagulation | aPTT | Fibrinogen (Clauss assay) |
| (local laboratory) | PT/INR | D-dimer |
| Cytokine Profile | Inflammatory cytokine panel | |
| (designated laboratory) | | |
| Anti-drug | Serum analyzed for the presence of antibodies binding specifically | |
| antibodies | to CSL324 | |
| (designated laboratory) | | |

AESI = adverse events of special interest;
ALT = alanine aminotransferase;
aPTT = activated partial thromboplastin time;
AST = aspartate aminotransferase;
β-hCg = beta-human chorionic gonadotropin;
BUN = blood urea nitrogen;
CK/CPK = creatine kinase;
CRP = C-reactive protein;
ECG = electrocardiogram;
CRS = cytokine release syndrome;
eCRF = electronic case report form;
$FiO_2$ = fraction of inspired oxygen;
GGT = gamma-glutamyl transferase;
HAV = hepatitis A virus;
HBV = hepatitis A virus;
HCV = hepatitis C virus;
HDL = high-density lipoprotein;
IL = interleukin;
INR = international normalized ratio;
LDH = lactate dehydrogenase;
LDL = low-density lipoprotein;
$PaO_2$ = partial pressure of arterial oxygen;
QTcB = Bazett's correction formula;
QTcF = Fridericia's correction formula;
PT = prothrombin time;
RBC = red blood cell;
$SpO_2$ = saturation of peripheral (capillary) oxygen;
TNF-α = tumor necrosis factor-alpha;
TEE = thromboembolic event;
WBC = white blood cell.

Pharmacodynamic Assessments

Pharmacodynamic endpoints include serum G-CSF concentrations. Further exploratory biomarker analyses relevant to neutrophil activation and the pathophysiology of acute respiratory distress syndrome are performed, which may include but are not limited to sRAGE, PAI-1, neutrophil elastase, and inflammatory cytokines.

Halting Criteria

Subject

If a subject meets any of the following criteria during participation in the study, then further administration of IMP to that subject is halted (ie, temporarily paused) until an assessment of that subject's safety is completed:

Occurrence of a Serious AE (SAE) and is considered to be related to the administration of CSL324 by the investigator and/or CSL Clinical symptoms of G3 or G4 Systemic administration related reactions (SARR) during OR within the first 24 hours after the end of an infusion If at any time after randomisation, ANC $<1.5\times10^9$ cells/L and is confirmed on repeat measurement within 12 hours Clinical or laboratory evidence or suspicion of hospital acquired infection Any event or laboratory abnormality that is considered by the PI and/or Sponsor to pose an unacceptable risk to the subject in the study Study If any of the following criteria are met, then all further administration of IMP and further enrolment of new subjects is halted (ie, temporarily paused) until an assessment of the overall safety of continuing the study or not is completed:

One or more subject/s develops a SAE that results in death and is considered to be related to the administration of CSL324 by the investigator and/or CSL One or more subject(s) develops any other serious event that is deemed to pose an unacceptable risk in other subjects in the study and is considered to be related to the administration of CSL324 by the investigator and/or CSL Overall pattern of symptomatic, clinical, or laboratory events that the medical monitor, CSL or IDMC consider associated with CSL324 and that may appear minor in terms of individual events but that collectively may represent a serious potential concern for safety Grade 4 neutropenia (ANC <0.5×10⁹ cells/L) at the assessment of the sentinel safety groups (ie, in the first 5, 10, 20, 30, and 45 subjects on active) in any of the following:

1 or more of the first 5 active subjects 2 or more of the first 10 active subjects 3 or more subjects thereafter Two or more subjects experience grade 2 or above related neutropenia (defined as ANC <1.5×10⁹ cells/L) and is confirmed on repeat measurement, along with evidence of hospital acquired infection post manifest neutropenia Adverse Event As per ICH E2A (Clinical Safety Data Management: Definitions and Standards for Expedited Reporting), an adverse event (AE) is any untoward medical occurrence in a patient or clinical investigation subject administered a pharmaceutical product and which does not necessarily have a causal relationship with this treatment. An AE can, therefore, be any unfavorable and unintended sign (including an abnormal, clinically significant laboratory finding), symptom, or disease temporally associated with the use of a medicinal (investigational) product, whether or not considered related to the medicinal (investigational) product.

The period of observation for AEs extends from the time that informed consent is obtained until the end of study.

Adverse events may include:

Exacerbation (ie, an increase in the frequency or severity) of a pre-existing condition. Illness present before study entry should be recorded in the medical history section of the eCRF and only be reported as an AE if there is an increase in the frequency or severity of the condition during the study.

A clinical event occurring after consent but before IMP administration.

Intercurrent illnesses with an onset after administration of IMP.

Adverse events do not include:

Events identified at screening that meet exclusion criteria.

Medical or surgical procedures (the condition that leads to the procedure is the AE).

Situations where an untoward medical occurrence has not taken place. For example:

Planned hospitalizations due to pre-existing conditions, which have not worsened.

Hospitalizations that occur for procedures not due to an AE (eg, cosmetic surgery)

Hospitalizations for a diagnostic procedure where the hospital stay is less than 24 hours in duration or for normal management procedures (eg, chemotherapy).

Overdose of IMP or any concomitant therapy that does not result in any adverse signs or symptoms.

For laboratory safety parameters, any instances of absolute values being outside the reference range or changes at any visit after study start that are considered by the investigator as clinically significant must recorded in the eCRF as AEs. In addition, at the investigator's discretion, any changes or trends over time in laboratory parameters can be recorded in the eCRF as AEs if such changes or trends are considered to be clinically relevant, even if the absolute values are within the reference range.

Laboratory findings do not need to be reported as AEs in the following cases:

Laboratory parameters already beyond the reference range at screening, unless a further increase/decrease can be considered an exacerbation of a pre-existing condition.

Abnormal laboratory parameters caused by mechanical or physical influences on the blood sample (eg, in vitro hemolysis) and flagged as such by the laboratory in the laboratory report.

Abnormal parameters that are obviously biologically implausible (eg, values that are incompatible with life or outside the measuring range).

An abnormal laboratory value that cannot be confirmed after repeat analysis, preferably in the same laboratory (ie, the previous result could be marked as not valid and should not necessarily be reported as an AE).

Serious Adverse Event

A serious adverse event (SAE) is defined as any untoward medical occurrence that at any dose:

Results in death—The event must be the cause of death for the SAE to meet this serious criterion.

Is life-threatening—The term "life-threatening" refers to an event in which the subject was at risk of death at the time of the event; it does not refer to an event that hypothetically might have caused death if it had been more severe.

Requires in-patient hospitalization or prolongation of existing hospitalization—"hospitalization or prolongation of existing hospitalization" for ≥24 hours is considered the defining criterion for an SAE. Hospital admissions for planned surgery or for normal disease management procedures (eg, chemotherapy) are not considered as defining criteria for SAEs.

Results in persistent or significant disability or incapacity.

Is a congenital anomaly or birth defect.

Is medically significant—A medically significant event is defined as an event that does not necessarily meet any of the SAE criteria, but which is judged by a physician to potentially jeopardize the subject or require medical or surgical intervention to prevent one of the above outcomes listed as an SAE criterion.

Adverse events that do not fall into the above categories are defined as nonserious AEs.

Adverse Event of Special Interest

There are several AEs that are monitored closely as AEs of special interest (AESIs) to enable an adequate risk-benefit evaluation of CSL324 during the study and additional data may be requested for these events. The AESIs are:

Grade 3 and Grade 4 neutropenia (ANC <1×10⁹ cells/L and ANC <0.5×10⁹ cells/L respectively)

Grade 3 and Grade 4 hospital-acquired infections Grading of AEs will be according to CTCAE criteria (Version 5, 27 Nov. 2017).

Severity of Adverse Events

The severity of each AE (ie, non-serious and serious AEs) is assessed as follows:

| Severity | Definition |
|---|---|
| Mild | A type of AE that is usually transient and may require only minimal treatment or therapeutic intervention. The event does not generally interfere with usual activities of daily living. |
| Moderate | A type of AE that is usually alleviated with additional specific therapeutic intervention. The event interferes with usual activities of daily living, causing discomfort but poses no significant or permanent risk of harm to the subject. |

-continued

| Severity | Definition |
|---|---|
| Severe | A type of AE that interrupts usual activities of daily living, or significantly affects clinical status, or may require intensive therapeutic intervention. |

Clinical Data Interchange Standards Consortium (CDISC) Study Data Tabulation Model (SDTM) Severity Intensity Scale for Adverse Event Terminology.

Analyses of Primary Efficacy

The primary endpoint for this study is the rate of progression to endotracheal intubation or death within 28 days after administration of study treatment. The proportion is calculated as the number of subjects with progression to endotracheal intubation or death divided by the total number of subjects for each treatment group. Treatment effect of interest (ie, estimand) is defined as the odds ratio of progression to endotracheal intubation or death (CSL324+SOC versus placebo+SOC) in the target population regardless of whether additional treatment is used or initial SOC has changed. The ITT Analysis Set is used for the primary endpoint analyses.

Firth logistic regression model including treatment group, age (as 65 years or ≥65 years), gender (male or female) and smoking status (yes or no) in the model is used to compare the rates between the two treatment groups. The OR, associated 90% confidence interval (CI), and 1-sided p-value are estimated from the model. The mITT Analysis Set is used for primary efficacy endpoint sensitivity analysis.

Analyses of Secondary Efficacy

Frequency and proportion of subjects for the following secondary efficacy endpoints are summarized:

All-cause mortality

Incidence of endotracheal intubation from randomization to Day 28

Clinical status as assessed on an 8-point NIAID ordinal scale

Use of the following captured independently: 1) CPAP or BiPAP, 2) HFNC, or 3) ECMO The same testing method used for primary efficacy variable is also be used to compare the above secondary efficacy endpoints between the 2 treatment groups. The ORs, associated 95% CIs, and 2-sided p-values are reported.

Days Alive and Ventilator Free

The median number of days subjects were alive and ventilator free is analyzed for each treatment arm.

Clinical Status Assessed on an 8-Point NIAID Ordinal Scale

Frequency and proportion of subjects within each category of the 8-point NIAID ordinal scale are summarized for each treatment arm. Frequency and proportion of subjects with at least a 2-point improvement from baseline is analyzed.

Hospital Length of Stay

Hospital LOS is defined as time interval from randomization to hospital discharge. In this analysis, subjects who did not have hospital discharge (ie, no recorded date of hospital discharge), time to discharge is censored at the last hospital discharge assessment date if the subject did not complete the 28-day treatment period. For subjects who do not have an event or censoring time within the first 28 days after randomization or a subject has died, an administrative censoring is applied at 28 days.

Sequential Organ Failure Assessment (SOFA)

Change from baseline in SOFA score is summarized by treatment groups. Descriptive statistics for continuous variables are reported. Nonparametric Wilcoxon rank-sum test is used to compare the two treatment groups.

The ITT Analysis Set and mITT Analysis Set are used for the secondary efficacy endpoint analyses.

All analysis is based on 2-side test at $\alpha$=0.05.

Analysis of Safety

Adverse events are coded using the Medical Dictionary for Regulatory Activities (MedDRA) version 21.1 (or higher). A treatment-emergent adverse event (TEAE) is defined as an AE reported at or after the start of the first administration of study treatment. Only TEAEs are summarized.

An overview summary of TEAEs, including counts and percentages of subjects with any TEAE; TEAEs related to study treatment; TEAEs leading to permanent discontinuation of study treatment; TEAE leading to dose modifications; serious TEAEs; serious TEAEs related to study treatment; fatal TEAEs; fatal TEAEs related to study treatment, TEAEs by severity, and TEAEs of special interest are produced.

TEAEs are summarized by system organ class and preferred term. TEAEs are also be summarized by causality and severity. All TEAE summaries are provided for each treatment and overall.

Number and percentage of subjects with serum anti-CSL324 antibodies are summarized by treatment group and overall.

Laboratory evaluations (hematology, biochemistry, and urinalysis) are summarized descriptively by treatment group.

Vital sign findings are listed by subject and time point. The values and change from Baseline at each visit are descriptively summarized by treatment group.

Analyses of Pharmacokinetics

The PK data of for CSL324 serum concentration is summarized by nominal time point for each treatment. The following descriptive statistics are presented for serum concentration summaries: n, arithmetic mean, SD, CV %, median, geometric mean, minimum, and maximum.

The PK parameters for CSL324, derived using a non-compartmental method, are summarized descriptively by treatment group.

The following PK parameters will be derived and summarized:

$C_{max}$

AUC from time zero to end of the dosing period ($AUC_{0-4}$)

$T_{max}$

The following descriptive statistics are presented for all PK parameters, except for $T_{max}$: n, arithmetic mean, SD, CV %, median, geometric mean, minimum, and maximum. For $T_{max}$, n, median, minimum and maximum are summarized.

Exploratory Analysis

The following time to event variables are analyzed using survival analysis method:

Time on mechanical ventilation: only defined for subjects who were on intubation as time from intubation to extubation. In this analysis, subjects who were not extubated (ie, no recorded date coming out of ICU), time to coming extubation is censored at the last extubation assessment date if the subject did not complete the 28-day treatment period. For subjects who do not have an event or censoring time within the first 28 days after randomization or a subject has died, an administrative censoring is applied at 28 days.

ICU length of stay: only defined for subjects who were in ICU as time from entry to ICU to coming out of ICU. In this analysis, subjects who did not come out of ICU (ie, no recorded date of coming out of ICU), time to coming out of ICU is censored at the last coming out of ICU assessment date if the subject did not complete the 28-day treatment period. For subjects who do not have an event or censoring time within the first 28 days after randomization or a subject has died, an administrative censoring is applied at 28 days.

The PD profile of CSL324 is explored through exploratory biomarker assays. Biomarker data is summarized by study visit for each treatment group. The following descriptive statistics are presented for the continuous variables: n, arithmetic mean, SD, CV %, median, geometric mean, minimum, and maximum. For the categorical variables, count, and percentages are presented by treatment group.

The ITT Analysis Set and mITT Analysis Set is used for the exploratory efficacy analyses and PD Analysis Set is used for all PD analyses. All analysis is based on two-side test at α=0.05.

All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

---

The invention claimed is:

1. A method for reducing lung inflammation in a subject suffering from acute respiratory distress syndrome (ARDS) or at risk of developing ARDS, the method comprising administering a compound that inhibits granulocyte colony stimulating factor (G-CSF) signaling to the subject, wherein the compound that inhibits G-CSF signaling is a protein comprising an antigen binding site that specifically binds to G-CSF receptor (G-CSFR) and neutralizes G-CSF signaling, wherein the protein:

a) comprises an antibody variable region comprising a heavy chain variable region ($V_H$) comprising an amino acid sequence set forth in SEQ ID NO: 4 and a light chain variable region ($V_L$) comprising an amino acid sequence set forth in SEQ ID NO: 5; and/or b) comprises an antibody variable region comprising a $V_H$ comprising an amino acid sequence set forth in SEQ ID NO: 2 and a $V_L$ comprising an amino acid sequence set forth in SEQ ID NO: 3; and/or c) comprises an antibody variable region comprising a $V_H$ comprising three complementarity determining regions (CDRs) of a $V_H$ comprising an amino acid sequence set forth in SEQ ID NO: 4 and a $V_L$ comprising three CDRs of a $V_L$ comprising an amino acid sequence set forth in SEQ ID NO: 5, wherein the CDRs are defined according to the numbering system of Kabat.

2. The method of claim 1, wherein the ARDS is associated with one or more of the following:

a) an infection;

b) inhalation or aspiration of a foreign substance;

c) a physical trauma; and d) an inflammatory disease.

3. The method of claim 1, wherein the ARDS is associated with a viral infection and/or a coronavirus infection.

4. The method of claim 1, wherein the subject has coronavirus disease 2019 (COVID-19) and/or interstitial pneumonia.

5. The method of claim 1, wherein the subject has one or more or all of the following a) a respiratory frequency of greater than 30 breaths per minute;

b) an oxygen saturation ($SpO_2$) of 93% or less on room air;

c) a ratio of arterial partial pressure of oxygen to fraction of inspired oxygen ($PaO_2/FiO_2$) of less than 300 mmHg;

d) a $SpO_2/FiO_2$ ratio of less than 218; and e) radiographic lung infiltrates in an amount of greater than 50%.

6. The method of claim 1, wherein the compound that inhibits G-CSF signaling is administered in an amount sufficient to prevent endotracheal intubation or death prior to endotracheal intubation.

7. The method of claim 1, wherein the compound that inhibits G-CSF signaling is administered in an amount sufficient to achieve one or more or all of the following:

a) increase the subject's days alive and ventilator free;

b) decrease the subject's hospital length of stay (LOS);

c) improve the subject's clinical status as assessed on an 8-point National Institute of Allergy and Infectious Disease (NIAID) ordinal scale;

d) reduce or prevent use of continuous positive airway pressure (CPAP) or bilevel positive airway pressure (BiPAP);

e) reduce or prevent use of high-flow nasal cannula (HFNC);

f) reduce or prevent use of extracorporeal membrane oxygenation (ECMO); and g) reduce or prevent an increase in the subject's Sequential Organ Failure Assessment (SOFA) score.

8. The method of claim 1, wherein the protein comprises:

(i) a heavy chain comprising an amino acid sequence set forth in SEQ ID NO: 14 and a light chain comprising an amino acid sequence set forth in SEQ ID NO: 15; or (ii) a heavy chain comprising an amino acid sequence set forth in SEQ ID NO: 18 and a light chain comprising an amino acid sequence set forth in SEQ ID NO: 15.

9. The method of claim 1, wherein the protein is a fusion protein, wherein the fusion protein comprises:

a) serum albumin or a variant thereof; or b) a soluble complement receptor or a variant thereof.

10. The method of claim 1, wherein the compound that inhibits G-CSF signaling is administered in an amount sufficient to:

a) reduce circulating neutrophils in the subject without causing sustained grade 3 or grade 4 neutropenia for greater than seven consecutive days; or b) reduce circulating neutrophils in the subject without causing sustained grade 2 or grade 3 or grade 4 neutropenia for greater than two consecutive days.

11. The method of claim 1, wherein the protein is administered at a dose of between 0.1 mg/kg to 0.8 mg/kg, or at a dose of between 0.1 mg/kg to 0.6 mg/kg, or at a dose of 0.1 mg/kg or 0.3 mg/kg or 0.6 mg/kg.

12. The method of claim 1, comprising administering multiple doses of the protein to the subject, wherein the protein is administered once every 2 to 5 days, wherein:

a) the first dose of the protein is higher than subsequent doses; and/or b) the method comprises administering at least two doses of the protein to the subject.

13. The method of claim 12, comprising administering the protein to the subject in a first dose of between 0.1 mg/kg and 0.4 mg/kg, and a further one or more doses of between 0.05 mg/kg and 0.2 mg/kg, wherein the second dose is three days after the first dose and the third dose is four days after the second dose.

14. The method of claim 1, wherein the compound that inhibits G-CSF signaling is administered intravenously and/ or subcutaneously and/or is administered in combination with a standard of care therapy.

15. The method of claim 14, wherein the standard of care therapy comprises one or more or all of the following:

a) prone positioning;

b) fluid management;

c) administration of nitric oxide;

d) administration of a neuromuscular blocking agent;

e) artificial ventilation;

f) extracorporeal membrane oxygenation; and g) administration of an antiviral agent or antibiotic.

16. The method of claim 14, wherein the standard of care therapy comprises administration of remdesivir.

17. The method of claim 1, wherein the subject at risk of developing ARDS has pneumonia.

\* \* \* \* \*